US009308248B2

(12) United States Patent
Vanrompay

(10) Patent No.: US 9,308,248 B2
(45) Date of Patent: Apr. 12, 2016

(54) **VACCINES FOR *CHLAMYDIA***

(75) Inventor: Daisy Vanrompay, Oosterzele (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 14/126,076

(22) PCT Filed: Jun. 15, 2012

(86) PCT No.: PCT/EP2012/061420
§ 371 (c)(1),
(2), (4) Date: Dec. 13, 2013

(87) PCT Pub. No.: WO2012/172042
PCT Pub. Date: Dec. 20, 2012

(65) Prior Publication Data
US 2014/0242105 A1    Aug. 28, 2014

(30) Foreign Application Priority Data
Jun. 17, 2011   (EP) .................................. 11170370

(51) Int. Cl.
*A61K 39/00* (2006.01)
*A61K 39/02* (2006.01)
*A61K 39/002* (2006.01)
*A61K 39/118* (2006.01)
*C07K 14/295* (2006.01)

(52) U.S. Cl.
CPC ............. *A61K 39/118* (2013.01); *C07K 14/295* (2013.01)

(58) Field of Classification Search
CPC .................................................. A61K 39/118
See application file for complete search history.

(56) References Cited

U.S. PATENT DOCUMENTS

| | | | |
|---|---|---|---|
| 5,759,551 A | 6/1998 | Ladd et al. | |
| 6,384,206 B1 * | 5/2002 | Caldwell et al. | 536/23.7 |
| 2005/0037019 A1 * | 2/2005 | Kousoulas et al. | 424/190.1 |

FOREIGN PATENT DOCUMENTS

WO    9406827 A1    3/1994

OTHER PUBLICATIONS

Plotkin et al (Vaccines WB Saunders Company, p. 571, 1988).*
Hafner et al (Vaccine vol. 32, pp. 1563-1571, 2014).*
Salgaller et al (Cancer Immunol. Immunother. vol. 39, pp. 105-116, 1994).*
Beatty et al., "Cross Reactive Cytotoxic T-Lymphocyte-Mediated Lysis of Chlamydia trachomatis- and Chlamydia psittaci-Infected Cells", Infection and Immunity, vol. 65, No. 3, pp. 951-956, Mar. 1997.
Beck et al., "Peptides as tools and drugs for immunotherapies", Journal of Peptide Science, vol. 13, pp. 588-602, Jun. 29, 2007.
Cotter et al., "Protective Efficacy of Major Outer Membrane Protein-Specific Immunoglobulin A (IgA) and IgG Monoclonal Antibodies in a Murine Model of Chlamydia trachomatis Genital Tract Infection", Infection and Immunity, vol. 63, No. 12, pp. 4704-4714, Dec. 1995.
Cotter et al., "Dissemination of Chlamydia trachomatis Chronic Genital Tract Infection in Gamma Interferon Gene Knockout Mice", Infection and Immunity, vol. 65, No. 6, pp. 2145-2152, Jun. 1997.
Kelly, "Cellular Immunity and Chlamaydia Genital Infection: Induction, Recruitment, and Effector Mechanisms", International Reviews of Immunology, vol. 22, pp. 3-41, 2003.
Knight et al., "A peptide of Chlamydia trachomatis shown to be a primary T-cell epitope in vitro induces cell-mediated immunity in vivo", Immunology, vol. 85, pp. 8-15, 1995.
Li et al., "Synthetic peptides containing B- and T-cell epitope of dengue virus-2 E domain III provoked B- and T-cell responses", Vaccine, vol. 29, pp. 3695-3702, Mar. 2011.
Longbottom et al., "Vaccination against chlamydial infections of main and animals", The Veterinary Journal, vol. 171, pp. 263-275, 2006.
Mahajan et al., "Multiple Antigen Peptide Vaccines against Plasmodium falciparum Malaria", Infection and Immunity, vol. 78, No. 11, pp. 4613-4624, Nov. 2010.
Morrison et al., "Immunity to Murine Chlamydia trachomatis Genital Tract Reinfection Involves B Cells and CD4+ T Cells but Not CD8+ T Cells", Infection and Immunity, vol. 68, No. 12, pp. 6979-6987, Dec. 2000.
Sanchez-Burgos et al., "Immunogenicity of novel Dengue Virus epitopes identified by bioinformatic analysis", Virus Research, vol. 153, pp. 113-120, 2010.
Sandbulte et al., "Evaluation of Chlamydia psittaci subfraction and subunit preparations for their protective capacities", Veterinary Microbiology, vol. 48, pp. 269-282, 1996.
Schulze et al., "Identification of B- and T-Cell Epitopes within the Fibronectin-Binding Domain of the Sfbl Protein of *Streptococcus pyogenes*", Infection and Immunity, vol. 71, No. 12, pp. 7191-1201, Dec. 2003.
Su et al., "CD4+ T Cells Play a Significant Role in Adoptive Immunity to Chlamydia trachomatis Infection of the Mouse Genital Tract", Infection and Immunity, vol. 63, No. 9, pp. 3302-3308, Sep. 1995.
Su et al., "Chlamydia trachomatis Genital Tract Infection of Antibody-Deficient Gene Knockout Mice", Infection and Immunity, vol. 65, No. 6, pp. 1993-1999, Jun. 1997.
Tan et al., "Protection of Sheep against Chlamydia psittaci Infection with a Subcellular Vaccine Containing the Major Outer Membrane Protein", Infection and Immunity, vol. 58, No. 9, pp. 3101-3108, Sep. 1990.
Vanrompay et al., "Diagnosis of avian chlamydiosis: specificity of the modified Gimenez staining on smears and comparison of the sensitivity of isolation in eggs and three different cell cultures", J. Vet. Med. B., vol. 30, pp. 105-112, 1992.

(Continued)

*Primary Examiner* — Albert Navarro
(74) *Attorney, Agent, or Firm* — Dinsmore & Shohl LLP

(57) ABSTRACT

The present invention relates to means and methods to protect against disease caused by bacteria belonging to the genus *Chlamydia*. In particular, the present invention relates to isolated B- and T-cell epitopes derived from the major outer membrane protein of *Chlamydia psittaci* which can be used against an infection with a species of the genus *Chlamydia*. More in particular, the invention provides a vaccine which can be used against chlamydiosis caused by *Chlamydia psittaci* in birds and man. In addition, the invention relates to a diagnostic method to diagnose the latter infections.

22 Claims, 23 Drawing Sheets

(56) References Cited

OTHER PUBLICATIONS

Figure 1:
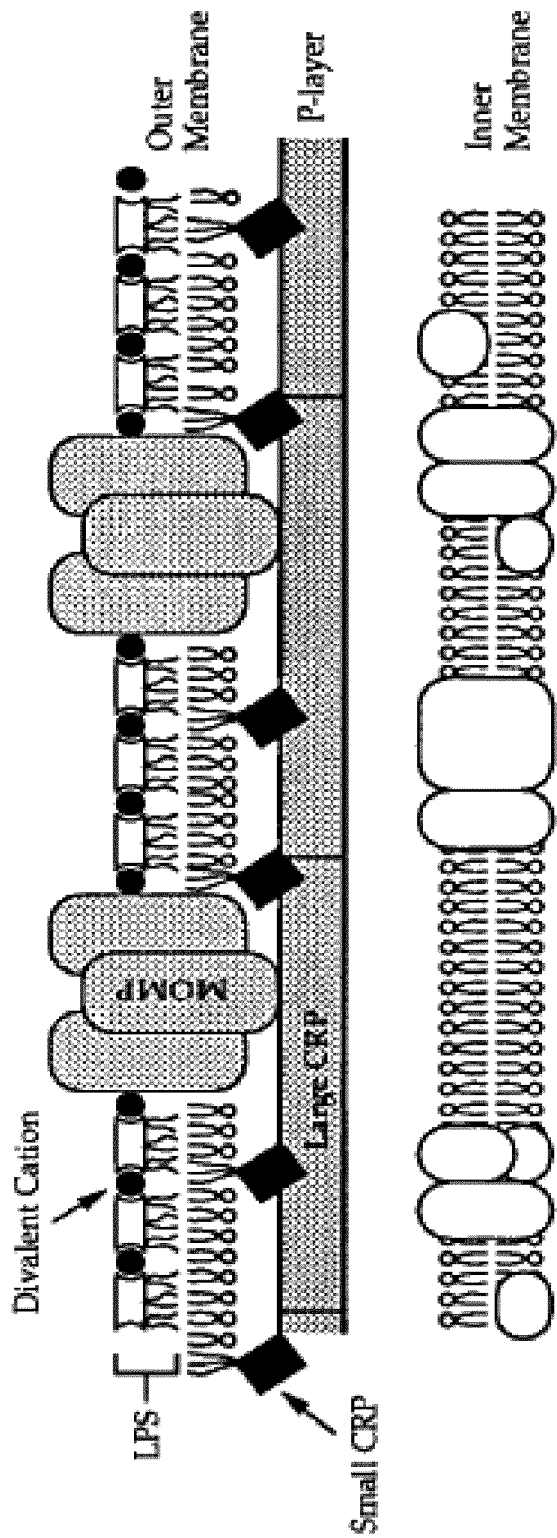

Vanrompay et al., "Evaluation of Five Immunoassays for Detection of Chlamydia psittaci in Cloacal and Conjunctival Specimens from Turkeys", Journal fo Clinical Microbiology, vol. 32, No. 6, pp. 1470-1474, Jun. 1994.

Vanrompay et al., "Pathogenicity for turkeys of Chlamydia psittaci strains belonging to the avian serovars A, B and D", Avian Pathology, vol. 23, pp. 247-262, 1994.

Vanrompay et al., "High-Level Expression of Chlamydia psittaci Major Outer Membrane Protein in COS Cells and in Skeletal Muscles of Turkeys", Infection and Immunity, vol. 66, No. 11, pp. 5494-5500, Nov. 1998.

Vanrompay et al., "Turkeys are protected from infection with Chlamydia psittaci by plasmid DNA vaccination against the major outer membrane protein", Clin. Exp. Immunol. vol. 118, pp. 49-55, 1999.

Vanrompay et al., "Animal Models for the Study of Chlamydia Trachomatis Infections in the Fernal Genital Infection", Drugs of Today, vol. 41, pp. 55-63, 2005.

Verminnen et al., "Protection of turkeys against Chlamydophila psittaci challenge by DNA and rMOMP vaccination and evaluation of the immunomodulating effect of $1\alpha$, 25-dihydroxyviamin D3", Vaccine, vol. 23, pp. 4509-4516, 2005.

Verminnen et al., "Evaluation of a recombinant enzyme-linked immunosorbent assay for detecting Chlamydophila psittaci antibodies in turkey sera", Vet. Res., vol. 37, pp. 623-632, 2006.

Verminnen et al., "Vaccination of turkeys against Chlamydophila psittaci through optimised DNA fomulation and administration", Vaccine, vol. 28, pp. 3095-3105, 2010.

Williams et al., "Humoral and Cellular Immunity in Secondary Infection Due to Murine Chlamydia trachomatis", Infection and Immunity, vol. 65, No. 7, pp. 2876-2882, Jul. 1997.

Zhang et al., "Mucosal immunity in mice induced by orally administered transgenic rice", Vaccine, vol. 27, pp. 1596-1600, 2009.

Zhou et al., "Construction and immunogenicity of recombinant adenovirus expressing the major outer membrane protein (MOMP) of Chlamydophila psittaci in chicks", Vaccine, vol. 25, pp. 6367-6372, 2007.

\* cited by examiner

Figure 4

Outer membrane protein A genes

```
                                    1                                                                                    75
OmpA_Ctra_NC000117_CT681_RC     (1) ------------------------------------------------------------------------ATGAAAAAA
OmpA_Cmur_AE002160_TC0052_RC    (1) ------------------------------------------------------------------------ATGAAAAAA
OmpA_Cppn_NC000922_CPn0695      (1) ------------------------------------------------------------------------ATGAAAAAA
OmpA_Cpfel_NC007899_CF0958      (1) ------------------------------------------------------------------------ATGAAAAAA
OmpA_Cpcav_AE015925_CCA00047_RC (1) ------------------------------------------------------------------------ATGAAAAAA
OmpA_Cpabo_NC004552_CAB048_RC   (1) ------------------------------------------------------------------------ATGAAAAAA
OmpA_84-2334_AJ310735           (1) ------------------------------------------------------------------------ATGAAAAAA
OmpA_6BC_M73035                 (1) AGAAGAGCAAATTAGAATAGCGAGCACAAAAAGAAAAGATACTAAGCATAATCTTTAGAGGTGAGTATGAAAAAA
OmpA_CP3_AF269265               (1) ------------------------------------------------------------------------ATGAAAAAA
OmpA_GD_AF269261                (1) ------------------------------------------------------------------------ATGAAAAAA
OmpA_NJ1_AF269266               (1) ---------------------------------------------------------------------------AAA
PCR Omp1 D 92/1293              (1) ------------------------------------------------------------------------ATGAAAAAA
OmpA_MN-VR122-Cal10 AF269262    (1) ---------------------------------------------------------------------------
OmpA_VS225_AF269259             (1) ------------------------------------------------------------------------ATGAAAAAA
OmpA_WSRTE30_AY762613           (1) ------------------------------------------------------------------------ATGAAAAAA
OmpA_M56_AF269268               (1) ------------------------------------------------------------------------ATGAAAAAA
OmpA_WC_AF269269                (1) ---------------------------------------------------------------------------
Consensus                       (1)                                                                         ATGAAAAAA 76                                                                                   150
OmpA_Ctra_NC000117_CT681_RC    (10) CTCTTGAAATCGGTATTAGTATTTGCCGC--TTTGAGTTCGCTTCCTCCTTGCAAGCTCTGCCTGTGGGAAT
OmpA_Cmur_AE002160_TC0052_RC   (10) CTCTTGAAATCGGTATTAGCATTTGCCGT--TTTTGGGTTCGCTTCCTCCTTGCATGCTCTGCCTGTGGGAAT
OmpA_Cppn_NC000922_CPn0695     (10) CTCTTAAAGTCGGCGTTATTATCCGCCGCCATTTGCTGGTTCGTTGGCTCCTCCTTGGCTCCTTGCCTGTAGGGAAC
OmpA_Cpfel_NC007899_CF0958     (10) CTCTTAAAATCGGCATTATTATTTGCCGC--TGCGGGTTCCGCTTCCTCCTTACAAGCCTTGCCTGTAGGGAAT
OmpA_Cpcav_AE015925_CCA00047_RC (10) CTCTTGAAATCGGCATTATTGTTTGCCAC--TACGGGTTCCGCTTCCTCCTTACAAGCCTTGCCTGTAGGGAAT
OmpA_Cpabo_NC004552_CAB048_RC  (10) CTCTTGAAATCGGCATTATTGTTTGCCGC--TACGGGTTCCGCTTCCTCCTTACAAGCCTTGCCTGTAGGGAAC
OmpA_84-2334_AJ310735          (10) CTCTTGAAATCGGCATTATTGTTTGTTGCC-TACGGGTTCCGCTTCCTCCTTACAAGCCTTGCCTGTAGGGAAC
OmpA_6BC_M73035                (76) CTCTTGAAATCGGCATTATTGTTTGTTGCC-TACGGGTTCCGCTTCCTCCTTACAAGCCTTGCCTGTAGGGAAC
OmpA_CP3_AF269265              (10) CTCTTGAAATCGGCATTATTGTTTGTTGCC-TACGGGTTCCGCTTCCTCCTTACAAGCCTTGCCTGTAGGGAAC
OmpA_GD_AF269261               (10) CTCTTGAAATCGGCATTATTATTTGCCGC--TACGGGTTCCGCTTCCTCCTTACAAGCCTTGCCTGTAGGGAAC
OmpA_NJ1_AF269266               (4) CTCTTGAAATCGGCATTATTGTTTGCCGC--TACGGGTTCCGCTTCCTCCTTACAAGCCTTGCCTGTAGGGAAC
PCR Omp1 D 92/1293             (10) CTCTTGAAATCGGCATTATTGTTTGCCGC---CAAGCCTTGCCTGTAGGGAAC
OmpA_MN-VR122-Cal10 AF269262    (1) ---------------------------------------------------------
OmpA_VS225_AF269259            (10) CTCTTGAAATCGGCATTATTGTTTGCCGC--TACGGGTTCCGCTTCCTCCTTACAAGCCTTGCCTGTAGGGAAC
OmpA_WSRTE30_AY762613          (10) CTCTTGAAATCGGCATTATTGTTTGTTGCC-TACGGGTTCCGCTTCCTCCTTACAAGCCTTGCCTGTAGGGAAC
OmpA_M56_AF269268              (10) CTCTTGAAATCGGCATTATTGTTTGCCGC--TACGGGTTCCGCTTCCTCCTTACAAGCCTTGCCTGTAGGGAAC
OmpA_WC_AF269269                (1) ------AAATCGGCATTATTGTTTGTTGCC-TACGGGTTCCGCTTCCTCCTTACAAGCCTTGCCTGTAGGGAAC
Consensus                      (76) CTCTTGAAATCGGCATTATTGTTTGCCGC   TACGGGTTCCGCTTCCTCCTTACAAGCCTTGCCTGTAGGGAAC
```

```
                                           1351                                                          1425
OmpA_Ctra_NC000117_CT681_RC    (1183) ------------------------------------------------------------------------
OmpA_Cmur_AE002160_TC0052_RC   (1165) ------------------------------------------------------------------------
OmpA_Cppn_NC000922_CPn0695     (1171) ------------------------------------------------------------------------
OmpA_Cpfel_NC007899_CF0958     (1180) ------------------------------------------------------------------------
OmpA_Cpcav_AE015925_CCA00047_RC (1171) ------------------------------------------------------------------------
OmpA_Cpabo_NC004552_CAB048_RC  (1171) ------------------------------------------------------------------------
OmpA_84-2334_AJ310735          (1090) ------------------------------------------------------------------------
OmpA_6BC_M73035                (1288) ------------------------------------------------------------------------
OmpA_CP3_AF269265              (1281) TTTGCTACCACCCTTTTCAGA-GTTTCAAATCTCTTTTCTAAAATCCGTTCGCATCAGAATTCACTGATTATCTA
OmpA_GD_AF269261               (1248) TTTGCTCACATCCTTTTGTATAGCTTAATACCTCTCTTTTTTTAAAATCCATTCGCACAAGAATTCACTGATTATCTA
OmpA_NJ1_AF269266              (1245) TTTGCTACCACCCTTTTT-CAGAGTTTCAAATCTCTTTTCTAAAATCCATTCGCATCAGAGTTCAGTGATTATCTA
PCR_Omp1_D_92/1293             (1069) ------------------------------------------------------------------------
OmpA_MN-VR122-Ca110_AF269262   (1221) TTTGCTACCACCCTTTTCAGA-GTTTCAAATCTCTTTTCTAAAATCCGTTCGCATCAGAATTCACTGATTATCTA
OmpA_VS225_AF269259            (1239) TTTGCTACCACCCTTTTGCAGAGTTTCAAATCTCTTTTCTAAAATCCGTTCGCATAAGAATTCACTGATTATCTA
OmpA_WSRTE30_AY762613          (1099) ------------------------------------------------------------------------
OmpA_M56_AF269268              (1282) TTTGCCGCATTCTTTTTAGAAGTTTCAAATCTCTTTTCTAAAATCCATTGCACAAGCATTAACCACTATCTA
OmpA_WC_AF269269               (1248) TTTGCTACCACCCTTTGCAGAGTTTCAAATCTCTTTTCTAAAATCCGTTCGCATAAGAATTCACTGATTATCTA
                    Consensus  (1351)

1426                                                          1500
OmpA_Ctra_NC000117_CT681_RC    (1183) ------------------------------------------------------------------------
OmpA_Cmur_AE002160_TC0052_RC   (1165) ------------------------------------------------------------------------
OmpA_Cppn_NC000922_CPn0695     (1171) ------------------------------------------------------------------------
OmpA_Cpfel_NC007899_CF0958     (1180) ------------------------------------------------------------------------
OmpA_Cpcav_AE015925_CCA00047_RC (1171) ------------------------------------------------------------------------
OmpA_Cpabo_NC004552_CAB048_RC  (1171) ------------------------------------------------------------------------
OmpA_84-2334_AJ310735          (1090) ------------------------------------------------------------------------
OmpA_6BC_M73035                (1288) ------------------------------------------------------------------------
OmpA_CP3_AF269265              (1355) AAATTTTCTAGAAGCTAGAAACCTAGAGATTACAATCTTGCGTAAAAAGCATTATTAAATTATC-TCTCTATTCT
OmpA_GD_AF269261               (1323) AAATTTTCTAGAAGCTTGAAACCTAGAGATTACAACCTTGCGTAAAAAGCATTATTAAACTAACATCTCTATTCT
OmpA_NJ1_AF269266              (1319) AAATTTTCTAGAAGCTTGAAACCTAGAGATTACAACCTTGCGTAAAAAGCATTATTAAATTAACATCTCTATTCT
PCR_Omp1_D_92/1293             (1069) ------------------------------------------------------------------------
OmpA_MN-VR122-Ca110_AF269262   (1295) AAATTTTCTAGAAGCTAGAAACCTAGAAACCTAGAGATTACAATCTTGCGTAAAAAGCATTATTAAATTAACATCTCTATTCT
OmpA_VS225_AF269259            (1314) AAATTTTCTAGAAGCTAGAAACCTAGAAACCTAGAGATTACAATCTTGCGTAAAAAGCATTATTAAATTAACATCTCTATTCT
OmpA_WSRTE30_AY762613          (1099) ------------------------------------------------------------------------
OmpA_M56_AF269268              (1357) AAATTTTCTAGAAGCTTAAAACCTAGAAACCTAGAGATTACAACCTTGCGTAAAAAGCTTTATTAAACTAACATCTCTATTCT
OmpA_WC_AF269269               (1323) AAATTTTCTAGAAGCTAGAAACCTAGAAACCTAGAGATTACAATCTTGCGTAAAAAGCATTATTAAATTAACATCTCTATTCT
                    Consensus  (1426)
```

Figure 4 – continued (10)

| | | | |
|---|---|---|---|
| OmpA_Ctra_NC000117_CT681_RC | (1183) | ---------------------------------------- | (SEQ ID 123) |
| OmpA_Cmur_AE002160_TC0052_RC | (1165) | ---------------------------------------- | (SEQ ID 124) |
| OmpA_Cppn_NC000922_CPn0695 | (1171) | ---------------------------------------- | (SEQ ID 125) |
| OmpA_Cpfel_NC007899_CF0958 | (1180) | ---------------------------------------- | (SEQ ID 126) |
| OmpA_Cpcav_AE015925_CCA00047_RC | (1171) | ---------------------------------------- | (SEQ ID 127) |
| OmpA_Cpabo_NC004552_CAB048_RC | (1171) | ---------------------------------------- | (SEQ ID 128) |
| OmpA_84-2334_AJ310735 | (1090) | ---------------------------------------- | (SEQ ID 129) |
| OmpA_6BC_M73035 | (1288) | ---------------------------------------- | (SEQ ID 130) |
| OmpA_CP3_AF269265 | (1429) | TAGCACGCGCCCGTAGT----------------------- | (SEQ ID 131) |
| OmpA_GD_AF269261 | (1398) | TAGCACGCGCCCGTACTCAATGGT---------------- | (SEQ ID 132) |
| OmpA_NJ1_AF269266 | (1394) | TAGCACGCGCCCGTAGCTCAATGGTAGAGCTGTAGCC    | (SEQ ID 133) |
| PCR_Omp1_D_92/1293 | (1069) | ---------------------------------------- | (SEQ ID 134) |
| OmpA_MN-VR122-Cal10_AF269262 | (1370) | TAGCACGCGCCCGTAGCTCAATGG---------------- | (SEQ ID 135) |
| OmpA_VS225_AF269259 | (1389) | TAGCACGCGCCCGTAGCTCAATGGTAGAGCTGTAGCC    | (SEQ ID 136) |
| OmpA_WSRTE30_AY762613 | (1099) | ---------------------------------------- | (SEQ ID 137) |
| OmpA_M56_AF269268 | (1432) | TAGCACGCGCCCGTAGT----------------------- | (SEQ ID 138) |
| OmpA_WC_AF269269 | (1398) | TAGCACGCGCCCGTAGCTCAATGGTAGAGCTGTAGCC    | (SEQ ID 139) |
| Consensus | (1501) | TAGCACGCGCCCGTAGCTCAATGGTAGAGCTGTAGCC    | (SEQ ID 140) |

Figure 4 – continued (11)

```
Major outer membrane protein (MOMP) sequences
                                           1                                                                                   75
       OmpA_Ctra_NC000117_CT681     (1) ---------------------------MKKLLKSVLVFAALS-SASSLQALPVGNPAEPSLMIDGILWEGFGGDPCDPCA
       OmpA_Cmur_AE002160_TC0052    (1) ---------------------------MKKLLKSVLAFAVLG-SASSLHALPVGNPAEPSLMIDGILWEGFGGDPCDPCT
       OmpA_Cppn_NC000922_CPn0695   (1) ---------------------------MKKLLKSALLSAAFAGSVGSLQALPVGNPSDPSLLIDGTIWEGAAGDPCDPCA
       OmpA_Cpfel_NC007899_CF0958   (1) ---------------------------MKKLLKSALLFAAAG-SALSLQALPVGNPAEPSLLIDGTMWEGASGDPCDPCA
       OmpA_Cpcav_AE015925_CCA00047 (1) ---------------------------MKKLLKSALLFATTG-SALSLQALPVGNPAEPSLLIDGTMWEGASGDPCDPCS
       OmpA_Cpabo_NC004552_CAB048   (1) ---------------------------MKKLLKSALLFAATG-SALSLQALPVGNPAEPSLLIDGTMWEGASGDPCDPCS
       OmpA_84-2334_AJ310735        (1) ---------------------------MKKLLKSALLFAATG-SALSLQALPVGNPAEPSLLIDGTMWEGASGDPCDPCA
       OmpA_6BC_M73035              (1) RRAN-NSEHKKKRY-A-SLEVSMKKLLKSALLFAATG-SALSLQALPVGNPAEPSLLIDGTMWEGASGDPCDPCA
       OmpA_CP3_AF269265            (1) ---------------------------MKKLLKSALLFAATG-SALSLQALPVGNPAEPSLLIDGTMWEGASGDPCDPCA
       OmpA_GD_AF269261             (1) ---------------------------MKKLLKSALLFAATG-SALSLQALPVGNPAEPSLLIDGTMWEGASGDPCDPCS
       OmpA_NJ1_AF269266            (1) -------------------------KLLKSALLFAATG-SALSLQALPVGNPAEPSLLIDGTMWEGASGDPCDPCA
       PCR_Omp1_D_92/1293           (1) ---------------------------MKKLLKSALLFAATG-SALSLQALPVGNPAEPSLLIDGTMWEGASGDPCDPCA
OmpA_MN-VR122-Cal10_AF269262        (1) ---------------------------------------QALPVGNPAEPSLLIDGTMWEGASGDPCDPCA
       OmpA_VS225_AF269259          (1) -------------------------LLKSALLFAATG-SALSLQALPVGNPAEPSLLIDGTMWEGASGDPCDPCA
       OmpA_wSRTE30_AY762613        (1) ---------------------------MKKLLKSALLFAATG-SALSLQALPVGNPAEPSLLIDGTMWEGASGDPCDPCA
       OmpA_M56_AF269268            (1) -----------------------------KSALLFAATG-SALSLQALPVGNPAEPSLLIDGTMWEGASGDPCDPCS
       OmpA_WC_AF269269             (1) ---------------------------MKKLLKSALLFAATG-SALSLQALPVGNPAEPSLLIDGTMWEGASGDPCDPCA
                        Consensus       (1)                                 SALSLQALPVGNPAEPSLLIDGTMWEGASGDPCDPCA 76                                                                                150
       OmpA_Ctra_NC000117_CT681     (53) TWCDAISMRVGYYGDFVFDRVLKTDVNKEFQ--MGAKPTTDTG---NSAAPSTLTARENPAYGRHMQDAEMFTNAAC
       OmpA_Cmur_AE002160_TC0052    (53) TWCDAISLRLGYYGDFVFDRVLKTDVNKQFE--MGAAPTGDAD---LTTAPTPASR-ENPAYGKHMQDAEMFTNAAY
       OmpA_Cppn_NC000922_CPn0695   (54) TWCDAISLRAGFYGDYVFDRILKVDVNKTFS--MGAKPTGSA----AANYTTAVDRPNPAYNKHLHDAEWFTNAGF
       OmpA_Cpfel_NC007899_CF0958   (53) TWCDAISIRAGFYGDYVFDRILKVDVNKTISGMAAAPTAASGTASNTTV--AADRSNFAYGKHLQDAEWCTNAAY
       OmpA_Cpcav_AE015925_CCA00047 (53) TWCDAISIRAGYYGDYVFDRILKVDVNKTIS--MGTAPTGNA----AADFKTVADRNNIAYGKHMQDAEWSTNAAF
       OmpA_Cpabo_NC004552_CAB048   (53) TWCDAISIRAGYYGDYVFDRVLKVDVNKTITGMGAVPTGTA-----AANYKTPTDRPNIAYGKHLQDAEWFTNAAF
       OmpA_84-2334_AJ310735        (72) TWCDAISIRAGYYGDYVFDRVLKVDVNKTFTGMGAVPTGNS-----AADFKTPTDRANIAYGKHLQDAEWFTNAAF
       OmpA_6BC_M73035              (53) TWCDAISIRAGYYGDYVFDRVLKVDVNKTFSGMAATPTQATGNASNTNQPEANCRPNIAYGRHMQDAEWFSNAAF
       OmpA_CP3_AF269265            (53) TWCDAISIRAGYYGDYVFDRVLKVDVNKTFSGMAATPTQATGNASNTNQPEANCRPNIAYGRHMQDAEWFSNAAF
       OmpA_GD_AF269261             (53) TWCDAISIRAGYYGDYVFDRVLKVDVNKTFSGIGKKPTGSS----PNDFKNAEDRPNVAYGRHLQDSEWFTNAAF
       OmpA_NJ1_AF269266            (51) TWCDAISIRAGYYGDYVFDRVLKVDVNKTFSGMAKSPTEATGTASATTT--AVDRTNLAYGKHLQDAEWFTNAAF
       PCR_Omp1_D_92/1293           (53) TWCDAISIRAGYYGDYVFDRVLKVDVNKTFSGMAKSPTEATGTASATTT--AVDRTNLAYGKHLQDAEWFTNAAF
OmpA_MN-VR122-Cal10_AF269262       (33) TWCDAISIRAGYYGDYVFDRVLKVDVNKTFSGMAATPTQATGNASNTNQPEANCRPNIAYGRHMQDAEWFSNAAF
       OmpA_VS225_AF269259          (50) TWCDAISIRAGYYGDYVFDRVLKVDVNKTFSGMAATPTQATGNAASPTGSA---AADYKTPTDRPNIAYGRHMQDAEWFTNAAF
       OmpA_wSRTE30_AY762613        (53) TWCDAISIRAGYYGDYVFDRVLKVDVNKTFSGMAATPTQATGNASNTNQPEANGRPNIAYGRHMQDAEWFSNAAF
       OmpA_M56_AF269268            (53) TWCDAISIRAGYYGDYVFDRVLKVDVNKTFTGMAATPTEASGNATNTGTPEANCRANIAYGRHMQDAEWFSNAAF
       OmpA_WC_AF269269             (48) TWCDAISIRAGYYGDYVFDRVLKVDVNKTFSGMAAIPTESSGTVSSAKQ--AVDRVNLAYGKHLQDAEWFTNSAF
                        Consensus      (76) TWCDAISIRAGYYGDYVFDRVLKVDVNKTFSGMAA  PT   ATG   ASAT    A  DR  NIAYGKHLQDAEWFTNAAF
```

Figure 4 – continued (12)

```
                                           151                                                                              225
OmpA_Ctra_NC000117_CT681    (125) MALNIWDRFDVFCTLGATSGYLKGNSASFNLVGLLFGDNENQ--KTVKAESVPNMSFDQSVVELYTDTTFAWSVGA
OmpA_Cmur_AE002160_TC0052   (124) LALNIWDRFDVFCTLGATSGYLKGNSAAFNLVGLLFGRDET----AVAADDIPNVSLSQAVVELYTDTAFAWSVGA
OmpA_Cppn_NC000922_CPn0695  (124) LALNIWDRFDVFCTLGASNGYIRGNSTAFNLVGLFGVKG-----TTVNANELPNVSLSNGVVELYTDTSFSWSVGA
OmpA_Cpfel_NC007899_CF0958  (126) LALNIWDRFDVFCTLGASNGYFKASSDAFNLVGLIGLAG-----TDFANQRPNVEISQGIVELYTDTAFSWSVGA
OmpA_Cpcav_AE015925_CCA00047(123) LALNIWDRFDIFCTLGASNGYLKANAAAFNLVGLLGVTG-----TDLQGQYPNVAISQGLVELYTDTTFSWSVGA
OmpA_Cpabo_NC004552_CAB048  (124) LALNIWDRFDIFCTLGASNGYFKASSAAFNLVGLIGVKGS----SIAADQLPNVGITQGIVEFYTDTTFSWSVGA
OmpA_84-2334_AJ310735       (124) LALNIWDRFDIFCTLGASNGYFKASSAAFNLVGLIGIKGN----TLTNDRLPNVGITQGVVEFYTDTTFSWSVGA
OmpA_6BC_M73035             (147) LALNIWDRFDIFCTLGASNGYFKSSSAAFNLVGLIGFSAASSISTDLPMQLPNVGITQGVVEFYTDTSFSWSVGA
OmpA_CP3_AF269265           (128) LALNIWDRFDIFCTLGASNGYFKASSAAFNLVGLIGFSATNSTSTDLPMQLPNVGITQGVVEFYTDTFSWSVGA
OmpA_GD_AF269261            (124) LALNIWDRFDIFCTLGASNGYFKASSAAFNLVGLIGVKGS----SLTNDQLPNVAITQGVVEFYTDTTFSWSVGA
OmpA_NJ1_AF269266           (124) LALNIWDRFDIFCTLGASNGYFKASSAAFNLVGLIGLKG-----TDFNNQLPNVAITQGVVEFYTDTTFSWSVGA
PCR Omp1 D 92/1293          (126) LALNIWDRFDIFCTLGASNGYFKASSAAFNLVGLIGLKG-----TDFNNQLPNVAITQGVVEFYTDTSFSWSVGA
OmpA_MN-VR122-Call0_AF269262(108) LALNIWDRFDIFCTLGASNGYFKSSSAAFNLVGLIGFSATSSTSTELPMQLPNVGITQGVVEFYTDTSFSWSVGA
OmpA_VS225_AF269259         (121) LALNIWDRFDIFCTLGASNGYFKASSAAFNLVGLIGVKGT----SVAADQLPNVGITQGIVEFYTDTSFSWSVGA
OmpA_WSRTE30_AY762613       (128) LALNIWDRFDIFCTLGASNGYFKGSSAAFNLVGLIGFSASSAVSTDLPKQLPNVAITQGVVEFYTDTSFSWSVGA
OmpA_M56_AF269268           (121) LALNIWDRFDIFCTLGASNGYFKASSAAFNLVGLLFGIAGN-SESNALNDQLPNVAITQGIVEFYTDTTFSWSVGA
OmpA_WC_AF269269            (151) LALNIWDRFDIFCTLGASNGYFKASSAAFNLVGLIGV  G     TD   QLPNVAITQGVVEFYTDTTFSWSVGA
Consensus                                                                                                                 300

226
OmpA_Ctra_NC000117_CT681    (198) RAALWECGCATLGASFQYAQSKPKVEELNVLCNAAEFTINKPKGYVGK--EFPLDLTAGTDAATGTKDASIDYHE
OmpA_Cmur_AE002160_TC0052   (195) RAALWECGCATLGASFQYAQSKPKVEELNVLCNAAEFTINKPKGYVGQ--EFPLNIKAGTVSATDTKDASIDYHE
OmpA_Cppn_NC000922_CPn0695  (195) RGALWECGCATLGAEFQYAQSKPKVEELNVICNVSQFSVNKPKGYKGVA--FPLPTDAGVATATGTKSATINYHE
OmpA_Cpfel_NC007899_CF0958  (196) RGALWECGCATLGAEFQYAQSNPKIEMLNVTSSPAQFMIHKPRGYKGTAANFPLPVAAGTATATDTKSATVKYHE
OmpA_Cpcav_AE015925_CCA00047(193) RGALWECGCATLGAEFQYAQSNPKIEMLNVISSPTQFVIHKPRGYKGTAANFPLPLTAGTESATDTKSATIKYHE
OmpA_Cpabo_NC004552_CAB048  (195) RGALWECGCATLGAEFQYAQSNPKIEMLNVVSSPAQFVVHKPRGYKGT--AFPLPLTAGTDQATDTKSATIKYHE
OmpA_84-2334_AJ310735       (195) RGALWECGCATLGAEFQYAQSNPKIEMLNVTFSPAQFVVHKPRGYKGATANFSLPETTGSDAATDTKSATLKYHE
OmpA_6BC_M73035             (222) RGALWECGCATLGAEFQYAQSNPKIELLNVTSSPAQFVIHKPRGYKGASSNFPLPITAGTTEATDTKSATIKYHE
OmpA_CP3_AF269265           (203) RGALWECGCATLGAEFQYAQSNPKIEMLNVISSPAQFVVHKPRGYKGTSANFPLPITAGTEATDTKSATLKYHE
OmpA_GD_AF269261            (195) RGALWECGCATLGAEFQYAQSNPKIEMLNVTSSPAQFVVHKPRGYKGTSANFPLPANAGTEATDTKSATLKYHE
OmpA_NJ1_AF269266           (194) RGALWECGCATLGAEFQYAQSNPKIEMLNVTSSPAQFVIHKPRGYKGSNFPLPIDAGTEAATDTKSATLKYHE
PCR Omp1 D 92/1293          (196) RGALWECGCATLGAEFQYAQSNPKIEMLNVTSSPAQFVIHKPRGYKGSNFPLPIDAGTEAATDTKSATIKYHE
OmpA_MN-VR122-Call0_AF269262(183) RGALWECGCATLGAEFQYAQSNPKIEVLNVTSSPAQFVIHKPRGYKGASSNFPLPITAGTEATDTKSATIKYHE
OmpA_VS225_AF269259         (192) RGALWECGCATLGAEFQYAQSNPKIEVLNVTSSPAQFVIHKPRGYKGTSNFPLPLTAGTDGATDTKSATLKYHE
OmpA_WSRTE30_AY762613       (203) RGALWECGCATLGAEFQYAQSNRKIEMLNVTSSPAQFVIHKPRGYKGTSSNFPLPITAGTTEATDTKSATIKYHE
OmpA_M56_AF269268           (195) RGALWECGCATLGAEFQYAQSNPKIEMLNVTSSPAQFVIHKPRGYKGTSNFPLPITAGTDDATDTKSATIKYHE
OmpA_WC_AF269269            (226) RGALWECGCATLGAEFQYAQSNPKIEMLNVTSSPAQFVIHKPRGYKGTSSNFPLPITAGTDTATDTKSATIKYHE
Consensus                         RGALWECGCATLGAEFQYAQSNPKIEMLNVTSSPAQFVIHKPRGYKGTSSNFPLPITAGTD ATDTKSATIKYHE
```

Figure 4 – continued (13)

Figure 4 – continued (14)

```
                                            451                                                        507
OmpA_Ctra_NC000117_CT681       (394) ------------------------------------------------------     (SEQ ID 141)
OmpA_Cmur_AE002160_TC0052      (388) ------------------------------------------------------     (SEQ ID 142)
OmpA_Cppn_NC000922_CPn0695     (390) ------------------------------------------------------     (SEQ ID 143)
OmpA_Cpfel_NC007899_CF0958     (393) ------------------------------------------------------     (SEQ ID 144)
OmpA_Cpcav_AE015925_CCA00047   (390) ------------------------------------------------------     (SEQ ID 145)
OmpA_Cpabo_NC004552_CAB048     (390) ------------------------------------------------------     (SEQ ID 146)
OmpA_84-2334_AJ310735          (364) ------------------------------------------------------     (SEQ ID 147)
OmpA_6BC_M73035                (426) ------------------------------------------------------     (SEQ ID 148)
OmpA_CP3_AF269265              (426) LLPPFSEFQISFLKSVRIRIH-LSKIF-KLET-RLQSCVKSIIKLSLYS-HAPV-     (SEQ ID 149)
OmpA_GD_AF269261               (415) LLTSFCIA-YLFFKIHSHKNSLII-NFLEA-NLEITTLRKKHY-TNISILSTRPYSM (SEQ ID 150)
OmpA_NJ1_AF269266              (391) ------------------------------------------------------     (SEQ ID 151)
PCR_Omp1_D_92/1293             (357) ------------------------------------------------------     (SEQ ID 152)
OmpA_MN-VR122-Cal10_AF269262   (383) ------------------------------------------------------     (SEQ ID 153)
OmpA_VS225_AF269259            (389) ------------------------------------------------------     (SEQ ID 154)
OmpA_WSRTE30_AY762613          (367) ------------------------------------------------------     (SEQ ID 155)
OmpA_M56_AF269268              (403) ------------------------------------------------------     (SEQ ID 156)
OmpA_WC_AF269269               (392) ------------------------------------------------------     (SEQ ID 157)
Consensus                      (451) ------------------------------------------------------     (SEQ ID 158)
```

Figure 5:
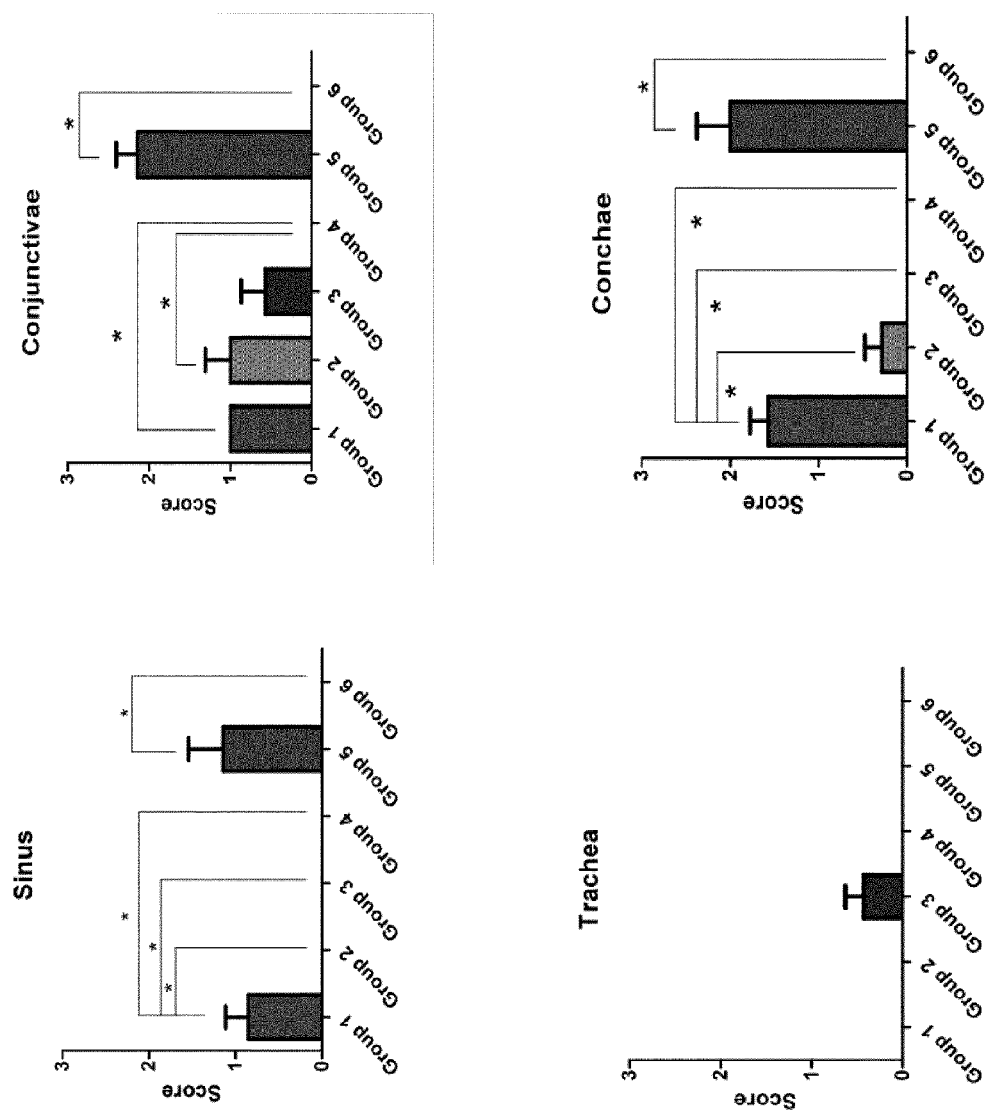

Figure 5 – continued (1)
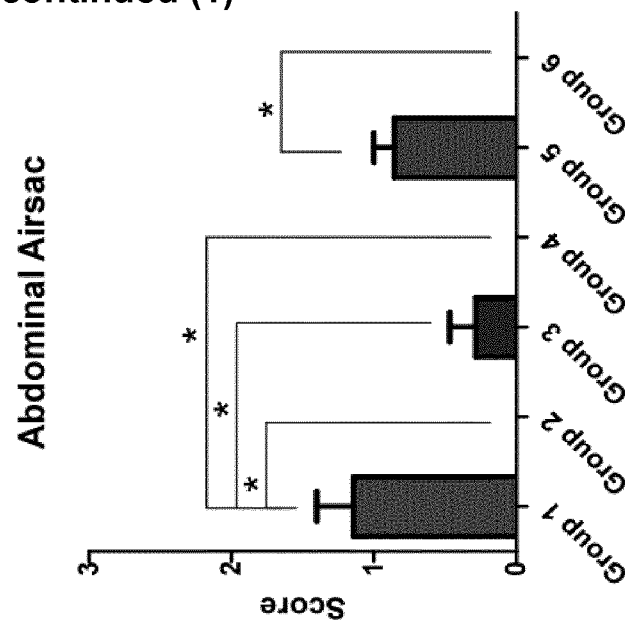
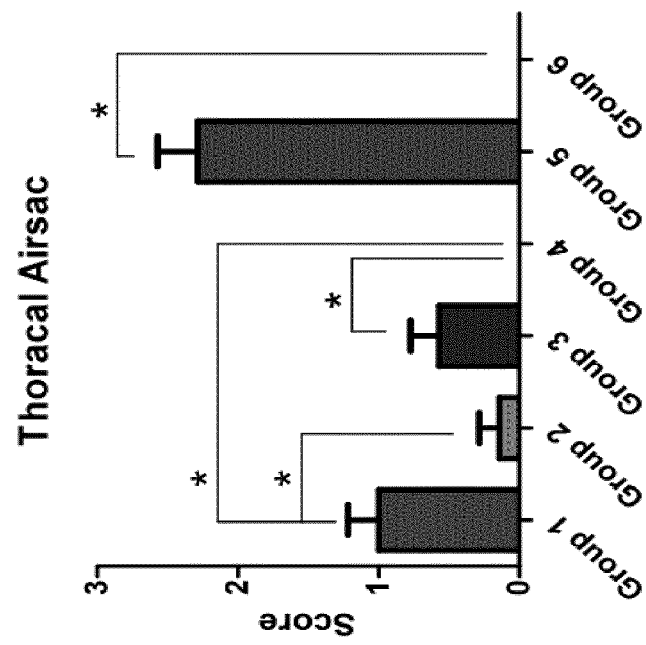

Figure 5 – continued (2)
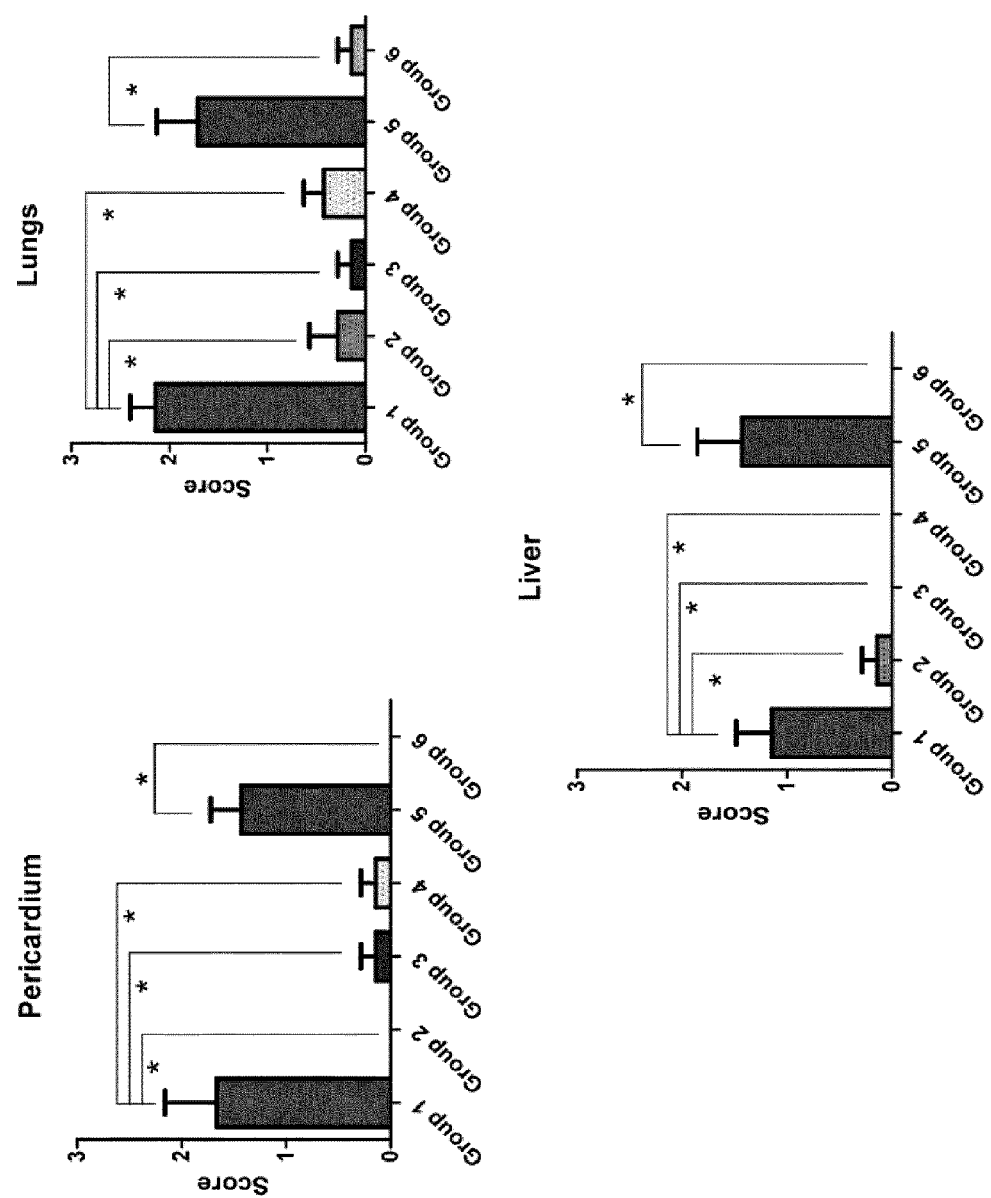

Figure 6

Figure 7

VACCINES FOR *CHLAMYDIA*

FIELD OF THE INVENTION

The present invention relates to means and methods to protect against disease caused by bacteria belonging to the genus *Chlamydia*. In particular, the present invention relates to isolated B- and T-cell epitopes derived from the major outer membrane protein of *Chlamydia psittaci* which can be used against an infection with a species of the genus *Chlamydia*. More in particular, the invention provides a vaccine which can be used against chlamydiosis caused by *Chlamydia psittaci* in birds and man. In addition, the invention relates to a diagnostic method to diagnose the latter infections.

BACKGROUND ART

The genus *Chlamydia* comprises the species *Chlamydia abortus, Chlamydia pneumoniae, Chlamydia psittaci, Chlamydia pecorum, Chlamydia felis,* and *Chlamydia caviae.* Diseases caused by bacteria belonging to the genus *Chlamydia* are the following. *Chlamydia pneumoniae* causes acute or chronic bronchitis and pneumonia in humans and in some cases otitis media, obstructive pulmonary disease and pulmonary exacerbation of cystic fibrosis. It has also been associated with Alzheimer's disease, atherosclerosis, asthma, erythema nodosum, reactive airway disease, Reiter's syndrome and sarcoidosis in humans. Morever, *Chlamydia pneumoniae* causes respiratory disease in koalas. *Chlamydia pecorum* strains characterized so far have been limited to mammals, but not to a specific host family. They are serologically and pathologically diverse. The organism has been isolated from ruminants, a marsupial and swine. In koalas, *C. pecorum* causes reproductive disease, infertility and urinary tract disease. It has been a major threat to the Australian koala population. In other animals *C. pecorum* causes abortion, conjunctivitis, encephalomyelitis, enteritis, pneumonia and polyarthritis. *Chlamydia felis* is endemic among house cats worldwide. It causes primarily conjunctivitis and rhinitis. *Chlamydia caviae* comprises five known isolates, all isolated from guinea pigs. The natural infection site is the mucosal epithelium of the conjunctiva where a non-invasive infection is established. However, it is possible to infect the genital tract of guinea pigs eliciting a disease that is very similar to human genital infection. *Chlamydia abortus* strains are endemic among ruminants and efficiently colonize the placenta. *Chlamydia abortus* is the most common infectious cause of abortion in sheep, where the disease is known as ovine enzootic abortion (OEA) or enzootic abortion of ewes (EAE) in countries of Northern, Central and Western Europe. Enzootic abortion in goats is similar in severity to that occurring in sheep, although the spread and economical impact across Europe is less clear because of the lack of epidemiological data. The disease can also affect cattle, swine and horses but this is thought to occur to a much lesser extent. Sporadic zoonotic abortion due to *C. abortus* has been confirmed by analysis of isolates from women who work with sheep and goats. *Chlamydia psittaci* produces avian respiratory infections and is a serious threat to industrial poultry production. Additionally, it causes epizootic outbreaks in mammals and respiratory psittacosis or parrot fever in humans.

Protective immunity to Chlamydiaceae (Including the genus *Chlamydia*) that is observed in animals previously exposed to the pathogen is believed to be effected primarily through the action of CD4+ T helper type 1 (Th1) lymphocytes, CD8+ T lymphocytes, mononuclear phagocytes, and cytokines secreted by these cells (Cotter et al., 1995; Su and Caldwell, 1995; Beatty et al., 1997; Cotter et al., 1997; Johansson et al., 1997; Su et al., 1997; Wiliams et al., 1997; reviewed by Kelly et al., 2003).

Initial attempts to develop an effective vaccine for controlling both animal and human chlamydial infections began with the use of inactivated or live whole organism preparations in the 1950s, e.g. for *C. abortus* in sheep. In general, such preparations offered a reasonable level of protection, although they have been more successful in protecting animal infections than human infections (Vanrompay et al., 2005).

During the 1960s unsuccessful attempts were made to develop inactivated and live vaccines against *C. trachomatis* using both human and non-human primates. These vaccines reduced disease in some individuals but they enhanced disease in others resulting from stimulation of enhanced delayed-type hypersensitivity (DTH) response. Therefore, the use of whole organisms for developing human chlamydial vaccines was essentially abandoned.

In the early 1980s an attenuated strain of *C. abortus* was developed as a live vaccine and is one of the 5 commercially available vaccines in Europe and the USA, the other four being inactivated whole organism based vaccines (Longbottom and Livingstone, 2006). These commercial live-attenuated and inactivated vaccines offer good protection against OEA and significantly reduce the shedding of infective organisms, a factor important in limiting the spread of infection to other animals. However, concerns remain over the safety of using live-attenuated vaccines. There may also be a risk of the attenuated strain reverting to virulence, thus having the potential to cause disease and abortion in the vaccinated animal. Furthermore, the vaccine cannot be administered during pregnancy or to animals being treated with antibiotics limiting its use. In contrast, the inactivated vaccines can be administered to pregnant ewes, although care must be taken in handling and administering these vaccines as they are adjuvanted with mineral oils, which have the potential to cause tissue necrosis if accidentally self-injected. The only other animal chlamydial vaccines, which are commercially available are for *C. felis* infection in cats (Longbottom and Livingstone, 2006). Although vaccination is successful in reducing acute disease, it does not, however, prevent shedding of the organism and therefore chlamydial spreading in the population nor does it prevent re-infection. Following the identification of the major outer membrane protein (MOMP) as a structurally and immunologically dominant protein vaccine research largely focused on this protein. A certain level of protection has been achieved with COMC (chlamydial outer membrane complex) preparations, in which MOMP constitutes 90% or more of the protein content, using the guinea pig and mouse models for *C. trachomatis* genital tract infection, and in a mouse toxicity test for *C. felis* infection (Sandbulte et al., 1996; Pal et al., 1997). Studies on MOMP of *C. psittaci* were performed e.g. by Tan et al., 1990, Sandbulte et al., 1996 and Verminnen et al., 2005.

DNA vaccination, mimicking a live vaccine, creates protective CD4+ as well as CD8+ responses but antibody responses are low (Verminnen et al., 2010). Moreover DNA vaccines are still too expensive (especially for poultry) and the public is not (yet) ready to consume products from DNA vaccinated animals (in the case of *C. psittaci* eggs/meat).

Until now, completely safe and effective *Chlamydia* vaccines are still not available.

The present invention comprises an innovative vaccine that creates both optimal humoral and cellular immune responses by combining B cell and CD4 Th2 cell epitopes (humoral) and CD4 Th1 and CD8$^+$ cytotoxic T cell epitopes (cellular) in a vaccine. In contrast, former and current studies on *Chlamydia* vaccine development are focusing on cellular responses only (CD8 and CD4 Th1), as they are believed to be crucial to protection against this obligate intracellular pathogen (Su and Caldwell, 1995; Morrison et al., 2000). Moreover, due to the Th1/Th2 paradigm (both responsible for different types of protective responses) vaccine development against infectious agents focuses on creating either a Th1 or Th2 response (Th1 or Th2 polarized vaccines). Thus, the construction of a non-polarized vaccine, deliberately inserting Th1 as well as Th2 epitopes is highly unusual and new as Th1 and Th2 cells act differently and even opposing.

The present invention relates to selected protective B- and T- (Th1 and Th2) cell epitopes of an immunodominant protein (the major outer membrane protein or MOMP). Such protein-based vaccines can be used against an infection with a species of the genus *Chlamydia*. These peptide sequences do not cause immunopathological reactions nor immunosuppressive T cell responses. Reversion to virulence is not applicable, thus enhancing the safety for both animals and humans. The epitopes can be used in any suitable vector, preferably a vector which: a) can be used in the presence of species-specific maternal antibodies and b) allows easy and cost effective vaccine mass production. Moreover, and surprisingly, the present invention demonstrates that both the cellular- and humoral immune response are required to protect against an infection with a species of the genus *Chlamydia*.

FIGURE LEGENDS

FIG. 1: structure of the MOMP located in the bacterial membrane

Figure 2:
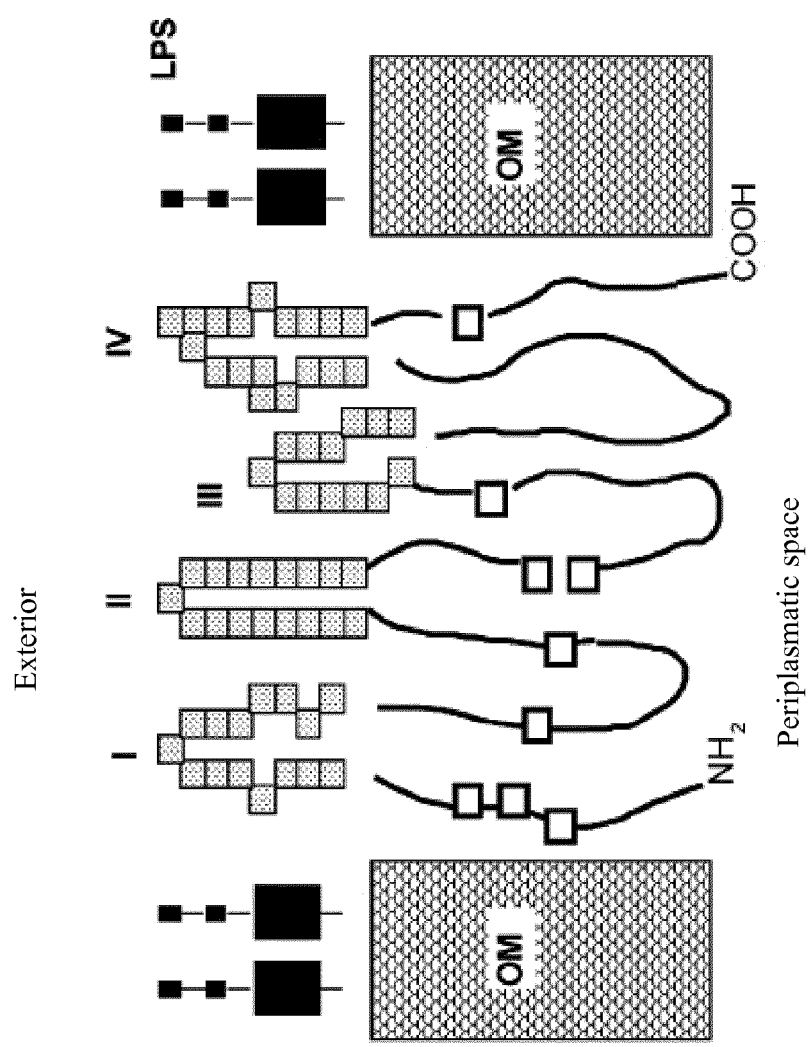

FIG. 2: detailed structure of the MOMP. Solid line, membrane-embedded peptide chain of MOMP; solid line, 5 conserved sequences; pointed squares, residues comprising the variable sequences (VSs) I, II, III and IV; open squares, conserved cysteines. The presence of lipopolysaccharide (LPS) structures (solid blocks) is indicated above the outer membrane (OM). Claimed B cell epitopes are in VSI (immunodominant), VS2 (serovar) and VS4 (imunodominant). Claimed T cell epitopes are in CS1, CS4 and VS4.

Figure 3:
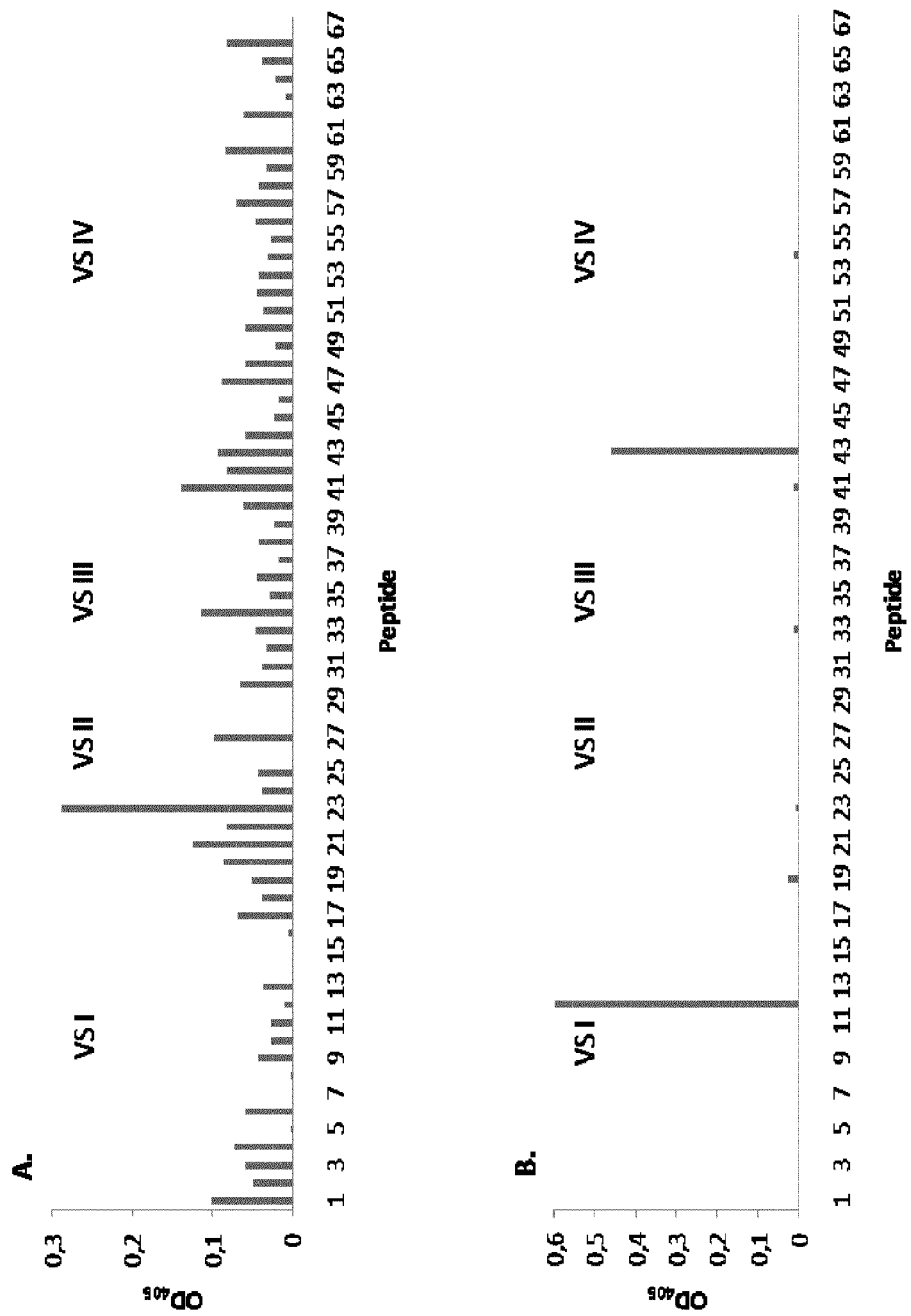

FIG. 3: (A.) B cell epitope mapping results for the *C. psittaci* serovar D strain 92/1293 MOMP using the serovar D-specific MAb NJ1 (1/100); (B.) B cell epitope mapping results for the *C. psittaci* serovar D strain 92/1293 MOMP using serum of SPF turkeys immunized with recombinant MOMP. VSI: peptides 1 to 20, VSII: peptides 21 to 32, VSIII: peptides 33-40, VSIV: peptides 41 to 67.

FIG. 4: Alignment of *Chlamydia* and *C. psittaci* ompA nucleotide sequences and MOMP amino acid sequences. Lines: 1) *Chlamydia trachomatis* (Ctra), 2) *Chlamydia muridarum* (Cmur), 3) *Chlamydia pneumoniae* (Cpn), 4) *Chlamydia felis* (Cfel), 5) *Chlamydia caviae* (Ccav), 6) *Chlamydia abortus* (Cabo). Lines 7 till 18: *Chlamydia psittaci* strains 84/2334, 6BC, CP3, GD, NJ1, 92/1293, Cal10, VS225, WSRTE30, M56 and WC. The ompA and MOMP sequence of reference strain 92/1293 used for vaccine design is underlined.

FIG. 5: Gross pathology.

Figure 6:
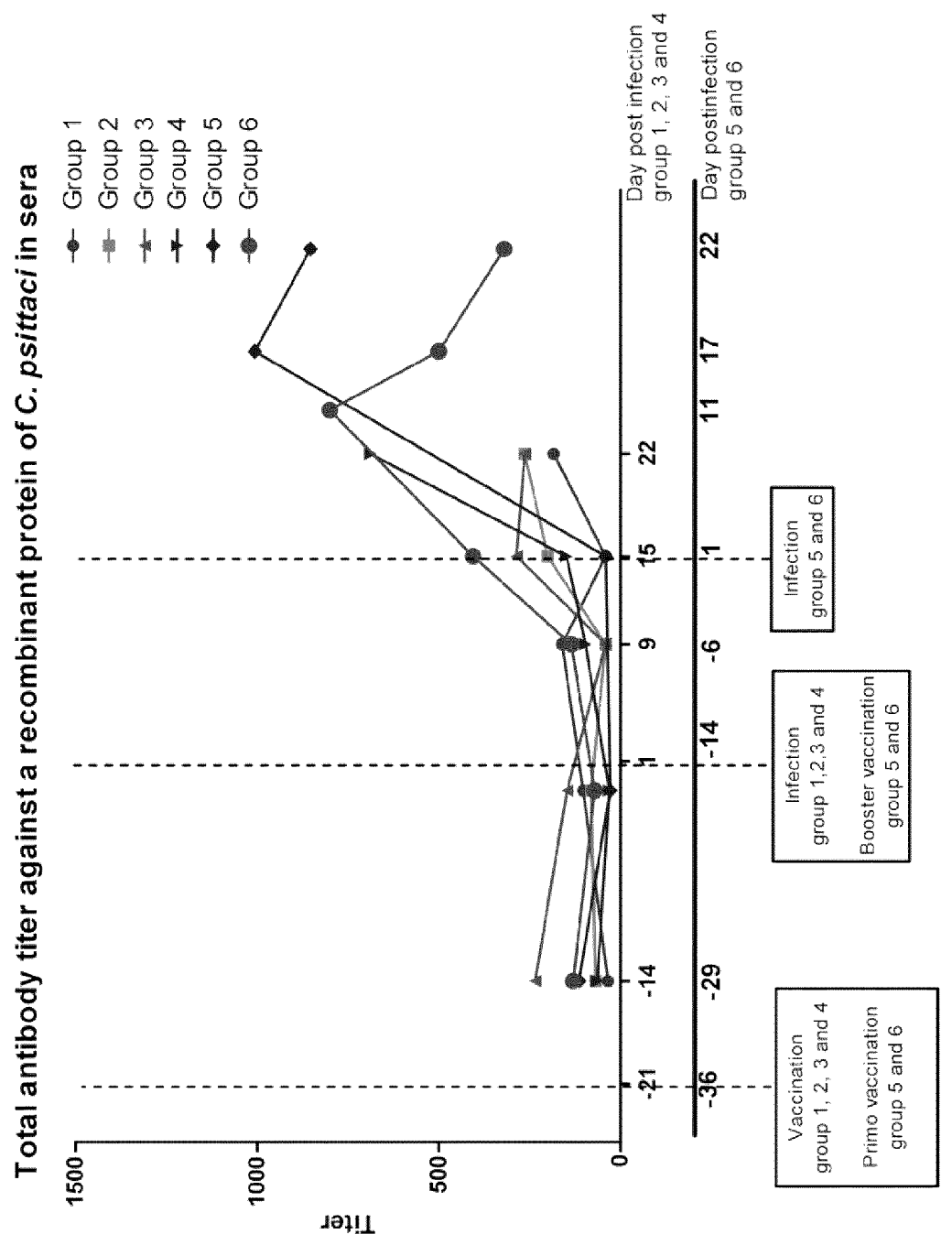

FIG. 6: Mean serum antibody titers against a recombinant protein (MOMP) of *C. psittaci*. The ELISA plates were coated with recombinant MOMP of *C. psittaci*.

Figure 7:
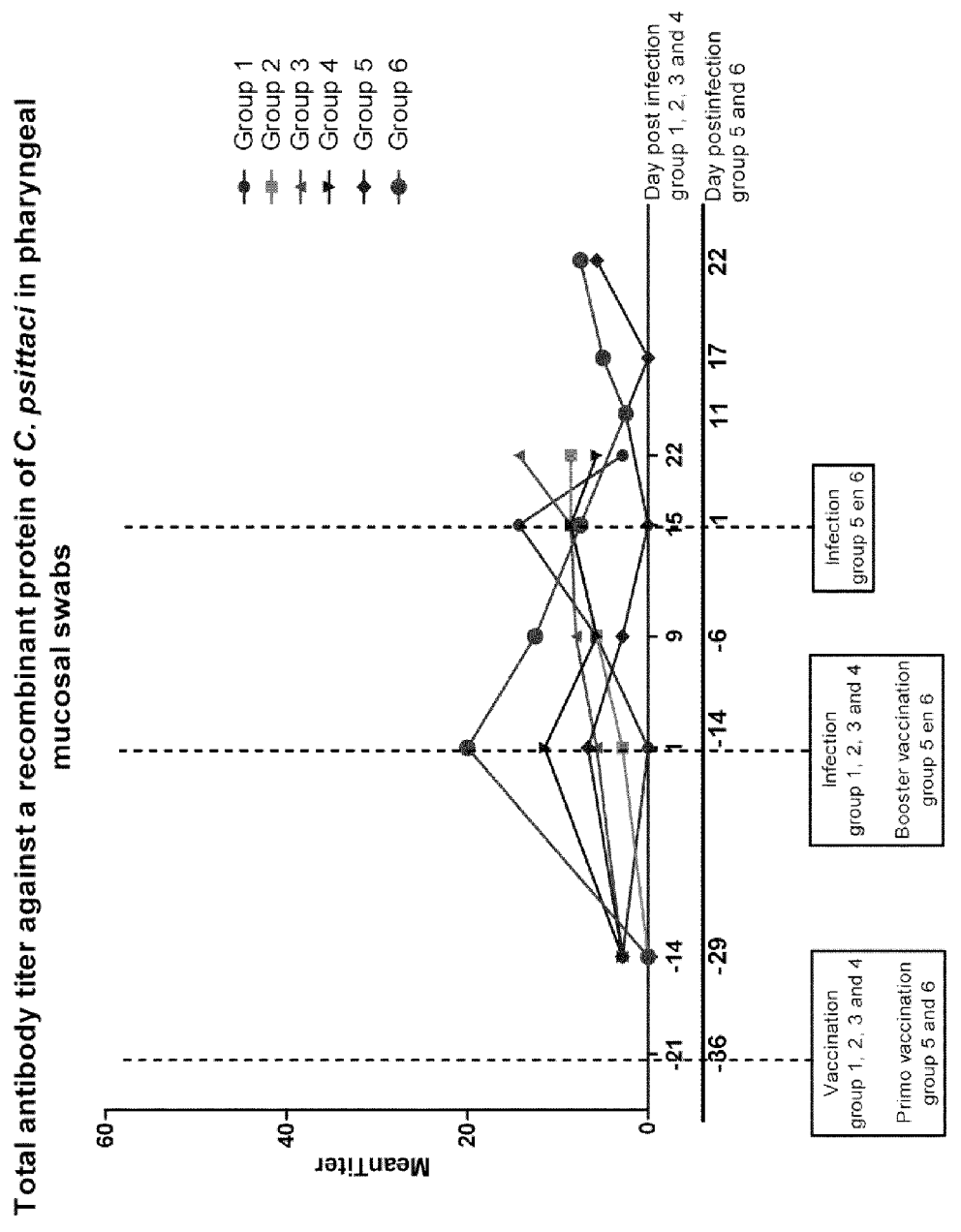

FIG. 7: Mean mucosal antibody titers against a recombinant protein (MOMP) of *C. psittaci*. The ELISA plates were coated with recombinant MOMP of *C. psittaci*.

DESCRIPTION OF THE INVENTION

The present invention relates to the use of isolated peptides comprising B- and T-cell epitopes for producing a vaccine against species of the genus *Chlamydia*, and more in particular to induce an immunoprotective response against an infection with a species of the genus *Chlamydia*.

The present invention relates to a composition comprising at least one isolated peptide comprising a B-cell epitope located in a variable amino acid region of the major outer membrane protein (MOMP) of *Chlamydia psittaci* and at least one isolated peptide comprising a T-cell epitope located in a conserved or variable amino acid region of the MOMP of *Chlamydia psittaci*. In particular, the invention relates to a composition comprising one or more peptides, each of said peptides comprising one or more epitopes selected from the list consisting of a B-cell epitope, a CD4+ Th2 cell epitope, a CD4+ Th1 cell epitope and a CTL epitope; wherein said composition comprises at least a B-cell epitope, a CD4+ Th2 cell epitope, a CD4+ Th1 cell epitope and a CTL epitope, and wherein the epitopes are located in the major outer membrane protein (MOMP) of *Chlamydia psittaci* and wherein the composition does not comprise the full-length *Chlamydia* MOMP protein.

The composition is specifically designed to induce an immunoprotective response against an infection with a species of the genus *Chlamydia*. In particular, the combination of the B- and T-cell epitope containing peptides is not equal to the complete or full-length MOMP protein, in particular the *Chlamydia psittaci* MOMP protein. More particular, the B-cell epitope is located in the variable region I, II or IV and the T-cell epitope (including CD8+, CD4+ Th1, and CD4+ Th2 cell epitopes) is located in the conserved region I or IV, or in variable region IV. The MOMP protein of *Chlamydia psittaci* is described by Vanrompay et al., 1998 (p 5496 FIG. 1, variable domains are indicated).

With the term "B cell-epitope" is meant a part of an antigen that induces antibody production upon recognition by the host's immune system.

A "T-cell epitope" is a part of an antigen that induces a CD4+ Th1 (T helper, HTL), CD4+ Th2 (T helper, HTL) or CD8+ cell (cytotoxic, CTL) response upon recognition by the host's immune system. T helper (Th) cells are considered major players in the response against infectious organisms. To convey their full function, Th cells secrete a variety of cytokines, which define their distinct actions in immunity. Th cells can be subdivided into three different types based on their cytokine signature, Th1, Th2 and Th17 cells. "Th1 cells" secrete IFN-gamma (pro-inflammatory cytokine), which is the main macrophage-activating cytokine and TNF-β, which also activates macrophages, inhibits B cells and is directly cytotoxic for some cells. Th1 cells allow the production of $IgG_{2a}$ antibodies in mice and of IgM, IgA, $IgG_1$, $IgG_2$ and $IgG_3$ antibodies in humans. "Th2 cells" secrete IL-4, IL-5, IL-6, IL-9 and IL-13 all of which activate B cells, and IL10 (important anti-inflammatory cytokine), which inhibits macrophage activation. Th2 cells induce $IgG_1$ and IgE antibodies in mice and IgM, $IgG_4$ and IgE in humans. Th17 cells secrete the pro-inflammatory cytokine IL-17 (Murphy et al., 2008; Annunziato and Romagnani, 2009).

A peptide comprising a CTL epitope (CD8+) usually consists of 13 or less amino acid residues in length, 12 or less amino acids in length, or 11 or less amino acids in length, preferably from 8 to 13 amino acids in length, most preferably from 8 to 11 amino acids in length (i.e. 8, 9, 10, or 11). A peptide comprising a HTL epitope (CD4+) consists of 50 or less amino acid residues in length, and usually from 6 to 30 residues, more usually from 12 to 25, and preferably consists of 12 to 20 (i.e. 12, 13, 14, 15, 16, 17, 18, 19, or 20) amino acids in length. Peptides comprising B cell epitopes do not have a defined length and can vary from 5 to 30 amino acids in length, preferably from 5 to 15 amino acids in length, i.e. 5, 6, 7, 8, 9, 10, 11, 12, 13, 14, or 15 amino acids.

In a specific embodiment, a peptide comprising a T cell epitope has a length of 6 to 50 amino acids and a peptide comprising a B cell epitope has a length of 5 to 30 amino acids.

Hence, it is to be understood that peptides with a defined length and comprising the epitopes specified herein are part of the present invention and can be used in the compositions and methods as described herein. In a specific embodiment, the peptides are immunogenic peptides, i.e. peptides capable of eliciting an immune response in an organism, including a cellular and/or humoral response. More particular, the present invention comprises an innovative vaccine that creates both humoral and cellular immune responses by combining B cell and CD4 Th2 cell epitopes (humoral) and CD4 Th1 and CD8$^+$ cytotoxic T cell epitopes (cellular) in a composition.

The term "isolated" is used to indicate that a cell, peptide or nucleic acid is separated from its native environment. Isolated peptides and nucleic acids may be substantially pure, i.e. essentially free of other substances with which they may bound in nature.

With the term 'induction of an immunoprotective response' is meant a (humoral and/or cellular) immune response that reduces or eliminates one or more of the symptoms of disease, i.e. clinical signs, lesions, bacterial excretion and bacterial replication in tissues in the infected subject compared to a healthy control. Preferably said reduction in symptoms is statistically significant when compared to a control.

Infections with a species of the genus *Chlamydia* are infections with one or more of the species selected from the group consisting of: *Chlamydia abortus, Chlamydia pneumoniae, Chlamydia psittaci, Chlamydia pecorum, Chlamydia felis*, and *Chlamydia caviae.*

In a particular embodiment, the present invention provides peptides suitable for vaccine design. Suitable peptides comprising T-cell epitopes correspond to SEQ ID NO 1, 7, 8, 9, 10, 11, 12, 13, 18, 20, 21, 22, 24, 25, 26, 27, 29, 30, 31, 32, 35, 41, 42, 43, 44, 46, 49, 50, 51, 53, 54, 55, 56, 60, 61, 63, 64, 65, 66, 67, 68, 69, 70, 71, 72, 73, 74, 75, 76, 77, 78, 79, 80, 81, 82, 84, 85, 86, 87, and 91. As can be derived from the data in Table 1, said peptides are characterized as follows:

- Peptides comprising a CTL (CD8+) epitope correspond to SEQ ID NO 20, 26, 27, 42, 43, 61, 73, 75, and 80.
- Peptides comprising a CD4+ Th1 cell epitope correspond to SEQ ID NO 1, 10-13, 18, 20, 25, 27, 29, 31-32, 35, 42, 46, 51, 53-56, 61, 64-67, 69-73, 75, 79-81, and 87.
- Peptides comprising a CD4+ Th2 cell epitope correspond to SEQ ID NO 7, 8, 43, 76, 77, 85, and 91.

In addition, peptides comprising a B-cell epitope correspond to SEQ ID NO 32-33, 45-46 and 90-96.

The composition of the present invention preferably comprises specific combinations of said peptides thereby inducing a humoral as well as a cellular immune response. The composition therefore comprises one or more peptide(s) comprising at least one B cell epitope, at least one CD4 Th2 cell epitope, at least one CD4 Th1 cell epitope and at least one $CD8^+$ cytotoxic T cell epitope.

More specifically, the present invention relates to the composition as indicated above, wherein said isolated B cell epitope consists of the amino acid sequence GTASATT (SEQ ID NO 92), GTDFNN (SEQ ID NO 93) or NPTLLGKA (SEQ ID NO 94), or variants thereof, which are located in the variable domain (VS) I, II and IV, respectively of the MOMP of *Chlamydia psittaci* serovar D strain 921/1293, and, wherein said isolated T-cell epitope consists of the amino acid sequence
selected from the group consisting of:

```
DGTMWEGAS          (SEQ ID NO 101; CD4Th2);
ASGDPCDPC          (SEQ ID NO 102; CD4Th1);
ATDTKSATLKYHE      (SEQ ID NO 103; CD4Th1);
SATLKYHEWQVGL      (SEQ ID NO 104; CD4Th1);
SATLKYHEWQVGLAL    (SEQ ID NO 105; CD4Th1);
TLKYHEWQVGLAL      (SEQ ID NO 106; CD4Th1 and CD8
                   (CTL));
KYHEWQVGLALSY      (SEQ ID NO 107; CD4Th1 and CD8
                   (CTL));
YHEWQVGLALSYR      (SEQ ID NO 108; CD4Th2);
HEWQVGLALSYRL      (SEQ ID NO 109; CD4Th2);
QVGLALSYRLNM       (SEQ ID NO 110; CD4Th2);
RLNMLVPYIGVNW      (SEQ ID NO 111; CD4Th1);
RLNMLVPYIGVNWS     (SEQ ID NO 112; CD4Th1 and CD8
                   (CTL));
NMLVPYIGVNWSR      (SEQ ID NO 113; CD4Th1);
MLVPYIGVNWSRA      (SEQ ID NO 114; CD4Th1);
YIGVNWSRAT         (SEQ ID NO 115; CD4Th1);
TAVLDLTTW          (SEQ ID NO 116; CD4Th2);
TTVDGTNTYSDFL      (SEQ ID NO 117; CD4Th2);
and
TWCDAISIRAGYYGD    (SEQ ID NO 20; CD4Th1 and CD8
                   (CTL));
``` or variants thereof, which are located in the conserved region I or IV, or in the variable domain IV, of the MOMP of *Chlamydia psittaci* serovar D strain 921/1293. Optionally, flanking amino acids or regions of the specified B- and T-cell epitopes can be part of the peptide sequences to be included in the composition.

In a specific embodiment, the invention relates to the composition and use as indicated above, wherein the peptide comprising a B-cell epitope is selected from the group consisting of:
TGTASATT (SEQ ID NO 95), KGTDFNNQ (SEQ ID NO 96) and NPTLLGKA (SEQ ID NO 94), or a variant thereof, and wherein the peptide comprising a T-cell epitope comprises or consist of an amino acid sequence selected from the group consisting of: SEQ ID NO 1, 7-13, 18, 20-22, 24-27, 29-32, 35, 41-44, 46, 49, 50, 51, 53-56, 60, 61, 63-82, 84-87, and 91, or a variant thereof. In a particular embodiment, the peptide comprising the B-cell epitope NPTLLGKA (SEQ ID NO 94) and the CD4 Th2 cell epitopes TAVLDLTTW (SEQ ID NO 116) and TTVDGTNTYSDFL (SEQ ID NO 117) is AQPKLATAVLDLTTWNPTLLGKATTVDGTNTYSDFL (SEQ ID NO 98).

In a preferred embodiment the peptide comprising a T-cell epitope is selected from the group consisting of the amino acids at position:
30-44, 35-49, 36-50, 37-51, 257-271, 262-276, 263-278, 264-279, 266-280, 267-281, 268-282, 269-283, 279-293, 280-294, 281-295, 282-296, 287-302, and 326-340 of the 356 amino acids MOMP of *Chlamydia psittaci* serovar D strain 921/1293, or variants thereof. The *Chlamydia psittaci* serovar D strain 921/1293 is described by Vanrompay et al., 1998 and in FIG. 4.

The compositions and methods of the present invention also encompass variants of the above specified peptides comprising the epitopes. "Variants" of the B and T-cell epitopes on the corresponding peptide sequences of the different strains or species are also part of the invention, i.e. those peptide sequences at corresponding amino acid positions when aligned to a reference sequence (e.g. FIG. 4 for different *Chlamydia* species and for different *C. psittaci* strains with strain 92/1293 being reference sequence). Moreover, a "variant" as used herein, is a peptide that differs from the native antigen only in conservative substitutions and/or modifications, such that the ability of the peptide to induce an immune response is retained. Peptide variants preferably exhibit at least about 70%, preferably at least about 80%, more preferably at least about 90% and most preferably at least about 95% identity to the identified peptides. Alternatively, such variants may be identified by modifying one of the above peptide sequences and evaluating the immunogenic properties of the modified peptide using, for example, the representative procedures described herein. A "conservative substitution" is one in which an amino acid is substituted for another amino acid that has similar properties, such that one skilled in the art of peptide chemistry would expect the nature of the peptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants may also (or alternatively) be peptides as described herein modified by, for example, by the deletion or addition of amino acids that have minimal influence on the immunogenic properties, secondary structure and hydropathic nature of the peptide.

The invention more specifically relates to the composition and use as indicated above, wherein said isolated B-cell epitopes and T-cell (Th2) epitopes are part of a fragment of the 356 amino acid MOMP of *Chlamydia psittaci* serovar D strain 92/1293 which is encoded by the nucleic acid sequence GCT AGC GAA CCA AGT TTA TTA ATC GAT GGC ACT ATG TGG GAA GGT GCT TCA GGA GAT CCT TGC GAT CCT TGC ACA GGA ACA GCA AGT GCT ACT ACT AAA GGA ACT GAT TTC AAT AAT CAA GCT CAG CCT AAA TTA GCC ACT GCT GTT TTA GAT TTA ACC ACT TGG AAC CCA ACA CTT TTA GGA AAG GCC ACA ACT GTC GAC GGC ACC AAT ACT TAC TCT GAC TTC TTA GGT ACC (SEQ ID NO 100), and/or, wherein said T cell (Th1) epitopes are part of the amino acid sequence corresponding to amino-acids 257-301 of the 356 amino acid MOMP of *Chlamydia psittaci* serovar D strain 92/1293.

The present invention relates, even more specifically, to the composition or use as indicated above wherein said species of the genus *Chlamydia* is *Chlamydia psittaci*. As such, the present invention relates to the prevention of morbidity or mortality, or to treatment of morbidity due to infection with *Chlamydia psittaci* in subjects. Subjects are humans or animals, but preferably are birds and more preferably poultry, including but not limited to chickens, ducks, geese and turkeys.

A preferred means of administration of the peptides of the present invention is mucosal delivery, more preferably administration by aerosol or inhalation. Other means of administration are all other systemic and mucosal administration routes as well as in ovo administration methods, well known to the skilled person.

The composition of the present invention can further comprise a pharmaceutically acceptable excipient conventional in the art. Non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

In the composition, also referred to as polyepitope vaccine, the peptides can be present as a mixture of individual peptides and/or (part of) the peptides can be linked to each other and/or are part of vector/carrier construct. In a specific embodiment, the composition comprises a polyepitope construct. The term polyepitope vaccine as used herein denotes a composition that does not occur as such in nature. Hence, the "polyepitope vaccine" of the present invention does not encompass a wild-type full-length protein but includes two or more isolated epitopes of the present invention, not necessarily in the same sequential order or number (repetitions might be used) as in nature. The polyepitope vaccine of the present invention preferably comprises 2 or more, 5 or more, 10 or more, 13 or more, 15 or more, 20 or more, or 25 or more epitopes of the present invention. More specific, the polyepitope vaccine comprises 2, 3, 4, 5, 6, 7, 8, 9, 10, 11, 12. 13, 14, 15, 16, 17, 18, 19, 20, 21, 22, 23, 24, 25, or more epitopes. The epitopes of the polyepitope vaccine can be prepared as synthetic peptides or recombinant peptides. These synthetic peptides or recombinant peptides can be used either individually or directly or indirectly linked to one another. Optionally, two or more of the epitopes (either B-cell and/or T-cell epitopes) can be linked in a construct, referred to herein as a polyepitope construct, and are either contiguous or are separated by a linker or one or more spacer amino acids. "Link" or "join" refers to any method known in the art for functionally connecting epitopes. More particular, the polyepitope vaccine of the present invention is a synthetic or recombinant string of two or more peptides harbouring (part of) the epitopes as described herein. Methods for preparing a polypeptide, which may comprise a polyepitope (polyepitope vaccine/construct), are known in the art and are described in for example the book Molecular Cloning; a laboratory manual by Joseph Sambrook and David William Russell—2001.

According to a specific embodiment, the composition or polyepitope vaccine of the present invention comprises the following B-cell epitopes: GTASATT (SEQ ID NO 92), GTDFNN (SEQ ID NO 93) and NPTLLGKA (SEQ ID NO 94), or a variant thereof, and the following T-cell epitopes: SEQ ID NO 20 and 101-117, or a variant thereof. In a particular embodiment said B-cell epitopes are comprised in the following peptide sequences: SEQ ID NO 94-96, and said T-cell epitopes in the composition are comprised in the following peptide sequences: SEQ ID NO 7-8, 70, 71, 73, 75-77, 79-81 and 91, or a variant thereof.

In a preferred embodiment, the composition or polyepitope vaccine of the present invention comprises the following peptide sequences:
AA sequence 30-51 (EPSLLIDGTMWEGASGDPCDPC, CD4Th2 epitope in CS1; SEQ ID NO 97), AA sequence 93-100 (TGTASATT, immunodominant B cell epitope in VS1; SEQ ID NO 95), AA sequence 163-170 (KGTDFNNQ, serovar D B-cell epitope in VS2; SEQ ID NO 96), AA sequence 305-340 (AQPKLATAVLDLTTWNPTLLGKAT-TVDGTNTYSDFL, CD4Th2 and immunodominant B cell epitope in VS4; SEQ ID NO 98) (the CD4Th2—B cell cluster), and AA sequence 257-301 (AATDTKSATLKYHEWQVGLALSYRLNM-LVPYIGVNWSRATFDADT) (CD4Th1—CD8 cluster in CS4; SEQ ID NO 99), or variants thereof In a further preferred embodiment, the composition or polyepitope vaccine of the present invention comprises the following peptide sequences: AA sequence 53-67 (TWC-DAISIRAGYYGD, CD4Th1 and CD8 epitope; SEQ ID NO 20), AA221-235 (EMLNVTSSPAQFVIH, CD4Th2 epitope; SEQ ID NO 62), and AA163-170 KGTDFNNQ, B-cell epitope; SEQ ID NO 96).

The present invention further includes an isolated nucleic acid encoding the epitopes, peptides or polyepitope construct as described herein. Particular nucleic acids encoding the peptides of the invention are the following.

```
Corresponding to AA 30-51: CD4Th2 epitope:
                                        (SEQ ID NO 118)
5'GAACCAAGTTTATTAATCGATGGCACTATGTGGGAAGGTGCTTCAGGA

GATCCTTGCGATCCTTGC-3'

Corresponding to AA 93-100: CD4Th1 and
immunodominant B-cell epitope:
                                        (SEQ ID NO 119)
5'-ACAGGAACAGCAAGTGCTACTACT-3'

Corresponding to AA 163-170: serovar-specific B-
cell epitope:
                                        (SEQ ID NO 120)
5'-AAAGGAACTGATTTCAATAATCAA-3'

Corresponding to AA 257-301: CD4Th1 + CD8 T cell
epitope cluster:
                                        (SEQ ID NO 122)
5'GCTGCTACAGATACTAAGTCTGCAACACTCAAATATCATGAATGGCAA

GTTGGTCTAGCACTCTCTTACAGATTGAACATGCTTGTTCCTTACATTGG

CGTAAACTGGTCAAGAGCAACTTTTGATGCTGACACT-3'

Corresponding to AA 305-340: CD4Th2 epitope +
immunodominant B-cell epitope:
                                        (SEQ ID NO 121)
5'GCTCAGCCTAAATTAGCCACTGCTGTTTTAGATTTAACCACTTGGAAC

CCAACACTTTTAGGAAAGGCCACAACTGTCGACGGTACCAATACTTACTC

TGACTTCTTA-3'
```

Further embodiments of the present invention are a vector which comprises a nucleic acid encoding at least the polyepitope vaccine or construct as described herein, and which is capable of expressing the respective peptides. A host cell comprising the expression vector and a method of producing and purifying the herein described peptides are also part of the invention. Suitable vectors that can be used in the present invention are known to the skilled in the art and include a plasmid, a bacterial, a viral vector or a yeast vector. Examples of bacterial vectors are *Salmonella typhi*, BCG (Bacille Calmette Guerin) and *Listeria*. Examples of viral vectors are poxvirus, Alphaviruses (Semliki Forest Virus, Sindbis Virus, Venezuelan Equine Encephalitis Virus (VEE), Herpes simplex Virus (HSV), Kunjin virus, Vesicular Stomatitis Virus (VSV) replication-deficient strains of Adenovirus (human or simian), polyoma vectors (such as SV40 vectors, bovine polyoma), CMV vectors, papilloma virus vectors, influenza virus, measles virus, and vectors derived from Epstein Barr virus. A wide variety of other vectors useful for therapeutic administration or immunization, e.g. lentiviral vectors, retroviral vectors, and the like, will be apparent to those skilled in the art. Examples of yeast vectors are a *Hansenula* cell or *Saccharomyces cerevisiae* cell. The composition according to the present invention can further comprise an antigen delivery system, which optimizes the presentation of the antigen. In a specific embodiment, the antigen delivery system is an enzymatically inactive recombinant adenylate cyclase (CyaA) originating from *Bordetella pertussis* (the causative agent of whooping cough) (Ladant et al., 1999; and in EP1576967).

The composition of the present invention can further comprise an adjuvant. Suitable adjuvants are 1) receptor specific (mucosal) adjuvants such as for instance adjuvants binding to pathogen recognition receptors (PRRs) and ganglioside receptor binding toxins, 2) antigen presenting cell targeting (mucosal) adjuvants such as for instance the ones described by Gerdts et al., (2006). Further examples of adjuvants include, but are not limited to, tensoactive compounds (such as Quil A), mineral salts (such as aluminium hydroxide), micro-organism derived adjuvants (such as muramyl dipeptide), oil-in-water and water-in-oil emulsions (such as Freund's incomplete adjuvant), particulate antigen delivery systems (such as liposomes, polymeric atmospheres, nanobeads, ISCOMATRIX), polysaccharides (such as micro-particulate inulin), nucleic acid based adjuvants (such as CpG motivs), cytokines (such as interleukins and interferons), activators of Toll-like receptors and eurocine L3 en N3 adjuvantia. In a specific embodiment, the adjuvant is an ISCOM™ (ISCOTEC AB, Uppsala, Sweden).

The composition of the present invention can be used as a medicament, and more specific against an infection with a species of the genus *Chlamydia*, preferably wherein said species of the genus *Chlamydia* is *Chlamydia psittaci*. In a further embodiment, the composition is a vaccine. With the term 'vaccine' is meant a biological preparation that elicits a protective immune response in a subject to which the vaccine has been administered. Preferably, the immune response confers some beneficial, protective effect to the subject against a subsequent challenge with the infectious agent. More preferably, the immune response prevents the onset of or ameliorates at least one symptom of a disease associated with the infectious agent, or reduces the severity of at least one symptom of a disease associated with the infectious agent upon subsequent challenge.

Individual and isolated peptides comprising B- and/or T-cell epitopes and comprising the amino acid sequences as described herein (resp. characterized by SEQ ID NO 89, 90, 92-96, and 98; and by SEQ ID NO 1, 7, 8, 9, 10, 11, 12, 13, 18, 20, 21, 22, 24, 25, 26, 27, 29, 30, 31, 32, 35, 41, 42, 43, 44, 46, 49, 50, 51, 53, 54, 55, 56, 60, 61, 63, 64, 65, 66, 67, 68, 69, 70, 71, 72, 73, 74, 75, 76, 77, 78, 79, 80, 81, 82, 84, 85, 86, 87, 91, 97, and 99) are also part of the present invention, as well as the nucleic acids encoding them. As demonstrated, said peptides are particular useful for the development of a vaccine against a species of the genus *Chlamydia*, and more specific *C. psittaci*. Hence, any combination of two or more of these peptides for producing a polyepitope vaccine and for use in developing a composition or vaccine is part of the present invention. In a specific embodiment, the polyepitope vaccine comprises or consists of a combination of two or more peptides comprising a T cell epitope as described herein. In a further embodiment, the polyepitope vaccine comprises or consists of a combination of two or more peptides comprising a B-cell epitope of the present invention.

In a further aspect of the current invention, administration of the composition as described herein, and in particular a vector comprising the peptides or nucleic acids of the invention, can overcome the inactivating (i.e. neutralizing) effects of maternal antibodies. It is well-known in the art that maternally-transmitted antibodies interfere with the efficacy of early vaccination programs in young subjects. Accordingly, the present invention provides a composition and the use thereof for effectively vaccinating a subject infected with a species of the genus *Chlamydia* that has maternal antibodies against said species. For birds, the composition can be administered according to the present invention in ovo and to hatchlings. In bird embryos, maternal antibodies are deposited in the yolk and are taken up by the embryo as the yolk is resorbed. Typically, maternal antibodies can be detected in the embryo by embryonic day 15. Accordingly, the present invention is useful in increasing the efficacy of vaccines administered after embryonic day 15, more preferably after embryonic day 17, to birds in ovo. Additionally, the methods disclosed herein may be carried out to vaccinate a young bird soon after hatch. In young chickens, maternal antibodies generally disappear by three weeks after hatch. Accordingly, in young birds, the composition of the present invention is administered within about four weeks post-hatch, preferably within about three weeks post-hatch, more preferably within about two weeks post-hatch, still more preferably, within about one week post-hatch, and most preferably within about the first three days post-hatch. Typically, vaccination will be carried out at the time that the birds are transferred from the hatcher (usually one or two days post-hatch).

In an even further embodiment, the invention includes a prime-boost immunization or vaccination against a species of the genus Chlamydia. The priming can be done with the composition, peptides or nucleic acids as described herein. Equally, boosting can be done with the composition, peptides or nucleic acids as described herein.

The invention thus also relates to a method of immunizing a subject against a species of the genus Chlamydia, more specific C. psittaci, comprising administering to the subject the composition as described herein in a prime-boost regimen. In its broadest sense, the term of "prime-boost" refers to the successive administrations of two different vaccine types or immunogenic composition types having at least one epitope or immunogen in common. The priming administration is the administration of a first vaccine or composition type and may comprise one, two or more administrations. The boost administration is the administration of a second vaccine or composition type and may comprise one, two or more administrations, and, for instance, may comprise or consist essentially of annual administrations. The "boost" may be administered from about 2 weeks to about 6 months after the "priming", such as from about 2 to about 8 weeks after the priming, and advantageously from about 2 to about 6 weeks after the priming, and more advantageously, about 2, 3 or 4 weeks after the priming. In a specific embodiment, the prime and boost compositions are the same, and in particular the same peptide composition as described herein.

The present invention further relates to an in vitro method to diagnose an infection with Chlamydia psittaci in a subject comprising:
 contacting a sample from said subject with at least one peptide comprising a B-cell epitope of the present invention, and
 determining the presence of antibodies in said sample binding to said peptide(s).

Such methods are well-known to the skilled person and can be performed by a variety of standard procedures, such as detection of radioactivity, fluorescence, luminescence, chemiluminescence, absorbance, or by microscopy, imaging, etc.

The present invention further encompasses a diagnostic kit comprising at least one peptide comprising a B-cell epitope as described herein. Examples of diagnostic kits include but are not limited to immunoassays including immunohistochemistry, enzyme-linked immunosorbent assay (ELISA), western blotting, immunoradiometric assay (IRMA), lateral flow, dipstick tests, immuno histo/cyto-chemistry and other assays known to those of skill in the art. Immunoassays can be used to determine presence or absence of an antibody in a sample as well as the amount of an antibody in a sample.

A "sample" may include fluid (e.g. blood, serum, saliva, urine, cerebral spinal fluid, pleural fluid, milk, lymph, meat juice, sputum and semen), solid (e. g., stool) or tissue (e.g. cervical tissue) sections taken (isolated) from a subject.

In a particular embodiment, the peptides comprising a B-cell epitope used in the diagnostic method and kit comprises or consists of the following amino acid sequence: 1) TGTASATT (SEQ ID NO 95; immnodominant B cell epitope in VS1), 2) KGTDFNNQ (SEQ ID NO 96; serovar D epitope in VS2) and/or 3) NPTLLGKA (SEQ ID NO 94; immunodominant B cell epitope in VS4), or a variant thereof. Even more particular, the peptide has a length of 5 to 30 amino acids.

The present invention is illustrated by the following Examples, which should not be understood to limit the scope of the invention to the specific embodiments therein.

EXAMPLES

Example 1

*C. psittaci* Subunit Vaccination Experiment

We performed B- and T cell epitope mapping of the *C. psittaci* 'major outer membrane protein' (MOMP) and used B- and T cell epitopes to create a *C. psittaci* subunit (polyepitope) vaccine, which was validated in a pre-clinical trial in specific pathogen free (SPF) chickens. *C. psittaci* strain 92/1293, isolated from a severe outbreak of respiratory disease in a commercial broiler turkey farm in the Netherlands, was used (Vanrompay et al., 1993). The strain was isolated from a pooled homogenate of the lungs, the cloacae and the spleens of diseased turkeys and was characterized as serovar D and genotype D (Geens et al., 2005). Bacteria were grown in Buffalo Green Monkey (BGM) cells as previously described (Vanrompay et al., 1992) and the titration was performed by the method of Spearman and Kaerber (Mayr et al., 1974).

1. B Cell Epitope Mapping

For B cell epitope identification, overlapping synthetic peptides of 8 amino acids (7 amino acids overlap) of the variable domains I to IV of the MOMP sequence were coupled on pins via an extra C-terminal cysteine (Pin-peptides, Pepscan Systems, Lelystad, The Netherlands). A total amount of 100 nmol peptide was coupled to each pin.

The results of the pin-peptide ELISAs for B cell epitope mapping of the MOMP of *C. psittaci* serovar D strain 92/1293, a highly virulent genotype D strain infecting poultry, are presented in FIG. 3. When using the serovar-D specific MAb at a dilution of 1/100 (FIG. 3A), peptide 23 gave the highest signal. At a MAb dilution of 1/600 peptide 23 still gave a high signal while the signal created by the other peptides weakened significantly. Pin-peptide 23 (KGTDFNNQ) is most likely the serovar-D specific epitope of *C. psittaci* genotype D and can be found in the variable sequence region 2 (VS2) of MOMP.

When using serum of SPF turkeys immunized with recombinant MOMP of strain 92/1293, peptide 23 gave a weak signal (FIG. 3B), which indicates that peptide 23 is not predominantly recognized by the immunized animals. However, a very strong signal could be obtained for peptide 12 (TGTASATT) located in VS1 and peptide 43 (NPTLLGKA) located in VS4. The same signal pattern was also obtained when using serum of naturally infected turkeys. Accordingly, the peptides TGTASATT, NPTLLGKA and KGTDFNNQ are immunodominant (strongly recognized by the immune system as shown in FIG. 3) B-cell epitopes and are useful for vaccine development.

Moreover the B-cell epitopes 12 and 43 induce sero-neutralizing antibodies by immunizing SPF chickens with peptide 12 or 43 coupled to the carrier protein KLH (keyhole limpet hemocyanin).

The identified B cell epitopes TGTASATT and NPTLLGKA can be used in an antibody ELISA for detecting *C. psittaci* antibodies in both humans and animals. Immunodominant B cell epitopes can be used as pin-peptides in a highly sensitive antibody ELISA. The serovar specific epitope KGTDFNNQ can be used as pin-peptide in a serovar D-specific antibody ELISA.

2. T Cell Epitope Mapping

For T cell epitope identification, overlapping synthetic peptides of 15 amino acids (14 amino acids overlap) of the complete MOMP sequence were produced (Pep-T-Topes, Pepscan Systems) in 96-well flat bottom tissue culture plates (Greiner Bio-one, Wemmel, Belgium) with an amount of 1-2 mg peptide per well.

Pep-T-Topes were used to identify the T cell epitopes on the MOMP of *C. psittaci* serovar D strain 92/1293. T-cell epitope mapping was based on: a) lymphocyte proliferation assays, b) flow cytometry on proliferating cells using CD4 and CD8 cell surface markers, c) an IFN-γ ELISA on supernatant of proliferating cells and d) an IL-6 bioassay on supernatant of proliferating cells (Lynagh et al., 2000; Zubiaga et al., 1990). Table 1 contains the complete results of B- and T-epitope mapping.

Peptides eliciting one or more of following characteristics are categorized as suitable for vaccine design:
a) Counts per minute (Cpm) in proliferation assay>10000,
b) % CD4≥17.5,
c) % CD8>14.2,
d) IFN-γ>9 pg/ml, and
e) IL-6>1.9 pg/ml.

Peptides comprising T-cell epitopes suitable for vaccine design correspond to SEQ ID NO 1, 7, 8, 9, 10, 11, 12, 13, 18, 20, 21, 22, 24, 25, 26, 27, 29, 30, 31, 32, 35, 41, 42, 43, 44, 46, 49, 50, 51, 53, 54, 55, 56, 60, 61, 63, 64, 65, 66, 67, 68, 69, 70, 71, 72, 73, 74, 75, 76, 77, 78, 79, 80, 81, 82, 84, 85, 86, 87, and 91. From these, peptides especially useful to include in the composition of the present invention are the following:

Peptides comprising a CTL (CD8+) epitope correspond to SEQ ID NO 20, 26, 27, 42, 43, 61, 73, 75, and 80.

Peptides comprising a CD4+ Th1 cell epitope correspond to SEQ ID NO 1, 10-13, 18, 20, 25, 27, 29, 31-32, 35, 42, 46, 51, 53-56, 61, 64-67, 69-71, 73, 75, 79-81, and 87.

Peptides comprising a CD4+ Th2 cell epitope correspond to SEQ ID NO 7, 8, 43, 76, 77, 85, and 91.

From these peptides, a first selection was made to design a polyepitope vaccine.

Many CD4 Th1 epitopes were present on the MOMP and they were found in combination with CD8 epitopes. Especially peptide 281-295 contains a very strong CD4 Th1-CD8 epitope (108.088 cpm). Moreover, these epitopes are located in a large cluster of multiple CD4 Th1 epitopes, one additional CD8 epitope and two CD4 Th2 epitopes present on a peptide, covering amino acids 257 to 296.

TABLE 1

Peptides harbouring B- and T-cell epitopes of *Chlamydia psittaci* genotype D strain 92/1293

| SEQ ID NO | position | Sequence | TC (cmp)[1] | % CD4 | % CD8 | IFN-γ (pg/ml) | IL-6 (pg/ml) | Epitoop |
|---|---|---|---|---|---|---|---|---|
| 1 | 17-31 | ALSLQALPVGNPAEP | 11093 | 13.6 | 0.4 | 9 | 0 | CD4 Th1 |
| 2 | 18-32 | LSLQALPVGNPAEPS | 6393 | 1.7 | 0.8 | 9 | 0 | CD4 Th1 |
| 3 | 25-39 | VGNPAEPSLLIDGTM | 4545 | 9.4 | 0.7 | 9 | 0 | / |
| 4 | 26-40 | GNPAEPSLLIDGTMV | 2027 | 4.9 | 1.0 | 0 | 0 | / |
| 5 | 29-43 | AEPSLLIDGTMWEGA | 4851 | 10.8 | 2.1 | 0 | 1.9 | / |
| 6 | 30-44 | EPSLLIDGTMWEGAS | 7421 | 6.6 | 1.6 | 0 | 1.9 | CD4 Th2 |
| 7 | 35-49 | IDGTMWEGASGDPCD | 14032 | 20.5 | 3.8 | 0 | 3.9 | CD4 Th2 |
| 8 | 36-50 | DGTMWEGASGDPCDP | 9462 | 1.8 | 1.0 | 0 | 3.9 | CD4 Th2 |
| 9 | 37-51 | GTMWEGASGDPCDPC | 15074 | 3.6 | 0.9 | 9 | 0 | / |
| 10 | 40-54 | WEGASGDPCDPCATW | 14332 | 1.6 | 1.0 | 9 | 0 | CD4 Th1 |
| 11 | 41-55 | EGASGDPCDPCATWC | 13289 | 1.4 | 1.0 | 9 | 0 | CD4 Th1 |
| 12 | 42-56 | GASGDPCDPCATWCD | 14731 | 1.6 | 1.0 | 9 | 0 | CD4 Th1 |
| 13 | 43-57 | ASGDPCDPCATWCDA | 16929 | 4.0 | 1.2 | 9 | 0 | CD4 Th1 |
| 14 | 44-58 | SGDPCDPCATWCDAI | 3385 | 0.6 | 0.2 | 0 | 0 | / |
| 15 | 46-60 | DPCDPCATWCDAISI | 5042 | 2.6 | 1.3 | 0 | 1.9 | CD4 Th2 |
| 16 | 47-61 | PCDPCATWCDAISIR | 5856 | 5.9 | 1.0 | 0 | 0 | |
| 17 | 48-62 | CDPCATWCDAISIRA | 2252 | 2.2 | 1.0 | 0 | 0 | / |

TABLE 1-continued

Peptides harbouring B- and T-cell epitopes of *Chlamydia psittaci* genotype D strain 92/1293

| | | | | | | | | |
|---|---|---|---|---|---|---|---|---|
| 18 | 49-63 | DPCATWCDAISIRAG | 14852 | 8.4 | 0.8 | 9 | 0 | CD4 Th1 |
| 19 | 50-64 | PCATWCDAISIRAGY | 8720 | 6.9 | 1.8 | 0 | 0 | / |
| 20 | 53-67 | TWCDAISIRAGYYGD | 35485 | 13.6 | 6.9 | 9 | 0 | CD4 Th1 CD8 |
| 21 | 54-68 | WCDAISIRAGYYGDY | 30171 | 17.3 | 1.5 | 0 | 0 | CD4 |
| 22 | 55-69 | CDAISIRAGYYGDYV | 3668 | 37.0 | 7.0 | 0 | 0 | / |
| 23 | 58-72 | ISIRAGYYGDYVFDR | 3684 | 16.4 | 1.9 | 0 | 0 | / |
| 24 | 59-73 | SIRAGYYGDYVFDRV | 11032 | 21.5 | 2.1 | 0 | 0 | CD4 |
| 25 | 60-74 | IRAGYYGDYVFDRVL | 18411 | 12.1 | 0.9 | 9 | 0 | CD4 Th1 |
| 26 | 61-75 | RAGYYGDYVFDRVLK | 12444 | 21.4 | 4.6 | 0 | 0 | CD4 + CD8 |
| 27 | 66-80 | GDYVFDRVLKVDVNK | 5363 | 24.0 | 7.8 | 9 | 0 | CD4 Th1 CD8 |
| 28 | 67-81 | DYVFDRVLKVDVNKT | 5366 | 4.1 | 1.2 | 9 | 0 | CD4 Th1 |
| 29 | 71-85 | DRLKVDVNKTFSGM | 9311 | 5.7 | 0.9 | 18 | 0 | CD4 Th1 |
| 30 | 72-86 | RVLKVDVNKTFSGMA | 4741 | 19.4 | 2.1 | 0 | 0 | / |
| 31 | 73-87 | VLKVDVNKTFSGMAK | 27420 | 8.0 | 1.1 | 9 | 0 | CD4 Th1 |
| 32 | 85-99 | MAKSPTEATGTASAT[2] | 80.468 | 25.1 | 2.0 | 32 | 0 | CD4 Th1 B-cell epitope |
| 33 | 91-105 | EATGTASATTTAVDR | 3433 | 1.7 | 0.8 | 9 | 0 | B-cell epitope |
| 34 | 95-109 | TASATTTAVDRTNLA | 8278 | 2.6 | 0.7 | 0 | 0 | CD4 |
| 35 | 97-111 | SATTTAVDRTNLAYG | 60.941 | 16.4 | 2.9 | 18 | 0 | CD4 Th1 |
| 36 | 98-112 | ATTTAVDRTNLAYGK | 2241 | 2.7 | 1.2 | 9 | 0 | / |
| 37 | 107-121 | NLAYGKHLQDAEWFT | 2532 | 2.6 | 0.6 | 0 | 0 | / |
| 38 | 109-123 | AYGKHLQDAEWFTNA | 6018 | 3.9 | 1.2 | 9 | 0 | CD4 Th1 |
| 39 | 111-125 | GKHLQDAEWFTNAAF | 3621 | 12.2 | 3.4 | 9 | 0 | / |
| 40 | 112-126 | KHLQDAEWFTNAAFL | 2513 | 4.1 | 1.1 | 0 | 0 | / |
| 41 | 113-127 | HLQDAEWFTNAAFLA | 2546 | 19.7 | 5.8 | 9 | 0 | / |
| 42 | 119-133 | WFTNAAFLALNIWDR | 25.067 | 18.7 | 12.1 | 9 | 0 | CD4 Th1 CD8 |
| 43 | 131-145 | WDRFDIFCTLGASNG | 5775 | 58.7 | 14.9 | 0 | 1.9 | CD4 Th2 CD8 |
| 44 | 142-156 | ASNGYFKASSAAFNL | 2009 | 18.7 | 4.0 | 0 | 0 | / |
| 45 | 154-168 | FNLGVLIGLKGTDFN[3] | 1129 | 10.6 | 2.1 | 0 | 0 | B-cell epitope |
| 46 | 166-180 | DFNNQLPNVAITQGV | 5683 | 18.3 | 2.3 | 9 | 0 | CD4 Th1 B-cell epitope |
| 47 | 167-181 | FNNQLPNVAITQGVV | 1321 | 2.3 | 0.9 | 9 | 0 | / |
| 48 | 168-182 | NNQLPNVAITQGVVE | 1262 | 15.9 | 6.1 | 9 | 0 | / |
| 49 | 184-198 | YTDTTFSWSVGARGA | 2811 | 44.1 | 18.3 | 9 | 0 | / |
| 50 | 195-209 | ARGALWECGCATLGA | 7929 | 18.3 | 6.1 | 0 | 0 | CD4 |
| 51 | 196-211 | RGALWECGCATLGAE | 21.981 | 7.5 | 2.6 | 9 | 0 | CD4 Th1 |
| 52 | 197-211 | GALWECGCATLGAEF | 4416 | 5.3 | 0.1 | 0 | 0 | / |
| 53 | 201-215 | ECGCATLGAEFQYAQ | 15.883 | 1.6 | 0.9 | 9 | 0 | CD4 Th1 |
| 54 | 202-216 | CGCATLGAEFQYAQS | 23.344 | 2.1 | 0.4 | 18 | 0 | CD4 Th1 |

TABLE 1-continued

*Peptides harbouring B- and T-cell epitopes of Chlamydia psittaci genotype D strain 92/1293*

| | | | | | | | |
|---|---|---|---|---|---|---|---|
| 55 | 203-217 | GCATLGAEFQYAQSN | 10.217 | 4.5 | 2.8 | 18 | 0 | CD4 Th1 |
| 56 | 204-218 | CATLGAEFQYAQSNP | 6924 | 21.9 | 4.3 | 18 | 0 | CD4 Th1 |
| 57 | 205-219 | ATLGAEFQYAQSNPK | 6533 | 7.1 | 1.3 | 9 | 0 | CD4 Th1 |
| 58 | 206-220 | TLGAEFQYAQSNPKI | 4225 | 12.4 | 1.7 | 9 | 0 | / |
| 59 | 207-221 | LGAEFQYAQSNPKIE | 1218 | 10.7 | 3.6 | 9 | 0 | / |
| 60 | 208-222 | GAEFQYAQSNPKIEM | 2142 | 3.1 | 1.1 | 18 | 0 | / |
| 61 | 214-228 | AQSNPKIEMLNVTSS | 21.643 | 28.9 | 7.3 | 18 | 0 | CD4 Th1 CD8 |
| 62 | 221-235 | EMLNVTSSPAQFVIH | 7037 | 16.0 | 4.4 | 0 | 1.9 | CD4 Th2 |
| 63 | 222-236 | MLNVTSSPAQFVIHK | 2178 | 24.2 | 5.8 | 18 | 0 | / |
| 64 | 233-247 | VIHKPRGYKGTGSNF | 44.429 | 23.3 | 0.8 | 9 | 0 | CD4 Th1 |
| 65 | 244-258 | GSNFPLPIDAGTEAA | 25.253 | 4.8 | 0.6 | 9 | 0 | CD4 Th1 |
| 66 | 245-259 | SNFPLPIDAGTEAAT | 39.106 | 5.4 | 0.6 | 9 | 0 | CD4 Th1 |
| 67 | 246-260 | NFPLPIDAGTEAATD | 13.698 | 17.5 | 0.5 | 9 | 0 | CD4 Th1 |
| 68 | 251-265 | IDAGTEAATDTKSAT | 15.894 | 8.1 | 1.2 | 0 | 0 | CD4 |
| 69 | 252-266 | DAGTEAATDTKSATL | 10.513 | 77.7 | 5.7 | 9 | 0 | CD4 Th1 |
| 70 | 257-271 | AATDTKSATLKYHEW | 39.489 | 8.3 | 0.4 | 9 | 0 | CD4 Th1 |
| 71 | 262-276 | KSATLKYHEWQVGLA | 19.151 | 13.2 | 3.0 | 32 | 0 | CD4 Th1 |
| 72 | 263-278 | SATLKYHEWQVGLAL | 2841 | 5.4 | 0.9 | 18 | 0 | CD4 Th1 |
| 73 | 264-279 | ATLKYHEWQVGLALS | 20.815 | 48.8 | 7.1 | 18 | 0 | CD4 Th1 CD8 |
| 74 | 266-280 | LKYHEWQVGLALSYR | 3013 | 61.0 | 14.2 | 9 | 0 | / |
| 75 | 267-281 | KYHEWQVGLALSYRL | 13.516 | 43.5 | 20.4 | 9 | 0 | CD4 Th1 CD8 |
| 76 | 268-282 | YHEWQVGLALSYRLN | 20.591 | 20.6 | 1.4 | 0 | 1.9 | CD4 Th2 |
| 77 | 269-283 | HEWQVGLALSYRLNM | 62.709 | 39.4 | 5.8 | 0 | 3.9 | CD4 Th2 |
| 78 | 279-293 | YRLNMLVPYIGVNWS | 5510 | 61.7 | 5.4 | 0 | 1.9 | CD4 |
| 79 | 280-294 | RLNMLVPYIGVNWSR | 41.321 | 60.4 | 3.6 | 9 | 0 | CD4 Th1 |
| 80 | 281-295 | LNMLVPYIGVNWSRA | 108.088 | 65.8 | 20.2 | 9 | 0 | CD4 Th1 CD8 |
| 81 | 282-296 | NMLVPYIGVNWSRAT | 28.136 | 30.9 | 0.9 | 9 | 0 | CD4 Th1 |
| 82 | 287-302 | YIGVNWSRATFDADT | 14.406 | 6.8 | 0.6 | 0 | 0 | CD4 |
| 83 | 291-305 | NWSRARTFDADTIRIA | 2483 | 16.0 | 2.8 | 0 | 0 | / |
| 84 | 291-306 | WSRATFDADTIRIAQ | 21.434 | 26.4 | 3.9 | 0 | 0 | CD4 |
| 85 | 293-307 | SRATFDADTIRIAQP | 41.778 | 8.6 | 1.2 | 0 | 1.9 | CD4 Th2 |
| 86 | 295-309 | ATFDADTIRIAQPKL | 2539 | 18.5 | 1.7 | 0 | 0 | / |
| 87 | 299-313 | ADTIRIAQPKLATAV | 10.759 | 12.0 | 2.2 | 9 | 0 | CD4 Th1 |
| 88 | 304-318 | IAQPKLATAVLDLTT | 1829 | 10.8 | 3.1 | 0 | 0 | / |
| 89 | 305-319 | AQPKLATAVLDLTTW | 6541 | 7.7 | 0.5 | 0 | 0 | Flanking the B-cell epitope NPTLLGKA |
| 90 | 311-325 | TAVLDLTTWNPTLLG[4] | 5087 | 6.4 | 0.6 | 0 | 1.9 | Part of the B-cell epitope NPTLLGKA + CD4 Th2 |
| 91 | 326-340 | KATTVDGTNTYSDFL | 5259 | 17.5 | 1.2 | 0 | 1.9 | Part of the immuno-dominant B-cell epitope NPTLLGKA + CD4 Th2 |

▓ Location of the variable domains of MOMP

[1]TC (cpm):T-cell proliferation assay (counts per minute)
[2]GTASATT: the identified immunodominant B-cell epitope.
[3]GTDFNN: the serovar D- specific B-cell epitope
[4]NPTLLGKA: the identified immunodominant B-cell epitope

3. *C. psittaci* Vaccine

Peptides including the identified B and T cell epitopes of the MOMP of *C. psittaci* strain 92/1293 were synthetically designed.

4. Vaccination Trial 1: Vaccination of SPF Chickens

Experiments were performed in negative pressure isolators (IM 1500, Montair Sevenum, the Netherlands). The experimental design was evaluated and approved by the Ethical Commission for Animal Experiments of Ghent University. To evaluate the polyepitope vaccine, 42 specific pathogen free (SPF) chickens (Lohman, Germany) were divided into 6 groups of 7 animals each. The vaccination scheme and the experimental set-up are presented in Table 3 and 4. The animals were vaccinated by aerosol (Cirrus™ nebulizer; 5 μm aërosol particle size; Laméris, Aartselaar, Belgium) providing a vaccine dose of 500 μg of each synthetic peptide/animal. The control animals each received 60 μg of ISCOMS by aerosol. Primo vaccination was performed in 7 day-old chickens of groups 1 to 6 (Table 3). At the age of 4 weeks, animals of groups 1 to 4 were aerogenically infected using the Cirrus™ nebulizer, while those of groups 5 and 6 received a booster vaccination. At the age of 7 weeks, all animals of groups 1 to 4 were euthanized, while those of groups 5 (age 6 weeks) were aerogenically infected using the Cirrus™ nebulizer. The experimental infection dose in each isolator was $10^6$ $TCID_{50}$ of strain *C. psittaci* 92/1293. Animals of groups 5 and 6 were euthanized at 21 days post infection (p.i.).

```
Peptide 1:
                                                  (SEQ ID NO 97)
EPSLLIDGTMWEGASGDPCDPC Peptide 2:
                                                  (SEQ ID NO 95)
TGTASATT Peptide 3:
                                                  (SEQ ID NO 96)
KGTDFNNQ Peptide 4:
                                                  (SEQ ID NO 98)
AQPKLATAVLDLTTWNPTLLGKATTVDGTNTYSDFL Peptide 5:
                                                  (SEQ ID NO 99)
AATDTKSATLKYHEWQVGLALSYRLNMLVPYIGVNWSRATFDADT
```

TABLE 3

Vaccination scheme.

| Group (n) | Name | Primo vaccination (day 7) | Dose (μg) | Booster vaccination (day 21) | Dose (μg) |
|---|---|---|---|---|---|
| 1 (7) | Iscoms (1 x) | Iscoms | 60 | none | 60 |
| 2 (7) | B (1 x) | Peptides 1, 2, 3 and 4 | 500 | none | 500 |
| 3 (7) | T (1 x) | Peptide 5 | 500 | none | 500 |
| 4 (7) | B + T (1 x) | Peptides 1, 2, 3, 4 and 5 | 500 | none | 500 |
| 5 (7) | Iscoms (2 x) | Iscoms | 60 | Iscoms | 60 |
| 6 (8) | B + T (2 x) | Peptides 1, 2, 3, 4 and 5 | 500 | Peptides 1, 2, 3, 4 and 5 | 500 |

TABLE 4

Timing of vaccination, challenge and euthanasia for groups 1 to 6.

| Group | Primo vaccination (age in weeks) | Booster vaccination (age in weeks) | Challenge (age in weeks) | Euthanasia (age in weeks) |
|---|---|---|---|---|
| 1 | 1 | / | 4 | 7 |
| 2 | 1 | / | 4 | 7 |
| 3 | 1 | / | 4 | 7 |
| 4 | 1 | / | 4 | 7 |
| 5 | 1 | 4 | 6 | 9 |
| 6 | 1 | 4 | 6 | 9 |

4.1. Monitoring and Sampling

Clinical signs were scored daily until necropsy. Pharyngeal and cloacal excretion of *C. psittaci* was monitored on day 1 of the experiment and on every other day starting at 4 days post infection (p.i.) until necropsy at 21 days p.i., using rayon-tipped, aluminium shafted swabs (Colpan; Fiers, Kuurne, Belgium) provided with *C. psittaci* transport medium (sucrose 74.6 g/l (Acros Organics, Geel, Belgium); $KH_2PO_4$ 5.1 g/l and $K_2HPO_4$ 1.2 g/l (Sigma); L-glutamic acid mono potassium salt 0.9 g/l (Invitrogen, Merelbeke, Belgium) and fetal calf serum 10% v/v (Greiner, Wemmel, Belgium); gentamycin 50 μg/ml (Invitrogen); vancomycin 100 μg/ml and streptomycin 100 μg/ml (Soenen, Merelbeke, Belgium); nystatin 25000 U/ml (Sigma) pH 7). Swabs were stored at −80° C. until processed.

Blood samples for the detection of MOMP-specific serum antibody titres were collected prior to each vaccination, immediately prior to the experimental infection and at euthanasia at 21 days p.i. The samples were stored overnight at room temperature, centrifuged (300×g, 10 min, 4° C.) and afterwards serum was collected. The serum was pretreated with kaolin to remove background activity (Novak et al., 1993) and stored at −80° C.

At the time of euthanasia, 21 days p.i., proliferative responses of peripheral blood lymphocytes and spleen lymphocytes were determined by use of a T cell proliferation assay. Additionally, the amount of immune cells in blood and spleen was determined by flow cytometry. At euthanasia, all chickens were examined for gross lesions. The scoring system for gross pathology is presented in Table 5. Cryostat tissue sections of conchae, the conjunctivae, the trachea, the lungs, thoracic and abdominal airsacs, the pericardium, liver and spleen were prepared for the presence of chlamydial antigen.

TABLE 5

Scoring system for *C. psittaci* gross pathology present in euthanized chickens.

| Tissue | Score 1* | Score 2 | Score 3 |
|---|---|---|---|
| Conjunctivae | Slightly congested | Severely congested | Petechiae |
| Conchae | Slightly congested | Severely congested | Necrosis |
| Trachea | Slightly congested | Moderately congested | Severely congested |
| Lungs | Slightly congested | Severely congested | Severely congested + grey inflam. foci |
| Thoracic air sacs | Diffuse opacity | Focal fibrin deposits | Severe fibrinous airsacculitis |
| Abdominal air sacs | Diffuse opacity | Few fibrin deposits | Severe fibrinous airsacculitis |
| Pericardium | Serous pericarditis | Sero-fibrinous pericarditis | Fibrinous adhesive pericarditis |

TABLE 5-continued

| Scoring system for *C. psittaci* gross pathology present in euthanized chickens. | | | |
|---|---|---|---|
| Tissue | Score 1* | Score 2 | Score 3 |
| Spleen | Slightly enlarged | Moderately enlarged | Severely enlarged & petechiae |
| Liver | Slightly enlarged | Moderately enlarged | Severely enlarged |

*score 0 = no gross pathology.

4.2. Clinical Signs

Clinical signs could be observed in all animals of the control groups (group 1 and 5) starting from day 4 p.i. until the end of the experiment on day 21 p.i. All control chickens appeared lethargic and showed anorexia, conjunctivitis, rhinitis, respiratory distress and diarrhea. At first, the main symptoms were lethargia, anorexia and conjunctivitis in all. Sometimes, 6 of 7 (85%) animals also shed watery droppings. From day 8 p.i. until day 10 p i rhinitis appeared in all and from day 11 p.i. until day 21 p.i., all animals intermittently showed dyspnee. At euthanasia, 4 of 7 (57%) had large amounts of mucus in their beak.

Clinical signs in group 2 first appeared at day 4 p.i., with 3 of 7 (43%) animals showing rhinitis and conjunctivitis. From day 9 p.i. conjunctivitis and rhinitis were observed in all. The number of animals with conjunctivitis and rhinitis gradually declined towards day 17 p.i. At that time all chickens of group 2 appeared healthy.

On day 4 p.i., 4 animals (67%) of groups 3 and 4 showed conjunctivitis. One day later conjunctivitis started to diminish in those four animals but 3 of them (50%) got rhinitis for the following four (group 3) or two (group 4) days. On day 10 and 8 p.i., chickens of groups 3 and 4, respectively, showed healthy.

All vaccinated animals of group 6 remained very active after the experimental infection and they were eating well. They showed no clinical symptoms.

Thus, regarding the clinical signs, protection was best in group 6, followed by group 4, 3 and 2, respectively.

4.3. Macroscopic Lesions

The results of the pathological examination at euthanasia are presented in FIG. 5. Mean scores per group are presented ±SD. Groups 2, 3 and 4 were statistically compared to the control group 1. Group 6 was statistically compared to the control group 5.

First of all, we need to discuss the observations for the spleen as they are not presented in FIG. 5. The spleen of all control chickens was moderately congested and 2 spleens of chickens of group 1 and one spleen of a chicken of group 5 showed petechiae. Slight to moderate congestion was also observed in spleens of chickens of groups 2 and 3. The spleen of one chickens in each of the latter groups also showed petechiae. The spleen of the chickens of group 4 and 6 was moderately to severely enlarged, but instead of congested, the spleens appeared swollen with macroscopically visible white pulpa, indicative for immunostimulation. The latter was more prominent in chickens of group 6 as compared to group 4.

Control chickens of group 1 showed gross pathology in all examined tissues but one, namely the trachea. In group 2, gross pathology was observed in 6 of 10 (60%) examined tissues. In group 3, gross pathology was observed in 9 of 10 (90%) examined tissues. However, the lesions in the trachea of some chickens were most probably due to the euthanasia. Thus, in group 3, gross pathology was observed in 8 of 10 (90%) examined tissues.

Overall, group 4 was significantly better protected than the control group 1. Protection in group 4 was also better than for groups 2 and 3, as gross pathology was only observed in 1 of 10 (10%) examined tissues, namely the lungs. Gross pathology was observed in the lung of 2 of 7 animals of group 4.

Control chickens of group 5 showed gross pathology in all examined tissues but one, namely the trachea. In group 6, gross pathology was only observed in the lung in 1 of 8 animals. Liver lesions were only observed in groups 1, 2, 3 and 5 indicative for septicaemia at the time of euthanasia.

Thus, regarding the autopsy results, protection was best in groups 6 and 4.

4.4. *Chlamydia* Replication and Excretion

Cryostat tissue sections (5 μm) of the conchae, the conjunctivae, the trachea, the lungs, thoracic and abdominal airsacs, the pericardium, liver and spleen were examined for *C. psittaci* replication by the IMAGEN™ immunofluorescence staining (IMAGEN™ *CHLAMYDIA*, Oxoid, Drongen, Belgium), as previously described (Vanrompay et al., 1994a). *C. psittaci* positive cells were enumerated in five randomly selected microscopic fields (600×, Nikon Eclipse TE2000-E, Japan) and scored between 0 and 5: score 0 indicated no *C. psittaci* present; score 1 was given when a mean of 1-5 elementary bodies (infectious, non-metabolic morphological form) was present; score 2, 3, 4 and 5 were given when a mean of 1-5, 6-10, 10-20 and >20 inclusion (actively replicating organisms) positive cells was present.

Swabs were examined for *C. psittaci* excretion by bacterial culture in Buffalo Green Monkey (BGM) cells (Vanrompay et al., 1992) and subsequent chlamydial identification using the IMAGEN™ direct immunofluorescence assay (Vanrompay et al., 1994b). The presence of *C. psittaci* was scored as for bacterial replication in different tissues. Swabs taken at day 1 of the experiment were negative for *C. psittaci*. Culture results for swabs taken at 21 days post infection (euthanasia) are presented in Table 6. The results for the remaining swabs are presented in Table 22.

TABLE 6

| Pharyngeal and cloacal excretion of *C. psittaci* at euthanasia, 21 days p.i. | | | | | | |
|---|---|---|---|---|---|---|
| | Group 1 | Group 2 | Group 3 | Group 4 | Group 5 | Group 6 |
| Pharyngeal excretion | | | | | | |
| Day 21 p.i | 1.71 ± 0.39 | 1.0 ± 0.40 | 0.5 ± 0 | 0.5 ± 0 | 1.78 ± 0.26 | 0.5 ± 0 |
| Cloacal excretion | | | | | | |
| Day 21 p.i. | 2.0 ± 0 | 0.71 ± 0.39 | 0.5 ± 0 | 0.5 ± 0 | 1.92 ± 1.01 | 0.5 ± 0 |

At euthanasia, *C. psittaci* pharyngeal excretion was significantly higher in groups 1 and 2, as compared to groups 3 and 4. At euthanasia, pharyngeal *C. psittaci* excretion was significantly higher for group 5 than for group 6. The same was the case for the cloacal excretion. Thus, regarding *C. psittaci* excretion at 21 days p.i., protection was equally best in groups 3, 4 and 6.

4.5. Antibody Responses

The serum samples (FIG. 6) and mucosal swabs (FIG. 7) of the chickens were analyzed by an enzyme-linked immunosorbent assay (ELISA). The total IgG(H+L) antibody titers were determined as previously described, using the recombinant MOMP, hereinafter called rMOMP, antigen to coat the plates (Verminnen et al., 2006). Two-fold dilutions, starting at 1/40 for sera and 1/20 for mucosal swabs and taking into account the dilution made by the kaolin treatment, were incubated into the wells to react with the rMOMP coating. Detection MOMP-specific isotypes still needs to be done 1/500 dilutions of cross-reactive anti-chicken IgG-, IgM- and IgA specific peroxidase-conjugated polyclonal antibodies (Bethyl Laboratories, Inc., Montgomery, USA). After the addition of the substrate $H_2O_2$ and the chromogen ABTS, the maximum absorbance at 405 nm could be determined. Samples were considered positive if the absorbance exceeded the cut-off value, calculated as the mean of the negative control absorbencies plus twice the standard deviation. Titers were presented as the reciprocal of the highest serum dilution with an absorbance above the cut-off value. As a positive control, serum obtained from previous vaccination experiments was used.

First the comparison of groups 1 to 4. On day −14, the mean antibody titer of group 1 was significantly lower than the mean antibody titers of groups 3 and 4. At that time, the mean antibody titer for group 1 was statistically the same as for group 2. However, mucosal primo immunization did not result in significant higher serum antibody titers at the day of infection (day −1). At day −1, mean serum antibody titers in groups 2, 3 and 4 were statistically the same as for both control group 1. Infection of groups 1, 2, 3 and 4 resulted in augmenting serum antibody titers in the control group 1 and in the better-protected group 4. At 22 days post infection, the mean serum antibody titer for group 4 was significantly higher than for the control group 1 and than for groups 2 and 3.

Secondly, the comparison of groups 5 and 6. Again, on day −14, the mean serum antibody titer of group 5 was significantly lower than the mean antibody titer of group 6. Again, mucosal primo immunization did not result in significant higher serum antibody titers at the day of infection (day −1). At day −1, the mean serum antibody titer in group 6 was statistically the same as for the control group 5. However, one week prior to the infection, the mean serum antibody titer in group 6 was significantly higher than for the control group 5. The same was true at two days and one week after the experimental infection. Thereafter, serum antibodies in the best-protected group 6 declined rapidly while those in the unprotected control group 5 rapidly augmented till 14 days post infection.

Most relevant information is the significant increase of mean mucosal antibody titers following mucosal primo vaccination in the better-protected groups 4 and 6 (day −1), as compared to the control groups 1 and 5 and the immunized groups 2 and 3. Chickens in groups 4 and 6 received the same vaccine. Infection of groups 1, 2, 3 and 4 at day −1 resulted in augmenting mean mucosal antibody titers in the unprotected group 1 and the less protected groups 2 and 3. The mean mucosal antibody titers in the better-protected group 4 generally declined following infection. Booster vaccination in group 6 had no visible effect on the mean mucosal antibody titer. Infection of groups 5 and 6, first resulted in a rapidly augmenting and a rapidly declining mean mucosal antibody titer in the unprotected group 5 and the best protected group 6, respectively. From 7 days p.i. onwards mean mucosal antibody titers in the best protected group 6 continued to rise till 21 days p.i., while those in the unprotected group 5 declined and even disappeared at 14 days p.i.

4.6. Lymphocyte Proliferative Responses

Peripheral blood leukocytes (PBL) were isolated from heparinized blood samples obtained by venepuncture (*V. ulnaris*) and from the spleen from each chicken, at 21 days p.i. at euthanasia. Lymphocyte proliferative tests were performed as previously described (Vanrompay et al., 1999b). Briefly, non-adherent cells were grown in duplicate in 96-well tissue culture plates at $10^6$ cells in 150 μl of DMEM (Invitrogen) supplemented with 20% heat-inactivated fetal calf serum (Greiner), 1% nonessential amino acids, 1% sodium pyruvate, 1% L-glutamine, 1% gentamycine and 0.0001% β-mercaptoethanol (all Invitrogen). For antigen proliferation, 20 μg of recombinant MOMP was added to individual wells. Negative and positive controls included cells stimulated with either plain medium or with 10 μg concanavalin A (Con A), respectively. Cells were incubated at 39.5° C. in a humidified incubator with 5% $CO_2$. Con A or antigen-induced proliferation was measured by incorporation of $^3$H-thymidine (1 μCi/well) during at last 16 h of culture, at days 2 (ConA) and 6, respectively. Cultures were harvested onto glass fiber filter strips with a cell harvester (Skatron, Liers, Norway). The radioactivity incorporated into the DNA was measured with a β-scintillation counter (Perkin-Elmer, Brussels, Belgium). The stimulation index (SI) was defined as the ratio of counts per minute (cpm) of stimulated cultures on medium-only cultures. Results are presented in Table 7.

4.7. Statistical Analysis

The non-parametric Krukal-Wallis and Mann-Whitney tests were employed for statistical analyses. Results were considered to be significantly different at the level of $p<0.05$.

TABLE 7

Mean stimulation index ± standard error mean.

| | Blood lymphocytes | | Spleen lymphocytes | |
|---|---|---|---|---|
| | Inactivated bacteria | Recombinant MOMP of *C. psittaci* | Inactivated bacteria | Recombinant MOMP of *C. psittaci* |
| Group 1 | 1.48 ± 0.24 | 1.72 ± 0.27 | 1.02 ± 0.10 | 1.54 ± 0.46 |
| Group 2 | 3.92 ± 1.66 | 1.58 ± 0.38 | 1.76 ± 0.09 | 1.17 ± 0.70 |
| Group 3 | 4.2 ± 2.19 | 2.09 ± 0.97 | 1.67 ± 0.98 | 1.34 ± 0.13 |
| Group 4 | 7.9 ± 0.0 | 8.37 ± 2.74 | NT | 3.85 ± 0.56 |
| Group 5 | 1.22 ± 0.19 | 1.76 ± 0.25 | 1.32 ± 0.41 | 0.92 ± 0.25 |
| Group 6 | 5.03 ± 1.41 | 3.13 ± 0.74 | 17.6 ± 6.41 | 17.9 ± 6.89 |

For the primo vaccinated groups 1 to 4, protection was correlated with a significantly higher stimulation index for in vitro restimulation of blood lymphocytes with inactivated *C. psittaci* whole organisms as well as with recombinant MOMP of *C. psittaci*. For the primo vaccinated groups 1 to 4, protection was correlated with a significantly higher stimulation index for in vitro restimulation of spleen lymphocytes with recombinant MOMP of *C. psittaci*. Unfortunately, we could not test inactivated bacteria for group 4.

For groups 5 and 6, protection was correlated with a significantly higher stimulation index for in vitro restimulation of blood and spleen lymphocytes with inactivated *C. psittaci* whole organisms as well as with recombinant MOMP of *C. psittaci*.

Protection was correlated with higher CD4/CD8 ratios for peripheral blood lymphocytes at any time point post infection.

Conclusion Vaccination Trial 1

Groups 4 and 6 receiving a combination of B and T cell epitopes were significantly protected against clinical signs, gross pathology and bacterial excretion. Regarding clinical signs, groups 6 was better protected than group 4. Protection was correlated with superior B cell responses upon immunisation (higher mucosal antibody titers post primo vaccination and higher serum antibody titers following booster vaccination), with high proliferative responses of T cells at euthanasia and with a higher CD4/CD8 ratio for peripheral blood lymphocytes at any time point post infection.

5. Vaccination Trial 2: Vaccination of SPF Chickens

From the peptides described herein, a second selection of B-cell, CD4+ Th1, CD4+ Th2 and CD8 T-cell epitopes was made to design a polyepitope vaccine.

TABLE 8

Peptides used in the second vaccination experiment

| Peptide ID | SEQ ID NO | position | Sequence | Epitopes |
|---|---|---|---|---|
| X | 20 | 53-67 | TWCDAISIRAGYYGD | CD4Th1 + CD8 |
| Y | 62 | 221-235 | EMLNVTSSPAQFVIH | CD4Th2 |
| Z | 96 | 163-170 | KGTDFNNQ | B cell |

Experiments were performed in negative pressure isolators (IM 1500, Montair Sevenum, the Netherlands). The experimental design was evaluated and approved by the Ethical Commission for Animal Experiments of Ghent University. To evaluate the vaccine, 18 specific pathogen free (SPF) chickens (Lohman, Cuxhaven, Germany) were divided into three groups of 6 animals. The vaccination scheme is presented in Table 9. Group 1 received 500 µg of each peptide X, Y and Z per animal. In group 2, 3 chickens received 500 µg of peptide X (subgroup 2a), while the other 3 chickens received 500 µg of peptide Y and 500 µg of peptide Z (subgroup 2b). The vaccine was administered as an aerosol using the Cirrus™ nebulizer (2-5 µm aërosol particle size; Laméris, Aartselaar, Belgium). The control animals of group 3 received no vaccine. Vaccination was performed at the age of 6 weeks. At the age of 8 weeks, all animals were aerogenically infected using a Cirrus™ nebulizer (2-5 µm aërosol particle size; Laméris, Aartselaar, Belgium). The experimental infection dose in each isolator was $10^6$ $TCID_{50}$. Animals were euthanized at 10 days post infection (dpi).

TABLE 9

Vaccination scheme.

| Group | n | Vaccination (week 6) | Epitope | Dose |
|---|---|---|---|---|
| 1 | 6 | Peptides X, Y and Z | B + CD4Th2 CD8 + CD4Th1 | 500 µg/peptide/animal |
| 2a | 3 | Peptide X | CD8 + CD4Th1 | 500 µg/animal |
| 2b | 3 | Peptides Y + Z | B + CD4Th2 | 500 µg/peptide/animal |
| 3 | 6 | Non-vaccinated control | / | / |

5.1. Monitoring and Sampling

Clinical signs were monitored daily until necropsy at 10 dpi.

Blood samples for the detection of MOMP-specific serum antibody titres were collected prior to vaccination, at the day of challenge and at euthanasia at 10 dpi. Blood samples were stored overnight at room temperature, centrifuged (325×g, 10 min, 4° C.) and afterwards serum was collected and stored at −20° C.

At the time of euthanasia, 10 days p.i., all turkeys were examined for gross lesions. Impression smears (cytology) of the lungs and spleen were examined for the presence of chlamydial antigen.

All animals of the control group 3 showed conjunctivitis, rhinitis and moderate dyspnoea. Symptoms were most severe from 8 to 10 dpi. No clinical signs were observed in the vaccinated groups 1 or 2.

The control animals showed severe congestion of the conjunctiva, sometimes only unilaterally, severe congestion of the conchae, moderate congestion of the trachea, bilateral congestion of the lungs with few grew foci surrounded by a hyperaemic zone (pneumonia), opacity of the airsacs and few fibrin cloths in the abdominal airsac, mostly unilateral and hepatosplenomegaly. Group 1, immunized with peptides X, Y and Z showed no macroscopic lesions. Group 2a, immunized with peptide X, showed slight (2 of 3 chickens) to strong (1 of 3 chickens) congestion of the lungs, slight congestion of the serosa of the small intestine (especially the duodenum) and in one of 3 chickens serous pericarditis was observed. The animals of group 2b, immunized with peptides Y and Z only showed slight (1 of 3 chickens) to strong (2 of 3 chickens) congestion of the lungs. No other lesions were observed.

5.2. *Chlamydia* Replication in Lungs and Spleen

Impression smears (cytology) of the lungs and spleen were examined for *C. psittaci* replication by the IMAGEN™ immunofluorescence staining (IMAGEN™ *CHLAMYDIA*, Oxoid, Drongen, Belgium), as previously described (Vanrompay et al., 1992). *C. psittaci* positive cells were enumerated in five randomly selected microscopic fields (400×, Nikon Eclipse TE2000-E, Japan) and scored between 0 and 5: score 0 indicated no *C. psittaci* present; score 1 was given when a mean of 1-5 elementary bodies (infectious, non-metabolic morphological form) was present; score 2, 3, 4 and 5 were given when a mean of 1-5, 6-10, 10-20 and >20 inclusion (actively replicating organisms) positive cells was present.

The results for *C. psittaci* replication in the lungs and spleen, at 10 dpi, are shown in Table 10.

TABLE 10

Scores for *chlamydia* replication in the lungs and the spleen at 10 dpi.

| Group | Chicken number | Lungs | Spleen | Avg score/bird |
|---|---|---|---|---|
| 1 | 1 | 2 | 1 | 8 |
|  | 2 | 0 | 0 |  |
|  | 3 | 1 | 1 |  |
|  | 4 | 1 | 0 |  |
|  | 5 | 0 | 0 |  |
|  | 6 | 1 | 1 |  |
| 2a | 1 | 2 | 2 | 18 |
|  | 2 | 2 | 2 |  |
|  | 3 | 1 | 1 |  |
| 2b | 1 | 2 | 2 |  |
|  | 2 | 1 | 1 |  |
|  | 3 | 1 | 1 |  |
| 3 | 1 | 3 | 3 | 32 |
|  | 2 | 3 | 2 |  |
|  | 3 | 3 | 3 |  |
|  | 4 | 2 | 3 |  |
|  | 5 | 2 | 3 |  |
|  | 6 | 3 | 2 |  |

5.3. Antibody Responses

Enzyme-linked immunosorbent assays (ELISA's) were performed on the serum samples that first were pretreated with kaolin to remove background activity (Novak et al., 1993). Antibody titers were determined using standard protocols with rMOMP as antigen coated on the plates (Verminnen et al., 2006). Recombinant MOMP was produced in COS-7 cells, transiently transfected with pcDNA1::MOMP, as described previously (Vanrompay et al., 1998). Dilutions (1/1000) of, anti-chicken/turkey IgG, anti-chicken/turkey IgM and anti-chicken/turkey IgA (Betyl Lab Inc, Montgomery, USA) were used. Anti-MOMP immunoglobulin titers were presented as the reciprocal of the highest serum dilution that gave an optical density (OD405) above the cut-off value (mean OD off sero-negative SPF turkeys±twice the S.D.). Also, a positive and negative control serum, obtained from previous vaccination experiments, was used. Starting dilution was 1/32.

MOMP specific IgA, IgM, IgG serum antibody titers were determined by the recombinant MOMP-based ELISA (Verminnen et al., 2006) (Table 11). All SPF chickens tested sero-negative at the age of 6 weeks, at the beginning of our experiment.

TABLE 11

Serum IgM, IgG and IgA titers

| Group | Chicken number | Challenge |  |  | Euthanasia |  |  |
|---|---|---|---|---|---|---|---|
|  |  | IgA | IgM | IgG | IgA | IgM | IgG |
| 1 | 1 | 32 | 32 | 64 | 64 | 128 | 256 |
|  | 2 | 0 | 32 | 64 | 32 | 64 | 256 |
|  | 3 | 0 | 32 | 0 | 32 | 32 | 128 |
|  | 4 | 32 | 32 | 64 | 64 | 64 | 256 |
|  | 5 | 0 | 0 | 0 | 32 | 32 | 64 |
|  | 6 | 0 | 32 | 0 | 32 | 64 | 128 |
| 2a | 1 | 0 | 32 | 32 | 32 | 128 | 256 |
|  | 2 | 0 | 0 | 0 | 32 | 64 | 32 |
|  | 3 | 0 | 0 | 0 | 0 | 64 | 32 |
| 2b | 1 | 32 | 64 | 32 | 64 | 64 | 128 |
|  | 2 | 32 | 32 | 0 | 64 | 128 | 256 |
|  | 3 | 0 | 32 | 0 | 32 | 128 | 64 |
| 3 | 1 | 0 | 0 | 0 | 32 | 128 | 128 |
|  | 2 | 0 | 0 | 0 | 0 | 128 | 64 |
|  | 3 | 0 | 0 | 0 | 32 | 256 | 64 |
|  | 4 | 0 | 0 | 0 | 0 | 128 | 64 |
|  | 5 | 0 | 0 | 0 | 0 | 128 | 128 |
|  | 6 | 0 | 0 | 0 | 32 | 256 | 128 |

Conclusion Vaccination Trial 2

Chickens immunized with a combination of B cell+CD4Th2 epitopes of MOMP together with a combination of CD8+ a CD4Th1 epitopes of MOMP (group 1) were better protected than non-immunized controls (group 3). Group 1 was also better protected than chickens immunized with either a combination of only B cell+CD4Th2 epitopes (group 2b) or a combination of only CD8+CD4Th1 epitopes (group 2a).

Example 2

C. psittaci Recombinant MOMP Vaccination Experiment

Materials and Methods
Chlamydia psittaci Strain

C. psittaci strain 92/1293, isolated from a severe outbreak of respiratory disease in a commercial broiler turkey farm in the Netherlands, was used (Vanrompay et al., 1993). The strain was isolated from a pooled homogenate of the lungs, the cloacae and the spleens of diseased turkeys and was characterized as serovar D and genotype D (Geens et al., 2005). Bacteria were grown in Buffalo Green Monkey (BGM) cells as previously described (Vanrompay et al., 1992) and the titration was performed by the method of Spearman and Kaerber (Mayr et al., 1974).

Recombinant MOMP Vaccine

Recombinant MOMP was produced in COS-7 cells transfected with the pcDNA1::MOMP plasmid, as previously described (Vanrompay et al., 1998). The plasmid contained the full-length ompA gene of C. psittaci strain 92/1293. After harvesting the recombinant MOMP (rMOMP), the protein concentration was determined using the bicinchoninic acid protein assay (Sigma).

Vaccination Trial

Experiments were performed in negative pressure isolators (IM 1500, Montair Sevenum, the Netherlands). The experimental design was evaluated and approved by the Ethical Commission for Animal Experiments of Ghent University. To evaluate the C. psittaci rMOMP vaccine, 10 specific pathogen free (SPF) turkeys (CNEVA, Ploufragan, France) were divided into two groups. The vaccination scheme is presented in Table 12. The vaccinated group received 500 µg rMOMP per animal. The vaccine was administered as an aerosol using the Cirrus™ nebulizer (2-5 µm aërosol particle size; Laméris, Aartselaar, Belgium). The control animals received no vaccine. Vaccination was performed on day 1 and at the age of 3 weeks. At the age of 5 weeks, all animals were aerogenically infected using a Cirrus™ nebulizer (2-5 µm aërosol particle size; Laméris, Aartselaar, Belgium). The experimental infection dose in each isolator was $10^6$ $TCID_{50}$.

TABLE 12

Vaccination scheme

| Group | n | Primo vaccination (day 1) and Booster vaccination (week 3) | Dose |
|---|---|---|---|
| 1 | 5 | rMOMP aerosol | 500 µg/animal |
| 2 | 5 | Non-vaccinated control | / |

Monitoring and Sampling

Clinical signs were scored daily until necropsy. Clinical score 0 indicated no clinical signs; score 1: conjunctivitis; score 2: rhinitis; score 3: dyspnoea; score 4: conjunctivitis and rhinitis; score 5: conjunctivitis and dyspnoea; score 6: rhinitis and dyspnoea; score 7: conjunctivitis, rhinitis and dyspnoea.

Pharyngeal and cloacal excretion of C. psittaci was monitored on day 1 and on every other day starting at 5 days post infection (p.i.) until necropsy at 21 days p.i., using rayon-tipped, aluminium shafted swabs (Colpan; Fiers, Kuurne, Belgium) provided with C. psittaci transport medium (sucrose 74.6 g/l (Acros Organics, Geel, Belgium); $KH_2PO_4$ 5.1 g/l and $K_2HPO_4$ 1.2 g/l (Sigma); L-glutamic acid mono potassium salt 0.9 g/l (Invitrogen, Merelbeke, Belgium) and fetal calf serum 10% v/v (Greiner, Wemmel, Belgium); gentamycin 50 µg/ml (Invitrogen); vancomycin 100 µg/ml and streptomycin 100 µg/ml (Soenen, Merelbeke, Belgium); nystatin 25000 U/ml (Sigma) pH 7). Swabs were stored at −80° C. until processed.

Blood samples for the detection of MOMP-specific serum antibody titres were collected prior to each vaccination, 7 days following the booster vaccination, immediately prior to the experimental infection and at 14 and 21 days p.i. Blood samples were stored overnight at room temperature, centrifuged (325×g, 10 min, 4° C.) and afterwards serum was collected and stored at −20° C.

At the time of euthanasia, 21 days p.i., proliferative responses in peripheral blood lymphocytes were examined and characterized. All turkeys were examined for gross lesions. The score system is presented in Table 13. Cryostat tissue sections of the lungs, thoracic and abdominal airsacs, the pericardium, liver and spleen were examined for the presence of chlamydial antigen.

TABLE 13

Scores for *C. psittaci* macroscopic lesions in turkeys

| Tissue | Score 1 | Score 2 | Score 3 |
|---|---|---|---|
| Lungs | Slightly congested | Severely congested | Grey foci |
| Thoracic air sacs | Diffuse opacity | Focal fibrin deposits | Severe fibrinous airsacculitis |
| Abdominal air sacs | Diffuse opacity | Few fibrin deposits | Severe fibrinous airsacculitis |
| Pericardium | Serous pericarditis | Sero-fibrinous pericarditis | Fibrinous adhesive pericarditis |
| Spleen | Slightly enlarged | Moderately enlarged | Severely enlarged |
| Liver | Slightly enlarged | Moderately enlarged | Severely enlarged |

*Chlamydia* Replication in Tissues and Bacterial Excretion

Cryostat tissue sections (5 µm) of the conchae, the conjunctivae, the trachea, the lungs, thoracic and abdominal airsacs, the pericardium, liver and spleen were examined for *C. psittaci* replication by the IMAGEN™ immunofluorescence staining (IMAGEN™ *CHLAMYDIA*, Oxoid, Drongen, Belgium), as previously described (Vanrompay et al., 1994). *C. psittaci* positive cells were enumerated in five randomly selected microscopic fields (400×, Nikon Eclipse TE2000-E, Japan) and scored between 0 and 5: score 0 indicated no *C. psittaci* present; score 1 was given when a mean of 1-5 elementary bodies (infectious, non-metabolic morphological form) was present; score 2, 3, 4 and 5 were given when a mean of 1-5, 6-10, 10-20 and >20 inclusion (actively replicating organisms) positive cells was present.

All swabs were examined for *C. psittaci* excretion by bacterial culture in Buffalo Green Monkey (BGM) cells (Vanrompay et al., 1992) and subsequent chlamydial identification using the IMAGEN™ direct immunofluorescence assay (Vanrompay et al., 1992). The presence of *C. psittaci* was scored as for bacterial replication in different tissues.

Antibody Responses

Enzyme-linked immunosorbent assays (ELISA's) were performed on the serum samples that first were pretreated with kaolin to remove background activity (Novak et al., 1993). Antibody titers were determined using standard protocols with rMOMP as antigen coated on the plates (Verminnen et al., 2006). Recombinant MOMP was produced in COS-7 cells, transiently transfected with pcDNA1::MOMP, as described previously (Vanrompay et al., 1998). Dilutions of 1/2000 and 1/4000 of, respectively, biotinylated anti-chicken/turkey IgG (H+L) antibody and peroxidase-conjugated streptavidin were used. Anti-MOMP immunoglobulin titers were presented as the reciprocal of the highest serum dilution that gave an optical density (OD405) above the cut-off value (mean OD off sero-negative SPF turkeys±twice the S.D.). Also, a positive and negative control serum, obtained from previous vaccination experiments, was used. Starting dilution was 1/32.

MOMP-specific isotypes in pharyngeal swabs were determined using cross-reactive anti-chicken IgG-, IgM- and IgA specific peroxidase-conjugated polyclonal antibodies (Bethyl Laboratories Inc.). Also, a positive and negative control serum, obtained from previous vaccination experiments, was used. Starting dilution for the mucosal swabs was 1/32.

Lymphocyte Proliferative Responses and Characterization of T Cells

Peripheral blood leukocytes (PBL) were isolated from heparinized blood samples obtained by venepuncture (*V. ulnaris*) from each turkey, at 21 days p.i. Lymphocyte proliferative tests were performed as previously described (Vanrompay et al., 1999). Briefly, non-adherent cells were grown in duplicate in 96-well tissue culture plates at $1 \times 10^6$ cells in 150 µl of DMEM (Invitrogen) supplemented with 20% heat-inactivated fetal calf serum (Greiner), 1% nonessential amino acids, 1% sodium pyruvate, 1% 1-glutamine, 1% gentamycine and 0.1% β-mercaptoethanol (all Invitrogen). For antigen proliferation, 10 µg of recombinant MOMP was added to individual wells. Negative and positive controls included cells stimulated with either plain medium or with 10 µg concanavalin A (Con A), respectively. Cells were incubated at 39.5° C. in a humidified incubator with 5% $CO_2$. Con A or antigen induced proliferation was measured by incorporation of $^3$H-thymidine (1 µCi/well) during at last 16 h of culture, at days 2 (ConA) and 5, respectively. Cultures were harvested onto glass fiber filter strips with a cell harvester (Skatron, Liers, Norway). Filters were counted in a Beckman β-scintillation counter (Beckman, Gent, Belgium). The stimulation index was defined as the ratio of counts per minute (cpm) of stimulated cultures on medium-only cultures.

Proliferating cells were also characterized by flow cytometry with a cross reacting chicken anti-CD4 monoclonal antibody and a turkey anti-CD8 monoclonal antibody.

Statistical Analysis

The Mann-Whitney test will be used for statistical analysis. Results will be considered significantly different at the level of P<0.05.

Results

Clinical Signs

Clinical signs in the rMOMP vaccinated group and the control group are presented in Table 14.

TABLE 14

Clinical signs at different days post infection (p.i.)

| Days p.i. | rMOMP vaccin (n = 5) | Controls (n = 5) |
|---|---|---|
| 4 | Conjunctivitis (2)* | Lethargia, anorexia, Conjunctivitis (5) |
| 7 | Conjunctivitis (2), rhinitis (2) | Conjunctivitis (5), rhinitis (5) |
| 9 | Conjunctivitis (2), rhinitis (2), watery droppings (3) | Conjunctivitis (5) + rhinitis (5) + moderate dyspnee (3) |
| 11 | Conjunctivitis (2), rhinitis (3), Watery droppings (3) | Conjunctivitis (5) + rhinitis (5) + severe dyspnee (5), Watery droppings (3) |
| 13 | Conjunctivitis (2), moderate dyspnee (1) | Conjunctivitis (5) + rhinitis (5) + moderate dyspnee (3), severe dyspnee (2), Watery droppings (5) |
| 15 | Conjunctivitis (2), moderate dyspnee (2) | Conjunctivitis (5) + rhinitis (5) + moderate dyspnee (5), Watery droppings (4) |
| 17 | moderate dyspnee (2) | Conjunctivitis (5), rhinitis (3), moderate dyspnee (2), watery droppings (5), |
| 19 | / | Conjunctivitis (5), rhinitis (3), moderate dyspnee (3), Watery droppings (4) |
| 21 | / | Conjunctivitis (5), rhinitis (3), Watery droppings (2), moderate dyspnee (3) |

*The number of animals with clinical symptoms

Macroscopic Findings

The macroscopic lesions in all animals were evaluated at necropsy (Table 15). Overall, the control animals showed severe congestion of the lungs with inflammatory sites and the air sacs showed a diffuse opacity with large fibrin deposits. Congestion of the conchae and conjunctivae could be observed in these animals and some of them also showed tracheal congestion. Moreover, a serous pericarditis was found in the control animals and also congestion of the liver and the spleen could be visualized.

The vaccinated animals, showed the most severe symptoms in the abdominal air sacs.

*Chlamydia* Replication and Excretion

The results for *C. psittaci* replication in the different tissues, at 21 days p.i., are shown in Table 16. The results of the pharyngeal and cloacal swabs that were analysed for *C. psittaci* excretion are shown in Table 17. All swabs that were taken from the one-day-old turkeys were negative.

Antibody Responses

MOMP IgG (H+L), serum antibody titers were determined performed using our recombinant-MOMP based ELISA (Verminnen et al., 2006). The $\log_{10}$ of the mean values of the antibody titers in function of the age of the turkeys is presented in Table 18.

Mucosal (pharyngeal) swabs taken at the day of the booster vaccination, at the day of the challenge infection and at euthanasia were investigated for the presence of IgG, IgM and IgA antibodies. The results are presented in Table 19.

TABLE 15

Mean scores per group ± S.D. (% positive turkeys) for *C. psittaci* macroscopic lesions on day 21 p.i.

| Group | Conchae | Conjunctivae | Trachea | Lungs | Abdominal air sacs |
|---|---|---|---|---|---|
| rMOMP | 1 ± 0 (100) | 0 ± 0 (0) | 0 ± 0 (0) | 0.40 ± 0.89 (40) | 0.60 ± 0.55 (60) |
| Controls | 1.90 ± 0.55 (80) | 0.50 ± 0.71 (60) | 0.14 ± 0.38 (20) | 1.90 ± 0.55 (80) | 2.20 ± 1.10 (100) |

| Group | Thoracal air sacs | Pericardium | Liver | Spleen | Total score |
|---|---|---|---|---|---|
| rMOMP | 0.20 ± 0.45 (20) | 1 ± 0 (50) | 0 ± 0 (0) | 0.20 ± 0.45 (20) | 3.4 |
| Controls | 1.90 ± 0.55 (100) | 1.80 ± 0.84 (100) | 0.60 ± 0.55 (80) | 1.90 ± 0.55 (80) | 12.84 |

TABLE 16

Mean score per group ± S.D. (% positive turkeys) for the presence of *C. psittaci*.

| Group | Conchae | Conjunctivae | Trachea | Lungs | Abdominal air sacs |
|---|---|---|---|---|---|
| rMOMP | 0.60 ± 0.55 (100) | 1.80 ± 0.84 (20) | 1.0 ± 0 (20) | 0.60 ± 0.55 (40) | 1.90 ± 0 (100) |
| Controls | 2.20 ± 1.10 (100) | 2.20 ± 1.10 (100) | 2.20 ± 1.10 (100) | 2.20 ± 0 (100) | 3.00 ± 1.22 (100) |

| Group | Thoracal air sacs | Pericardium | Liver | Spleen | Total score |
|---|---|---|---|---|---|
| rMOMP | 1.0 ± 0 (80) | 1.00 ± 0 (60) | 0.20 ± 0.45 (20) | 1.00 ± 0.71 (80) | 9.1 |
| Controls | 2.20 ± 0 (100) | 2.20 ± 0 (100) | 1.0 ± 0 (80) | 1.0 ± 0 (80) | 18.2 |

TABLE 17

Mean score per group ± S.D. (% positive turkeys) for pharyngeal and cloacal *C. psittaci* shedding.

| | Pharyngeal excretion | | Cloacal excretion | |
|---|---|---|---|---|
| Days PI | rMOMP | Control | rMOMP | Control |
| 5 | 0.75 ± 0.50 (80) | 1.60 ± 0.0 (100) | 0.00 ± 0.00 (100) | 0.75 ± 0.50 (20) |
| 7 | 1.60 ± 0.89 (80) | 1.80 ± 0.84 (100) | 1.80 ± 0.80 (100) | 1.60 ± 0.89 (40) |
| 9 | 2.0 ± 1.00 (100) | 2.20 ± 1.10 (80) | 2.6 ± 0.9 (100) | 3.0 ± 0 (80) |
| 11 | 2.20 ± 1.10 (100) | 3.00 ± 1.22 (100) | 2.6 ± 0.9 (100) | 2.20 ± 1.10 (100) |
| 13 | 0.80 ± 1.3 (100) | 3.00 ± 1.22 (100) | 1.2 ± 1.1 (100) | 3.00 ± 0.00 (100) |
| 15 | 1.4 ± 0.90 (80) | 3.00 ± 0.00 (100) | 1.2 ± 1.1 (80) | 3.00 ± 0.00 (100) |
| 17 | 1.4 ± 0.90 (80) | 2.20 ± 1.10 (100) | 2.2 ± 1.10 (80) | 3.00 ± 0.00 (100) |
| 19 | 1.00 ± 0.71 (80) | 1.80 ± 0.84 (80) | 1.4 ± 0.9 (60) | 3.00 ± 1.22 (80) |
| 21 | 1.20 ± 1.10 (60) | 2.20 ± 1.10 (100) | 0.80 ± 1.3 (60) | 2.20 ± 1.10 (100) |

TABLE 18

Log₁₀ of mean serum antibody titers

| Group | Preserum | BV[a] | One week PBV[b] | Challenge | 2 weeks PC[c] | Euthanasia |
|---|---|---|---|---|---|---|
| rMOMP | 0 | 1.34 | 2.61 | 2.60 | 2.10 | 2.03 |
| Controls | 0 | 0 | 0 | 0 | 1.86 | 2.08 |

[a]BV, booster vaccination.
[b]PBV, post booster vaccination.
[c]PC, post challenge

TABLE 19

Mean OD value per group for IgA, IgM and IgG in pharyngeal swabs

| Group | BV[a] | Challenge | Euthanasia |
|---|---|---|---|
| rMOMP | | | |
| IgA | 0 | 0 | 0.100 |
| IgM | 0.124 | 0.111 | 0.152 |
| IgG | 0.110 | 0.107 | 0.122 |
| Controls | | | |
| IgA | 0 | 0 | 0.166 |
| IgM | 0 | 0 | 0.197 |
| IgG | 0 | 0 | 0.185 |

[a]BV, booster vaccination.

Antigen-Specific Lymphocyte Proliferation and Characterization of T Cells

The proliferative response of the peripheral blood lymphocytes after stimulation with recombinant MOMP of all vaccinated and control animals was determined on day 21 p.i. (Table 20).

The lymphocytes of the rMOMP vaccinated group showed a significant higher proliferative response compared to the control group.

TABLE 20

Proliferative response of the peripheral blood lymphocytes on day 21 p.i.

| Group | Mean stimulation-index (S.I.) ± S.D. |
|---|---|
| rMOMP | 4. ± 0.00 |
| Control | 1.30 ± 0.21 |

The proliferating cells were also characterized by flow cytometry with a cross-reacting chicken anti-CD4 monoclonal antibody and a turkey anti-CD8 monoclonal antibody. Results are shown in Table 21.

TABLE 21

Lymphocyte CD4/CD8 characterization on day 21 p.i.

| Group | Mean CD4/CD8 score ± S.D. |
|---|---|
| rMOMP | 1.15 ± 0.31 |
| Control | 0.74 ± 0.29 |

CONCLUSION

Vaccination with the full-length recombinant MOMP was significantly less protective than the use of a combination of B and T cell epitopes of the MOMP (groups 4 and 6 of vaccination trial 1, and group 1 of vaccination trial 2 (vac.2) of the experiments in example 1) as:

1) Clinical signs in rMOMP vaccinated animals were significantly more severe than in animals of groups 4, 6 and 1 (vac.2). rMOMP vaccinated animals showed conjunctivitis, rhinitis, watery droppings and moderate dyspnee during the experiment. Animals of group 4 showed only conjunctivitis and rhinitis while the animals of group 6 and 1 (vac.2) stayed healthy. rMOMP vaccinated animals became healthy at 19 days p.i., while clinical signs in group 4 already disappeared at 8 days p.i.

2) Macroscopic lesions were observed in 60% of the rMOMP immunized animals and in 6 of 9 (67%) examined tissues. Lesions were most severe in the abdominal airsacs. For group 4, gross pathology was only present in 2 of 7 (28%) animals and in 1 of 10 (10%) examined tissues, namely the lung. For group 6, gross pathology was only present in 1 of 8 (12.5%) animals and like for group 4 only in 1 of 10 (10%) examined tissues, namely the lung. Group 1 (vac.2) showed no macroscopic lesions.

3) Bacterial excretion. Pharyngeal and cloacal excretion in rMOMP vaccinated animals was higher than in groups 4 and 6.

4) Replication of C. psittaci in internal organs. (see Table 22)

Animals receiving rMOMP twice were less protected than the ones receiving the peptide combinations once (group 4) or twice (group 6). The maximum number of animals with a C. psittaci positive tissue was 50%, 57% and 100% for respectively group 6, 4 and the rMOMP-vaccinated group. The maximum score for C. psittaci replication in tissues was 0.38, 0.57 and 1.90 for respectively group 6, 4 and the rMOMP-vaccinated group. For vac 2, group 1 was best protected as demonstrated by the immunofluorescence staining on impression smears of the lungs and the spleen.

The highest protection (achieved in group 6) level was correlated with a significant higher mucosal IgA titer at the day of challenge and a higher lymphocyte proliferative response of especially spleen lymphocytes at 21 days post infection.

rMOMP vaccination gave no significant difference for the CD4/CD8 ratio in peripheral blood as compared to the controls, while the peptide combination (group 4 and 6) gave a significantly higher CD4/CD8 than the controls at any time point post infection. For group 1 (vac. 2), protection was correlated with a higher number of animals showing IgG serum antibodies at the day of challenge.

TABLE 22

Mean scores per group ± standard deviation (% positive animals) for the presence of C. psittaci in several organs on day 21 p.i.

| Tissue | Group 1 | Group 2 | Group 3 | Group 4 | Group 5 | Group 6 | rMOMP (twice) |
|---|---|---|---|---|---|---|---|
| Conjunctivae | 1.07 ± 0.19 (100) | 0.50 ± 0.29 (86) | 0.50 ± 0.41 (71) | 0.29 ± 0.49 (29) | 0.86 ± 0.24 (100) | 0.13 ± 0.35 (13) | 0.60 ± 0.55 (100) |

TABLE 22-continued

Mean scores per group ± standard deviation (% positive animals)
for the presence of *C. psittaci* in several organs on day 21 p.i.

| Tissue | Group 1 | Group 2 | Group 3 | Group 4 | Group 5 | Group 6 | rMOMP (twice) |
|---|---|---|---|---|---|---|---|
| Conchae | 1.00 ± 0.29 (100) | 0.29 ± 0.39 (43) | 0.86 ± 0.99 (86) | 0.50 ± 0.50 (57) | 0.93 ± 0.19 (100) | 0.06 ± 0.18 (13) | 1.80 ± 0.84 (20) |
| Sinus | 0.79 ± 0.49 (86) | 0.57 ± 0.53 (57) | 0.36 ± 0.38 (57) | 0.36 ± 0.48 (43) | 0.79 ± 0.27 (100) | 0.25 ± 0.27 (50) | / |
| Trachea | 1.14 ± 0.38 (100) | 0.43 ± 0.35 (71) | 0.50 ± 0.29 (86) | 0.29 ± 0.49 (29) | 1.14 ± 0.24 (100) | 0.25 ± 0.38 (38) | 1.00 ± 0 (20) |
| Lungs | 1.36 ± 0.38 (100) | 0.57 ± 0.35 (86) | 0.50 ± 0.41 (71) | 0.43 ± 0.73 (43) | 1.57 ± 0.79 (100) | 0.38 ± 0.44 (50) | 0.60 ± 0.55 (40) |
| Thoracal air sacs | 0.93 ± 0.35 (100) | 0.14 ± 0.24 (29) | 0.21 ± 0.27 (43) | 0.29 ± 0.49 (29) | 1.21 ± 0.64 (100) | 0.13 ± 0.23 (25) | 1.00 ± 0 (80) |
| Abdominal air sacs | 1.14 ± 0.48 (100) | 0.64 ± 1.11 (43) | 0.64 ± 0.38 (86) | 0.07 ± 0.19 (14) | 1.21 ± 0.39 (100) | 0.13 ± 0.35 (13) | 1.90 ± 0 (100) |
| Pericardium | 0.64 ± 0.24 (100) | 0.36 ± 0.38 (57) | 0.43 ± 0.19 (86) | 0.14 ± 0.38 (14) | 0.50 ± 0.50 (57) | 0.00 ± 0.00 (0) | 1.00 ± 0 (60) |
| Spleen | 1.71 ± 0.95 (86) | 0.14 ± 0.37 (14) | 1.57 ± 1.17 (86) | 0.57 ± 0.98 (29) | 1.71 ± 0.76 (100) | 0.38 ± 0.69 (38) | 1.00 ± 0.71 (80) |
| Liver | 0.29 ± 0.57 (29) | 0.00 ± 0.00 (0) | 0.14 ± 0.24 (29) | 0.21 ± 0.39 (29) | 0.36 ± 0.48 (43) | 0.13 ± 0.35 (13) | 0.20 ± 0.45 (20) |

REFERENCES

Annunziato F, Romagnani S., 2009. Do studies in humans better depict Th17 cells? Blood., 10; 114(11):2213-9.

Beatty P R, Rasmussen S J, Stephens R S. Cross-reactive cytotoxic T-lymphocyte-mediated lysis of *Chlamydia trachomatis* and *Chlamydia psittaci*-infected cells. Infect Immun 1997; 65:951-6.

Cotter T W, Ramsey K H, Miranpuri G S, Poulsen Ch E, Byrne G I. Dissemination of *Chlamydia trachomatis* chronic genital tract infection in gamma interferon gene knockout mice. Infect Immun 1997; 65:2145-52.

Cotter T W, Meng Q, Shen Z-L, Zhang Y-X, Su H, Caldwell H D. Protective efficacy of major outer membrane protein-specific immuno-globulin A (IgA) and IgG monoclonal antibodies in a murine model of *Chlamydia trachomatis* genital tract infection. Infect Immun 1995; 63:4704-14.

Geens, T., Dewitte, A., Boon, N., Vanrompay D. (2005). Development of a *Chlamydophila psittaci* species-specific and genotype-specific real-time PCR. Vet. Res. 36, 787-797.

Gerdts W., Mutwiri G. K., Tikoo S. K., Babiuk L. A., 2006. Mucosal delivery of vaccines in domestic animals, Vet. Res. 37: 487-510

Johansson M, Schön K, Ward M, Lycke N. Genital tract infection with *Chlamydia trachomatis* fails to induce protective immunity in gamma interferon receptor-deficient mice despite a strong local immunoglobulin A response. Infect Immun, 1997; 65:1032-44.

Kelly K A. Cellular immunity and *Chlamydia* genital infection: induction, recruitment, and effector mechanisms. Int Rev Immunol. 2003 January-February; 22(1):3-41.

Ladant, D., and Ullmann A. (1999). *Bordetella pertussis* adenylaat cyclase: a toxin with multiple talents. Trends in Microbiology, 7, 172-176.

Longbottom, D. & Livingstone, M. (2006). Vaccination against chlamydial infections of man and animals. *Vet J* 171: 263-275.

Lynagh G R, Bailey M, Kaiser P. Interleukin-6 is produced during both murine and avian Eimeria infections. Vet Immunol Immunopathol. 2000 Aug. 31; 76(1-2):89-102.

Mayr, A., Bachmann, P. A., Bibrack, B., Wittmann, G. (1974). Quantitative bestimmung der virusinfektiosität. In: Mayr, A., Bachmann, P. A., Bibrack, B., Wittmann, G. (Eds.), Virologische arbeitsmethoden Bd.I., Gustav Fisher Verlag, Jena, pp. 35-39.

Morrison, S. G., Su, H., Caldwell, H. D. & Morrison, R. P. (2000). Immunity to murine *Chlamydia trachomatis* genital tract reinfection involves B cells and CD4(+) T cells but not CD8(+) T cells. *Infect Immun* 68: 6979-6987.

Murphy D M, Forrest I A, Corris P A, Johnson G E, Small T, Jones D, Fisher A J, Egan J J, Cawston T E, Ward C, Lordan J L., 2008. Simvastatin attenuates release of neutrophilic and remodeling factors from primary bronchial epithelial cells derived from stable lung transplant recipients. Am J Physiol Lung Cell Mol Physiol., 294(3):L592-9.

Novak, M., Moldoveanu, Z., Schafer, D. P., Mestecky, J., Compans, R. W., 1993. Murine model for evaluation of protective immunity to influenza virus. Vaccine 11, 55-60.

Pal S, Theodor I, Peterson E M, de la Maza L M. Immunization with an acellular vaccine consisting of the outer membrane complex of *Chlamydia trachomatis* induces protection against a genital challenge. Infect. Immun., August 1997, 3361-3369, Vol 65, No. 8

Sandbulte J, TerWee J, Wigington K, Sabara M. Evaluation of *C. psittaci* subfraction and subunit preparations for their protective capacities. Vet Microbiol. 1996 February; 48(3-4):269-82.

Su H, Caldwell H D. CD4+ T cells play a significant role in adoptive immunity to *Chlamydia trachomatis* infection of the mouse genital tract. Infect Immun 1995; 63:3302-8.

Su H, Feilzer K, Caldwell H D, Morrison R P. *Chlamydia trachomatis* genital tract infection of antibody-deficient gene knockout mice. Infect Immun 1997; 65:1993-9.

Tan et al. Protection of sheep against *Chlamydia psittaci* infection with a subcellular vaccine containing the major outer membrane protein. Infection and immunity, 1990 p 3101-3108.

Vanrompay, D., Ducatelle, R., Haesebrouck, F., 1992. Diagnosis of avian chlamydiosis: specificity of the modified Giménez staining on smears and comparison of the sensitivity of isolation in eggs and three different cell cultures. Zentralbl. Veterinarmed. B 39, 105-112.

Vanrompay, D., Ducatelle, R., Haesebrouck, F., Hendrickx, W. (1993). Primary pathogenicity of an European isolate of *Chlamydia psittaci* from turkey poults. Vet. Microbiol. 38, 103-113.

Vanrompay, D., Ducatelle, R., Haesebrouck, F., 1994a. Pathogenicity for turkeys of *C. psittaci* strains belonging to the avian serovars A, B and D. Avian Pathol. 23, 247-262.

Vanrompay, D., Van Nerom, A., Ducatelle, R., Haesebrouck, F., 1994b. Evaluation of five immunoassays for detection of *C. psittaci* in cloacal and conjunctival specimens from turkeys. J. Clin. Microbiol. 32, 1470-1474.

Vanrompay, D., Cox, E., Mast, J., Goddeeris, B., Volckaert, G., 1998. High-level expression of *C. psittaci* major outer membrane protein in COS cells and in skeletal muscles of turkeys. Infect. Immun. 66, 5494-5500.

Vanrompay, D., Cox, E., Volckaert, G., Goddeeris, B., 1999b. Turkeys are protected from infection with *Chlamydia psittaci* by plasmid DNA vaccination against the major outer membrane protein. Clin. Exp. Immunol. 118, 49-55.

Vanrompay D., J. M. Lyons and S. A. Morré (2005). ANIMAL MODELS FOR THE STUDY OF *CHLAMYDIA TRACHOMATIS* INFECTIONS IN THE FEMALE GENITAL INFECTION. Drugs of Today 2005, 41: 55-63.

Verminnen at al. Protection of turkeys against *Chlamydophila psittaci* challenge by DNA and rMOMP vaccination and evaluation of the immunomodulating effect of 1 alpha,25-dihydroxyvitamin D. Vaccine 23 (2005) 4509-4516.

Verminnen, K., Van Loock, M., Hafez, H. M., Ducatelle, R., Haesebrouck, F., Vanrompay, D., (2006). Evaluation of a recombinant enzyme-linked immunosorbent assay for detecting *C. psittaci* antibodies in turkey sera. Vet. Res. 37, 623-632.

Verminnen et al. Vaccination of turkeys against *Chlamydophila psittaci* through optimised DNA formulation and administration. Vaccine 28 (2010) 3095-3105.

Williams D M, Grubbs B G, Pack E, Kelly K, Rank R G. Humoral and cellular immunity in secondary infection due to murine *Chlamydia trachomatis*. Infect Immun 1997; 65:2876-82.

Zubiaga A M, Munoz E, Merrow M, Huber B T. Regulation of interleukin 6 production in T helper cells. Int Immunol. 1990; 2(11):1047-54.

---

The invention claimed is:

1. A method for eliciting an immune response in a subject against an infection of a species of the genus *Chlamydia* comprising administering a composition comprising one or more peptides, each of said peptides comprising one or more epitopes selected from the group consisting of a B-cell epitope, a CD4+ Th2 cell epitope, a CD4+ Th1 cell epitope and a CTL epitope; wherein said composition comprises at least a B-cell epitope, a CD4+ Th2 cell epitope, a CD4+ Th1 cell epitope and a CTL epitope, wherein the epitopes are located in the major outer membrane protein (MOMP) of *Chlamydia psittaci*, wherein the composition does not comprise the full-length *Chlamydia* MOMP protein, and wherein at least one of the epitopes is located in the CS1-VS1-CS2-VS2-CS3 domain of the MOMP.

2. A method of treating, reducing the symptoms and/or clinical signs of, or reducing the risk for an infection of a species of the genus *Chlamydia* comprising administering a composition comprising one or more peptides, each of said peptides comprising one or more epitopes selected from the group consisting of a B-cell epitope, a CD4+Th2 cell epitope, a CD4+ Th1 cell epitope and a CTL epitope; wherein said composition comprises at least a B-cell epitope, a CD4+ Th2 cell epitope, a CD4+ Th1 cell epitope and a CTL epitope, wherein the epitopes are located in the major outer membrane protein (MOMP) of *Chlamydia psittaci*, wherein the composition does not comprise the full-length *Chlamydia* MOMP protein, and wherein at least one of the epitopes is located in the CS1-VS1-CS2-VS2-CS3 domain of the MOMP.

3. The method according to claim 1, wherein the B-cell epitope consists of an amino acid sequence selected from the group consisting of: GTASATT (SEQ ID NO 92), GTDFNN (SEQ ID NO 93) and NPTLLGKA (SEQ ID NO 94), or a variant thereof having at least 80% sequence identity thereto, and wherein the CD4+ Th2 cell epitope, the CD4+Th1 cell epitope and the CTL epitope independently consist of an amino acid sequence selected from the group consisting of SEQ ID NO 20 and 101-117, or a variant thereof having at least 80% sequence identity thereto.

4. The method according to claim 2, wherein:
the B-cell epitope comprises an amino acid sequence selected from the group consisting of GTASATT (SEQ ID NO 92), GTDFNN (SEQ ID NO 93) and NPTLLGKA (SEQ ID NO 94), or a variant thereof having at least 80% sequence identity thereto;
the peptide comprising a CD4+ Th2 cell epitope is selected from the group consisting of SEQ ID NO 7, 8, 43, 76, 77, 85, and 91, or a variant thereof having at least 80% sequence identity thereto;
the peptide comprising a CTL (CD8+) epitope is selected from the group consisting of: SEQ ID NO 20, 26, 27, 42, 43, 61, 73, 75, and 80, or a variant thereof having at least 80% sequence identity thereto; and
the peptide comprising a CD4+ Th1 cell epitope is selected from the group consisting of SEQ ID NO 1, 10-13, 18, 20, 25, 27, 29, 31-32, 35, 42, 46, 51, 53-56, 61, 64, 65-67, 69-73, 75, 79-81, and 87, or a variant thereof having at least 80% sequence identity thereto.

5. The method according to claim 2, wherein the peptide comprising a B-cell epitope and/or a CD4+ Th2 cell epitope is selected from the group consisting of: SEQ ID NO 7, 8, 76, 77, 91 and 94-98, or a variant thereof having at least 80% sequence identity thereto, wherein the peptide comprising a CTL-cell epitope is selected from the group consisting of SEQ ID NO 73, 75, 80 and 99, or a variant thereof having at least 80% sequence identity thereto, and wherein the peptide comprising a CD4+ Th1 cell epitope is selected from the group consisting of SEQ ID NO 70, 71, 73, 75, 79, 80, 81 and 99, or a variant thereof having at least 80% sequence identity thereto.

6. The method according to claim 2, wherein the composition comprises the peptides EPSLLIDGTMWEGASGD- PCDPC (SEQ ID NO 97), TGTASATT (SEQ ID NO 95), KGTDFNNQ (SEQ ID NO 96), AQPKLATAVLDLTTWNPTLLGKATTVDGTNTYSDFL (SEQ ID NO 98), and AATDTKSATLKYHEWQVGLALSYRLNMLVPYIGVNWSRATFDADT (SEQ ID NO 99), or variants thereof having at least 80% sequence identity thereto; or wherein the composition comprises the peptides TWCDAISIRAGYYGD (SEQ ID NO 20), EMLNVTSSPAQFVIH (SEQ ID NO 62), and KGTDFNNQ (SEQ ID NO 96), or variants thereof having at least 80% sequence identity thereto.

7. The method according to claim 1, wherein part or all of the peptides are present as a mixture or are part of a polyepitope construct, said polyepitope construct comprising repetitions of the epitopes and/or wherein the peptides are linked to each other or are separated by a linker or one or more spacer amino acids.

8. The method according to claim 1, wherein the composition comprises a nucleic acid sequence encoding the peptide(s).

9. The method according to claim 1, wherein the composition comprises a nucleic acid sequence encoding the peptide(s).

10. The method according to claim 8, wherein the nucleic acid sequence is part of a vector.

11. The method according to claim 9, wherein the nucleic acid sequence is part of a vector.

12. The method according to claim 1, wherein the composition further comprises an antigen delivery system.

13. The method according to claim 2, wherein the composition further comprises an adjuvant.

14. The method according to claim 2, wherein the composition further comprises a pharmaceutically acceptable excipient.

15. The method according to claim 2, wherein said composition is administered in a prime boost regimen.

16. The method according to claim 2, wherein the B-cell epitope consists of an amino acid sequence selected from the group consisting of: GTASATT (SEQ ID NO 92), GTDFNN (SEQ ID NO 93) and NPTLLGKA (SEQ ID NO 94), or a variant thereof having at least 80% sequence identity thereto, and wherein the CD4+ Th2 cell epitope, the CD4+ Th1 cell epitope and the CTL epitope independently consist of an amino acid sequence selected from the group consisting of SEQ ID NO 20 and 101-117, or a variant thereof having at least 80% sequence identity thereto.

17. The method according to claim 2, wherein part or all of the peptides are present as a mixture or are part of a polyepitope construct comprising repetitions of the epitopes and/or wherein the peptides are linked to each other or are separated by a linker or one or more spacer amino acids.

18. The method according to claim 2, wherein the composition further comprises an antigen delivery system.

19. The method according to claim 1, wherein the composition comprises two or more peptides, each of said peptides comprising the one or more epitopes selected from the group consisting of the B-cell epitope, the CD4+ Th2 cell epitope, the CD4+Th1 cell epitope and the CTL epitope.

20. The method according to claim 19, wherein:
the composition comprises the peptides EPSLLIDGTMWEGASGDPCDPC (SEQ ID NO 97), TGTASATT (SEQ ID NO 95), KGTDFNNQ (SEQ ID NO 96), AQPKLATAVLDLTTWNPTLLGKATTVDGTNTYSDFL (SEQ ID NO 98), and AATDTKSATLKYHEWQVGLALSYRLNMLVPYIGVNWSRATFDADT (SEQ ID NO 99); or
the composition comprises the peptides TWCDAISIRAGYYGD (SEQ ID NO 20), EMLNVTSSPAQFVIH (SEQ ID NO 62), and KGTDFNNQ (SEQ ID NO 96).

21. The method according to claim 10, wherein the vector is a viral vector.

22. The method according to claim 11, wherein the vector is a viral vector.

* * * * *

SEQUENCE LISTING

```
<160> NUMBER OF SEQ ID NOS: 158

<210> SEQ ID NO 1
<211> LENGTH: 15
<212> TYPE: PRT
<213> ORGANISM: Chlamydia psittaci

<400> SEQUENCE: 1

Ala Leu Ser Leu Gln Ala Leu Pro Val Gly Asn Pro Ala Glu Pro
1               5                   10                  15

<210> SEQ ID NO 2
<211> LENGTH: 15
<212> TYPE: PRT
<213> ORGANISM: Chlamydia psittaci

<400> SEQUENCE: 2

Leu Ser Leu Gln Ala Leu Pro Val Gly Asn Pro Ala Glu Pro Ser
1               5                   10                  15

<210> SEQ ID NO 3
<211> LENGTH: 15
<212> TYPE: PRT
<213> ORGANISM: Chlamydia psittaci

<400> SEQUENCE: 3

Val Gly Asn Pro Ala Glu Pro Ser Leu Leu Ile Asp Gly Thr Met
1               5                   10                  15

<210> SEQ ID NO 4
<211> LENGTH: 15
<212> TYPE: PRT
<213> ORGANISM: Chlamydia psittaci

<400> SEQUENCE: 4

Gly Asn Pro Ala Glu Pro Ser Leu Leu Ile Asp Gly Thr Met Trp
1               5                   10                  15

<210> SEQ ID NO 5
<211> LENGTH: 15
<212> TYPE: PRT
<213> ORGANISM: Chlamydia psittaci

<400> SEQUENCE: 5
```

Ala Glu Pro Ser Leu Leu Ile Asp Gly Thr Met Trp Glu Gly Ala
1               5                   10                  15

<210> SEQ ID NO 6
<211> LENGTH: 15
<212> TYPE: PRT
<213> ORGANISM: Chlamydia psittaci

<400> SEQUENCE: 6

Glu Pro Ser Leu Leu Ile Asp Gly Thr Met Trp Glu Gly Ala Ser
1               5                   10                  15

<210> SEQ ID NO 7
<211> LENGTH: 15
<212> TYPE: PRT
<213> ORGANISM: Chlamydia psittaci

<400> SEQUENCE: 7

Ile Asp Gly Thr Met Trp Glu Gly Ala Ser Gly Asp Pro Cys Asp
1               5                   10                  15

<210> SEQ ID NO 8
<211> LENGTH: 15
<212> TYPE: PRT
<213> ORGANISM: Chlamydia psittaci

<400> SEQUENCE: 8

Asp Gly Thr Met Trp Glu Gly Ala Ser Gly Asp Pro Cys Asp Pro
1               5                   10                  15

<210> SEQ ID NO 9
<211> LENGTH: 15
<212> TYPE: PRT
<213> ORGANISM: Chlamydia psittaci

<400> SEQUENCE: 9

Gly Thr Met Trp Glu Gly Ala Ser Gly Asp Pro Cys Asp Pro Cys
1               5                   10                  15

<210> SEQ ID NO 10
<211> LENGTH: 15
<212> TYPE: PRT
<213> ORGANISM: Chlamydia psittaci

<400> SEQUENCE: 10

Trp Glu Gly Ala Ser Gly Asp Pro Cys Asp Pro Cys Ala Thr Trp
1               5                   10                  15

<210> SEQ ID NO 11
<211> LENGTH: 15
<212> TYPE: PRT
<213> ORGANISM: Chlamydia psittaci

<400> SEQUENCE: 11

Glu Gly Ala Ser Gly Asp Pro Cys Asp Pro Cys Ala Thr Trp Cys
1               5                   10                  15

<210> SEQ ID NO 12
<211> LENGTH: 15
<212> TYPE: PRT
<213> ORGANISM: Chlamydia psittaci

<400> SEQUENCE: 12

Gly Ala Ser Gly Asp Pro Cys Asp Pro Cys Ala Thr Trp Cys Asp
1               5                   10                  15

<210> SEQ ID NO 13
<211> LENGTH: 15
<212> TYPE: PRT
<213> ORGANISM: Chlamydia psittaci

<400> SEQUENCE: 13

Ala Ser Gly Asp Pro Cys Asp Pro Cys Ala Thr Trp Cys Asp Ala
1               5                   10                  15

<210> SEQ ID NO 14
<211> LENGTH: 15
<212> TYPE: PRT
<213> ORGANISM: Chlamydia psittaci

<400> SEQUENCE: 14

Ser Gly Asp Pro Cys Asp Pro Cys Ala Thr Trp Cys Asp Ala Ile
1               5                   10                  15

<210> SEQ ID NO 15
<211> LENGTH: 15
<212> TYPE: PRT
<213> ORGANISM: Chlamydia psittaci

<400> SEQUENCE: 15

Asp Pro Cys Asp Pro Cys Ala Thr Trp Cys Asp Ala Ile Ser Ile
1               5                   10                  15

<210> SEQ ID NO 16
<211> LENGTH: 15
<212> TYPE: PRT
<213> ORGANISM: Chlamydia psittaci

<400> SEQUENCE: 16

Pro Cys Asp Pro Cys Ala Thr Trp Cys Asp Ala Ile Ser Ile Arg
1               5                   10                  15

<210> SEQ ID NO 17
<211> LENGTH: 15
<212> TYPE: PRT
<213> ORGANISM: Chlamydia psittaci

<400> SEQUENCE: 17

Cys Asp Pro Cys Ala Thr Trp Cys Asp Ala Ile Ser Ile Arg Ala
1               5                   10                  15

<210> SEQ ID NO 18
<211> LENGTH: 15
<212> TYPE: PRT
<213> ORGANISM: Chlamydia psittaci

<400> SEQUENCE: 18

Asp Pro Cys Ala Thr Trp Cys Asp Ala Ile Ser Ile Arg Ala Gly
1               5                   10                  15

<210> SEQ ID NO 19
<211> LENGTH: 15
<212> TYPE: PRT
<213> ORGANISM: Chlamydia psittaci

<400> SEQUENCE: 19

Pro Cys Ala Thr Trp Cys Asp Ala Ile Ser Ile Arg Ala Gly Tyr
1               5                   10                  15

-continued

```
<210> SEQ ID NO 20
<211> LENGTH: 15
<212> TYPE: PRT
<213> ORGANISM: Chlamydia psittaci

<400> SEQUENCE: 20

Thr Trp Cys Asp Ala Ile Ser Ile Arg Ala Gly Tyr Tyr Gly Asp
1               5                   10                  15

<210> SEQ ID NO 21
<211> LENGTH: 15
<212> TYPE: PRT
<213> ORGANISM: Chlamydia psittaci

<400> SEQUENCE: 21

Trp Cys Asp Ala Ile Ser Ile Arg Ala Gly Tyr Tyr Gly Asp Tyr
1               5                   10                  15

<210> SEQ ID NO 22
<211> LENGTH: 15
<212> TYPE: PRT
<213> ORGANISM: Chlamydia psittaci

<400> SEQUENCE: 22

Cys Asp Ala Ile Ser Ile Arg Ala Gly Tyr Tyr Gly Asp Tyr Val
1               5                   10                  15

<210> SEQ ID NO 23
<211> LENGTH: 15
<212> TYPE: PRT
<213> ORGANISM: Chlamydia psittaci

<400> SEQUENCE: 23

Ile Ser Ile Arg Ala Gly Tyr Tyr Gly Asp Tyr Val Phe Asp Arg
1               5                   10                  15

<210> SEQ ID NO 24
<211> LENGTH: 15
<212> TYPE: PRT
<213> ORGANISM: Chlamydia psittaci

<400> SEQUENCE: 24

Ser Ile Arg Ala Gly Tyr Tyr Gly Asp Tyr Val Phe Asp Arg Val
1               5                   10                  15

<210> SEQ ID NO 25
<211> LENGTH: 15
<212> TYPE: PRT
<213> ORGANISM: Chlamydia psittaci

<400> SEQUENCE: 25

Ile Arg Ala Gly Tyr Tyr Gly Asp Tyr Val Phe Asp Arg Val Leu
1               5                   10                  15

<210> SEQ ID NO 26
<211> LENGTH: 15
<212> TYPE: PRT
<213> ORGANISM: Chlamydia psittaci

<400> SEQUENCE: 26

Arg Ala Gly Tyr Tyr Gly Asp Tyr Val Phe Asp Arg Val Leu Lys
1               5                   10                  15

<210> SEQ ID NO 27
<211> LENGTH: 15
```

```
<212> TYPE: PRT
<213> ORGANISM: Chlamydia psittaci

<400> SEQUENCE: 27

Gly Asp Tyr Val Phe Asp Arg Val Leu Lys Val Asp Val Asn Lys
1               5                   10                  15

<210> SEQ ID NO 28
<211> LENGTH: 15
<212> TYPE: PRT
<213> ORGANISM: Chlamydia psittaci

<400> SEQUENCE: 28

Asp Tyr Val Phe Asp Arg Val Leu Lys Val Asp Val Asn Lys Thr
1               5                   10                  15

<210> SEQ ID NO 29
<211> LENGTH: 15
<212> TYPE: PRT
<213> ORGANISM: Chlamydia psittaci

<400> SEQUENCE: 29

Asp Arg Val Leu Lys Val Asp Val Asn Lys Thr Phe Ser Gly Met
1               5                   10                  15

<210> SEQ ID NO 30
<211> LENGTH: 15
<212> TYPE: PRT
<213> ORGANISM: Chlamydia psittaci

<400> SEQUENCE: 30

Arg Val Leu Lys Val Asp Val Asn Lys Thr Phe Ser Gly Met Ala
1               5                   10                  15

<210> SEQ ID NO 31
<211> LENGTH: 15
<212> TYPE: PRT
<213> ORGANISM: Chlamydia psittaci

<400> SEQUENCE: 31

Val Leu Lys Val Asp Val Asn Lys Thr Phe Ser Gly Met Ala Lys
1               5                   10                  15

<210> SEQ ID NO 32
<211> LENGTH: 15
<212> TYPE: PRT
<213> ORGANISM: Chlamydia psittaci

<400> SEQUENCE: 32

Met Ala Lys Ser Pro Thr Glu Ala Thr Gly Thr Ala Ser Ala Thr
1               5                   10                  15

<210> SEQ ID NO 33
<211> LENGTH: 15
<212> TYPE: PRT
<213> ORGANISM: Chlamydia psittaci

<400> SEQUENCE: 33

Glu Ala Thr Gly Thr Ala Ser Ala Thr Thr Thr Ala Val Asp Arg
1               5                   10                  15

<210> SEQ ID NO 34
<211> LENGTH: 15
<212> TYPE: PRT
<213> ORGANISM: Chlamydia psittaci
```

<400> SEQUENCE: 34

Thr Ala Ser Ala Thr Thr Thr Ala Val Asp Arg Thr Asn Leu Ala
1               5                   10                  15

<210> SEQ ID NO 35
<211> LENGTH: 15
<212> TYPE: PRT
<213> ORGANISM: Chlamydia psittaci

<400> SEQUENCE: 35

Ser Ala Thr Thr Thr Ala Val Asp Arg Thr Asn Leu Ala Tyr Gly
1               5                   10                  15

<210> SEQ ID NO 36
<211> LENGTH: 15
<212> TYPE: PRT
<213> ORGANISM: Chlamydia psittaci

<400> SEQUENCE: 36

Ala Thr Thr Thr Ala Val Asp Arg Thr Asn Leu Ala Tyr Gly Lys
1               5                   10                  15

<210> SEQ ID NO 37
<211> LENGTH: 15
<212> TYPE: PRT
<213> ORGANISM: Chlamydia psittaci

<400> SEQUENCE: 37

Asn Leu Ala Tyr Gly Lys His Leu Gln Asp Ala Glu Trp Phe Thr
1               5                   10                  15

<210> SEQ ID NO 38
<211> LENGTH: 15
<212> TYPE: PRT
<213> ORGANISM: Chlamydia psittaci

<400> SEQUENCE: 38

Ala Tyr Gly Lys His Leu Gln Asp Ala Glu Trp Phe Thr Asn Ala
1               5                   10                  15

<210> SEQ ID NO 39
<211> LENGTH: 15
<212> TYPE: PRT
<213> ORGANISM: Chlamydia psittaci

<400> SEQUENCE: 39

Gly Lys His Leu Gln Asp Ala Glu Trp Phe Thr Asn Ala Ala Phe
1               5                   10                  15

<210> SEQ ID NO 40
<211> LENGTH: 15
<212> TYPE: PRT
<213> ORGANISM: Chlamydia psittaci

<400> SEQUENCE: 40

Lys His Leu Gln Asp Ala Glu Trp Phe Thr Asn Ala Ala Phe Leu
1               5                   10                  15

<210> SEQ ID NO 41
<211> LENGTH: 15
<212> TYPE: PRT
<213> ORGANISM: Chlamydia psittaci

<400> SEQUENCE: 41

```
His Leu Gln Asp Ala Glu Trp Phe Thr Asn Ala Ala Phe Leu Ala
1               5                   10                  15

<210> SEQ ID NO 42
<211> LENGTH: 15
<212> TYPE: PRT
<213> ORGANISM: Chlamydia psittaci

<400> SEQUENCE: 42

Trp Phe Thr Asn Ala Ala Phe Leu Ala Leu Asn Ile Trp Asp Arg
1               5                   10                  15

<210> SEQ ID NO 43
<211> LENGTH: 15
<212> TYPE: PRT
<213> ORGANISM: Chlamydia psittaci

<400> SEQUENCE: 43

Trp Asp Arg Phe Asp Ile Phe Cys Thr Leu Gly Ala Ser Asn Gly
1               5                   10                  15

<210> SEQ ID NO 44
<211> LENGTH: 15
<212> TYPE: PRT
<213> ORGANISM: Chlamydia psittaci

<400> SEQUENCE: 44

Ala Ser Asn Gly Tyr Phe Lys Ala Ser Ser Ala Ala Phe Asn Leu
1               5                   10                  15

<210> SEQ ID NO 45
<211> LENGTH: 15
<212> TYPE: PRT
<213> ORGANISM: Chlamydia psittaci

<400> SEQUENCE: 45

Phe Asn Leu Gly Val Leu Ile Gly Leu Lys Gly Thr Asp Phe Asn
1               5                   10                  15

<210> SEQ ID NO 46
<211> LENGTH: 15
<212> TYPE: PRT
<213> ORGANISM: Chlamydia psittaci

<400> SEQUENCE: 46

Asp Phe Asn Asn Gln Leu Pro Asn Val Ala Ile Thr Gln Gly Val
1               5                   10                  15

<210> SEQ ID NO 47
<211> LENGTH: 15
<212> TYPE: PRT
<213> ORGANISM: Chlamydia psittaci

<400> SEQUENCE: 47

Phe Asn Asn Gln Leu Pro Asn Val Ala Ile Thr Gln Gly Val Val
1               5                   10                  15

<210> SEQ ID NO 48
<211> LENGTH: 15
<212> TYPE: PRT
<213> ORGANISM: Chlamydia psittaci

<400> SEQUENCE: 48

Asn Asn Gln Leu Pro Asn Val Ala Ile Thr Gln Gly Val Val Glu
```

<210> SEQ ID NO 49
<211> LENGTH: 15
<212> TYPE: PRT
<213> ORGANISM: Chlamydia psittaci

<400> SEQUENCE: 49

Tyr Thr Asp Thr Thr Phe Ser Trp Ser Val Gly Ala Arg Gly Ala
1               5                   10                  15

<210> SEQ ID NO 50
<211> LENGTH: 15
<212> TYPE: PRT
<213> ORGANISM: Chlamydia psittaci

<400> SEQUENCE: 50

Ala Arg Gly Ala Leu Trp Glu Cys Gly Cys Ala Thr Leu Gly Ala
1               5                   10                  15

<210> SEQ ID NO 51
<211> LENGTH: 15
<212> TYPE: PRT
<213> ORGANISM: Chlamydia psittaci

<400> SEQUENCE: 51

Arg Gly Ala Leu Trp Glu Cys Gly Cys Ala Thr Leu Gly Ala Glu
1               5                   10                  15

<210> SEQ ID NO 52
<211> LENGTH: 15
<212> TYPE: PRT
<213> ORGANISM: Chlamydia psittaci

<400> SEQUENCE: 52

Gly Ala Leu Trp Glu Cys Gly Cys Ala Thr Leu Gly Ala Glu Phe
1               5                   10                  15

<210> SEQ ID NO 53
<211> LENGTH: 15
<212> TYPE: PRT
<213> ORGANISM: Chlamydia psittaci

<400> SEQUENCE: 53

Glu Cys Gly Cys Ala Thr Leu Gly Ala Glu Phe Gln Tyr Ala Gln
1               5                   10                  15

<210> SEQ ID NO 54
<211> LENGTH: 15
<212> TYPE: PRT
<213> ORGANISM: Chlamydia psittaci

<400> SEQUENCE: 54

Cys Gly Cys Ala Thr Leu Gly Ala Glu Phe Gln Tyr Ala Gln Ser
1               5                   10                  15

<210> SEQ ID NO 55
<211> LENGTH: 15
<212> TYPE: PRT
<213> ORGANISM: Chlamydia psittaci

<400> SEQUENCE: 55

Gly Cys Ala Thr Leu Gly Ala Glu Phe Gln Tyr Ala Gln Ser Asn
1               5                   10                  15

```
<210> SEQ ID NO 56
<211> LENGTH: 15
<212> TYPE: PRT
<213> ORGANISM: Chlamydia psittaci

<400> SEQUENCE: 56

Cys Ala Thr Leu Gly Ala Glu Phe Gln Tyr Ala Gln Ser Asn Pro
1               5                   10                  15

<210> SEQ ID NO 57
<211> LENGTH: 15
<212> TYPE: PRT
<213> ORGANISM: Chlamydia psittaci

<400> SEQUENCE: 57

Ala Thr Leu Gly Ala Glu Phe Gln Tyr Ala Gln Ser Asn Pro Lys
1               5                   10                  15

<210> SEQ ID NO 58
<211> LENGTH: 15
<212> TYPE: PRT
<213> ORGANISM: Chlamydia psittaci

<400> SEQUENCE: 58

Thr Leu Gly Ala Glu Phe Gln Tyr Ala Gln Ser Asn Pro Lys Ile
1               5                   10                  15

<210> SEQ ID NO 59
<211> LENGTH: 15
<212> TYPE: PRT
<213> ORGANISM: Chlamydia psittaci

<400> SEQUENCE: 59

Leu Gly Ala Glu Phe Gln Tyr Ala Gln Ser Asn Pro Lys Ile Glu
1               5                   10                  15

<210> SEQ ID NO 60
<211> LENGTH: 15
<212> TYPE: PRT
<213> ORGANISM: Chlamydia psittaci

<400> SEQUENCE: 60

Gly Ala Glu Phe Gln Tyr Ala Gln Ser Asn Pro Lys Ile Glu Met
1               5                   10                  15

<210> SEQ ID NO 61
<211> LENGTH: 15
<212> TYPE: PRT
<213> ORGANISM: Chlamydia psittaci

<400> SEQUENCE: 61

Ala Gln Ser Asn Pro Lys Ile Glu Met Leu Asn Val Thr Ser Ser
1               5                   10                  15

<210> SEQ ID NO 62
<211> LENGTH: 15
<212> TYPE: PRT
<213> ORGANISM: Chlamydia psittaci

<400> SEQUENCE: 62

Glu Met Leu Asn Val Thr Ser Ser Pro Ala Gln Phe Val Ile His
1               5                   10                  15

<210> SEQ ID NO 63
```

```
<211> LENGTH: 15
<212> TYPE: PRT
<213> ORGANISM: Chlamydia psittaci

<400> SEQUENCE: 63

Met Leu Asn Val Thr Ser Ser Pro Ala Gln Phe Val Ile His Lys
1               5                   10                  15

<210> SEQ ID NO 64
<211> LENGTH: 15
<212> TYPE: PRT
<213> ORGANISM: Chlamydia psittaci

<400> SEQUENCE: 64

Val Ile His Lys Pro Arg Gly Tyr Lys Gly Thr Gly Ser Asn Phe
1               5                   10                  15

<210> SEQ ID NO 65
<211> LENGTH: 15
<212> TYPE: PRT
<213> ORGANISM: Chlamydia psittaci

<400> SEQUENCE: 65

Gly Ser Asn Phe Pro Leu Pro Ile Asp Ala Gly Thr Glu Ala Ala
1               5                   10                  15

<210> SEQ ID NO 66
<211> LENGTH: 15
<212> TYPE: PRT
<213> ORGANISM: Chlamydia psittaci

<400> SEQUENCE: 66

Ser Asn Phe Pro Leu Pro Ile Asp Ala Gly Thr Glu Ala Ala Thr
1               5                   10                  15

<210> SEQ ID NO 67
<211> LENGTH: 15
<212> TYPE: PRT
<213> ORGANISM: Chlamydia psittaci

<400> SEQUENCE: 67

Asn Phe Pro Leu Pro Ile Asp Ala Gly Thr Glu Ala Ala Thr Asp
1               5                   10                  15

<210> SEQ ID NO 68
<211> LENGTH: 15
<212> TYPE: PRT
<213> ORGANISM: Chlamydia psittaci

<400> SEQUENCE: 68

Ile Asp Ala Gly Thr Glu Ala Ala Thr Asp Thr Lys Ser Ala Thr
1               5                   10                  15

<210> SEQ ID NO 69
<211> LENGTH: 15
<212> TYPE: PRT
<213> ORGANISM: Chlamydia psittaci

<400> SEQUENCE: 69

Asp Ala Gly Thr Glu Ala Ala Thr Asp Thr Lys Ser Ala Thr Leu
1               5                   10                  15

<210> SEQ ID NO 70
<211> LENGTH: 15
<212> TYPE: PRT
```

```
<213> ORGANISM: Chlamydia psittaci

<400> SEQUENCE: 70

Ala Ala Thr Asp Thr Lys Ser Ala Thr Leu Lys Tyr His Glu Trp
1               5                   10                  15

<210> SEQ ID NO 71
<211> LENGTH: 15
<212> TYPE: PRT
<213> ORGANISM: Chlamydia psittaci

<400> SEQUENCE: 71

Lys Ser Ala Thr Leu Lys Tyr His Glu Trp Gln Val Gly Leu Ala
1               5                   10                  15

<210> SEQ ID NO 72
<211> LENGTH: 15
<212> TYPE: PRT
<213> ORGANISM: Chlamydia psittaci

<400> SEQUENCE: 72

Ser Ala Thr Leu Lys Tyr His Glu Trp Gln Val Gly Leu Ala Leu
1               5                   10                  15

<210> SEQ ID NO 73
<211> LENGTH: 15
<212> TYPE: PRT
<213> ORGANISM: Chlamydia psittaci

<400> SEQUENCE: 73

Ala Thr Leu Lys Tyr His Glu Trp Gln Val Gly Leu Ala Leu Ser
1               5                   10                  15

<210> SEQ ID NO 74
<211> LENGTH: 15
<212> TYPE: PRT
<213> ORGANISM: Chlamydia psittaci

<400> SEQUENCE: 74

Leu Lys Tyr His Glu Trp Gln Val Gly Leu Ala Leu Ser Tyr Arg
1               5                   10                  15

<210> SEQ ID NO 75
<211> LENGTH: 15
<212> TYPE: PRT
<213> ORGANISM: Chlamydia psittaci

<400> SEQUENCE: 75

Lys Tyr His Glu Trp Gln Val Gly Leu Ala Leu Ser Tyr Arg Leu
1               5                   10                  15

<210> SEQ ID NO 76
<211> LENGTH: 15
<212> TYPE: PRT
<213> ORGANISM: Chlamydia psittaci

<400> SEQUENCE: 76

Tyr His Glu Trp Gln Val Gly Leu Ala Leu Ser Tyr Arg Leu Asn
1               5                   10                  15

<210> SEQ ID NO 77
<211> LENGTH: 15
<212> TYPE: PRT
<213> ORGANISM: Chlamydia psittaci
```

```
<400> SEQUENCE: 77

His Glu Trp Gln Val Gly Leu Ala Leu Ser Tyr Arg Leu Asn Met
1               5                   10                  15

<210> SEQ ID NO 78
<211> LENGTH: 15
<212> TYPE: PRT
<213> ORGANISM: Chlamydia psittaci

<400> SEQUENCE: 78

Tyr Arg Leu Asn Met Leu Val Pro Tyr Ile Gly Val Asn Trp Ser
1               5                   10                  15

<210> SEQ ID NO 79
<211> LENGTH: 15
<212> TYPE: PRT
<213> ORGANISM: Chlamydia psittaci

<400> SEQUENCE: 79

Arg Leu Asn Met Leu Val Pro Tyr Ile Gly Val Asn Trp Ser Arg
1               5                   10                  15

<210> SEQ ID NO 80
<211> LENGTH: 15
<212> TYPE: PRT
<213> ORGANISM: Chlamydia psittaci

<400> SEQUENCE: 80

Leu Asn Met Leu Val Pro Tyr Ile Gly Val Asn Trp Ser Arg Ala
1               5                   10                  15

<210> SEQ ID NO 81
<211> LENGTH: 15
<212> TYPE: PRT
<213> ORGANISM: Chlamydia psittaci

<400> SEQUENCE: 81

Asn Met Leu Val Pro Tyr Ile Gly Val Asn Trp Ser Arg Ala Thr
1               5                   10                  15

<210> SEQ ID NO 82
<211> LENGTH: 15
<212> TYPE: PRT
<213> ORGANISM: Chlamydia psittaci

<400> SEQUENCE: 82

Tyr Ile Gly Val Asn Trp Ser Arg Ala Thr Phe Asp Ala Asp Thr
1               5                   10                  15

<210> SEQ ID NO 83
<211> LENGTH: 15
<212> TYPE: PRT
<213> ORGANISM: Chlamydia psittaci

<400> SEQUENCE: 83

Asn Trp Ser Arg Ala Thr Phe Asp Ala Asp Thr Ile Arg Ile Ala
1               5                   10                  15

<210> SEQ ID NO 84
<211> LENGTH: 15
<212> TYPE: PRT
<213> ORGANISM: Chlamydia psittaci

<400> SEQUENCE: 84
```

```
Trp Ser Arg Ala Thr Phe Asp Ala Asp Thr Ile Arg Ile Ala Gln
1               5                   10                  15
```

<210> SEQ ID NO 85
<211> LENGTH: 15
<212> TYPE: PRT
<213> ORGANISM: Chlamydia psittaci

<400> SEQUENCE: 85

```
Ser Arg Ala Thr Phe Asp Ala Asp Thr Ile Arg Ile Ala Gln Pro
1               5                   10                  15
```

<210> SEQ ID NO 86
<211> LENGTH: 15
<212> TYPE: PRT
<213> ORGANISM: Chlamydia psittaci

<400> SEQUENCE: 86

```
Ala Thr Phe Asp Ala Asp Thr Ile Arg Ile Ala Gln Pro Lys Leu
1               5                   10                  15
```

<210> SEQ ID NO 87
<211> LENGTH: 15
<212> TYPE: PRT
<213> ORGANISM: Chlamydia psittaci

<400> SEQUENCE: 87

```
Ala Asp Thr Ile Arg Ile Ala Gln Pro Lys Leu Ala Thr Ala Val
1               5                   10                  15
```

<210> SEQ ID NO 88
<211> LENGTH: 15
<212> TYPE: PRT
<213> ORGANISM: Chlamydia psittaci

<400> SEQUENCE: 88

```
Ile Ala Gln Pro Lys Leu Ala Thr Ala Val Leu Asp Leu Thr Thr
1               5                   10                  15
```

<210> SEQ ID NO 89
<211> LENGTH: 15
<212> TYPE: PRT
<213> ORGANISM: Chlamydia psittaci

<400> SEQUENCE: 89

```
Ala Gln Pro Lys Leu Ala Thr Ala Val Leu Asp Leu Thr Thr Trp
1               5                   10                  15
```

<210> SEQ ID NO 90
<211> LENGTH: 15
<212> TYPE: PRT
<213> ORGANISM: Chlamydia psittaci

<400> SEQUENCE: 90

```
Thr Ala Val Leu Asp Leu Thr Thr Trp Asn Pro Thr Leu Leu Gly
1               5                   10                  15
```

<210> SEQ ID NO 91
<211> LENGTH: 15
<212> TYPE: PRT
<213> ORGANISM: Chlamydia psittaci

<400> SEQUENCE: 91

```
Lys Ala Thr Thr Val Asp Gly Thr Asn Thr Tyr Ser Asp Phe Leu
1               5                   10                  15
```

<210> SEQ ID NO 92
<211> LENGTH: 7
<212> TYPE: PRT
<213> ORGANISM: Chlamydia psittaci

<400> SEQUENCE: 92

Gly Thr Ala Ser Ala Thr Thr
1               5

<210> SEQ ID NO 93
<211> LENGTH: 6
<212> TYPE: PRT
<213> ORGANISM: Chlamydia psittaci

<400> SEQUENCE: 93

Gly Thr Asp Phe Asn Asn
1               5

<210> SEQ ID NO 94
<211> LENGTH: 8
<212> TYPE: PRT
<213> ORGANISM: Chlamydia psittaci

<400> SEQUENCE: 94

Asn Pro Thr Leu Leu Gly Lys Ala
1               5

<210> SEQ ID NO 95
<211> LENGTH: 8
<212> TYPE: PRT
<213> ORGANISM: Chlamydia psittaci

<400> SEQUENCE: 95

Thr Gly Thr Ala Ser Ala Thr Thr
1               5

<210> SEQ ID NO 96
<211> LENGTH: 8
<212> TYPE: PRT
<213> ORGANISM: Chlamydia psittaci

<400> SEQUENCE: 96

Lys Gly Thr Asp Phe Asn Asn Gln
1               5

<210> SEQ ID NO 97
<211> LENGTH: 22
<212> TYPE: PRT
<213> ORGANISM: Chlamydia psittaci

<400> SEQUENCE: 97

Glu Pro Ser Leu Leu Ile Asp Gly Thr Met Trp Glu Gly Ala Ser Gly
1               5                   10                  15

Asp Pro Cys Asp Pro Cys
            20

<210> SEQ ID NO 98
<211> LENGTH: 36
<212> TYPE: PRT
<213> ORGANISM: Chlamydia psittaci

<400> SEQUENCE: 98

Ala Gln Pro Lys Leu Ala Thr Ala Val Leu Asp Leu Thr Thr Trp Asn

```
1               5                  10                 15
Pro Thr Leu Leu Gly Lys Ala Thr Thr Val Asp Gly Thr Asn Thr Tyr
                20                 25                 30

Ser Asp Phe Leu
        35

<210> SEQ ID NO 99
<211> LENGTH: 45
<212> TYPE: PRT
<213> ORGANISM: Chlamydia psittaci

<400> SEQUENCE: 99

Ala Ala Thr Asp Thr Lys Ser Ala Thr Leu Lys Tyr His Glu Trp Gln
1               5                  10                 15

Val Gly Leu Ala Leu Ser Tyr Arg Leu Asn Met Leu Val Pro Tyr Ile
                20                 25                 30

Gly Val Asn Trp Ser Arg Ala Thr Phe Asp Ala Asp Thr
                35                 40                 45

<210> SEQ ID NO 100
<211> LENGTH: 234
<212> TYPE: DNA
<213> ORGANISM: Chlamydia psittaci

<400> SEQUENCE: 100
gctagcgaac caagtttatt aatcgatggc actatgtggg aaggtgcttc aggagatcct      60
tgcgatcctt gcacaggaac agcaagtgct actactaaag gaactgattt caataatcaa     120
gctcagccta aattagccac tgctgtttta gatttaacca cttggaaccc aacactttta     180
ggaaaggcca aactgtcga cggcaccaat acttactctg acttcttagg tacc            234

<210> SEQ ID NO 101
<211> LENGTH: 9
<212> TYPE: PRT
<213> ORGANISM: Chlamydia psittaci

<400> SEQUENCE: 101

Asp Gly Thr Met Trp Glu Gly Ala Ser
1               5

<210> SEQ ID NO 102
<211> LENGTH: 9
<212> TYPE: PRT
<213> ORGANISM: Chlamydia psittaci

<400> SEQUENCE: 102

Ala Ser Gly Asp Pro Cys Asp Pro Cys
1               5

<210> SEQ ID NO 103
<211> LENGTH: 13
<212> TYPE: PRT
<213> ORGANISM: Chlamydia psittaci

<400> SEQUENCE: 103

Ala Thr Asp Thr Lys Ser Ala Thr Leu Lys Tyr His Glu
1               5                  10

<210> SEQ ID NO 104
<211> LENGTH: 13
<212> TYPE: PRT
<213> ORGANISM: Chlamydia psittaci
```

<400> SEQUENCE: 104

Ser Ala Thr Leu Lys Tyr His Glu Trp Gln Val Gly Leu
1               5                   10

<210> SEQ ID NO 105
<211> LENGTH: 15
<212> TYPE: PRT
<213> ORGANISM: Chlamydia psittaci

<400> SEQUENCE: 105

Ser Ala Thr Leu Lys Tyr His Glu Trp Gln Val Gly Leu Ala Leu
1               5                   10                  15

<210> SEQ ID NO 106
<211> LENGTH: 13
<212> TYPE: PRT
<213> ORGANISM: Chlamydia psittaci

<400> SEQUENCE: 106

Thr Leu Lys Tyr His Glu Trp Gln Val Gly Leu Ala Leu
1               5                   10

<210> SEQ ID NO 107
<211> LENGTH: 13
<212> TYPE: PRT
<213> ORGANISM: Chlamydia psittaci

<400> SEQUENCE: 107

Lys Tyr His Glu Trp Gln Val Gly Leu Ala Leu Ser Tyr
1               5                   10

<210> SEQ ID NO 108
<211> LENGTH: 13
<212> TYPE: PRT
<213> ORGANISM: Chlamydia psittaci

<400> SEQUENCE: 108

Tyr His Glu Trp Gln Val Gly Leu Ala Leu Ser Tyr Arg
1               5                   10

<210> SEQ ID NO 109
<211> LENGTH: 13
<212> TYPE: PRT
<213> ORGANISM: Chlamydia psittaci

<400> SEQUENCE: 109

His Glu Trp Gln Val Gly Leu Ala Leu Ser Tyr Arg Leu
1               5                   10

<210> SEQ ID NO 110
<211> LENGTH: 12
<212> TYPE: PRT
<213> ORGANISM: Chlamydia psittaci

<400> SEQUENCE: 110

Gln Val Gly Leu Ala Leu Ser Tyr Arg Leu Asn Met
1               5                   10

<210> SEQ ID NO 111
<211> LENGTH: 13
<212> TYPE: PRT
<213> ORGANISM: Chlamydia psittaci

<400> SEQUENCE: 111

Arg Leu Asn Met Leu Val Pro Tyr Ile Gly Val Asn Trp
1               5                   10

<210> SEQ ID NO 112
<211> LENGTH: 14
<212> TYPE: PRT
<213> ORGANISM: Chlamydia psittaci

<400> SEQUENCE: 112

Arg Leu Asn Met Leu Val Pro Tyr Ile Gly Val Asn Trp Ser
1               5                   10

<210> SEQ ID NO 113
<211> LENGTH: 13
<212> TYPE: PRT
<213> ORGANISM: Chlamydia psittaci

<400> SEQUENCE: 113

Asn Met Leu Val Pro Tyr Ile Gly Val Asn Trp Ser Arg
1               5                   10

<210> SEQ ID NO 114
<211> LENGTH: 13
<212> TYPE: PRT
<213> ORGANISM: Chlamydia psittaci

<400> SEQUENCE: 114

Met Leu Val Pro Tyr Ile Gly Val Asn Trp Ser Arg Ala
1               5                   10

<210> SEQ ID NO 115
<211> LENGTH: 10
<212> TYPE: PRT
<213> ORGANISM: Chlamydia psittaci

<400> SEQUENCE: 115

Tyr Ile Gly Val Asn Trp Ser Arg Ala Thr
1               5                   10

<210> SEQ ID NO 116
<211> LENGTH: 9
<212> TYPE: PRT
<213> ORGANISM: Chlamydia psittaci

<400> SEQUENCE: 116

Thr Ala Val Leu Asp Leu Thr Thr Trp
1               5

<210> SEQ ID NO 117
<211> LENGTH: 13
<212> TYPE: PRT
<213> ORGANISM: Chlamydia psittaci

<400> SEQUENCE: 117

Thr Thr Val Asp Gly Thr Asn Thr Tyr Ser Asp Phe Leu
1               5                   10

<210> SEQ ID NO 118
<211> LENGTH: 66
<212> TYPE: DNA
<213> ORGANISM: Chlamydia psittaci

<400> SEQUENCE: 118
gaaccaagtt tattaatcga tggcactatg tgggaaggtg cttcaggaga tccttgcgat     60
ccttgc 66

<210> SEQ ID NO 119
<211> LENGTH: 24
<212> TYPE: DNA
<213> ORGANISM: Chlamydia psittaci

<400> SEQUENCE: 119
acaggaacag caagtgctac tact 24

<210> SEQ ID NO 120
<211> LENGTH: 24
<212> TYPE: DNA
<213> ORGANISM: Chlamydia psittaci

<400> SEQUENCE: 120
aaaggaactg atttcaataa tcaa 24

<210> SEQ ID NO 121
<211> LENGTH: 108
<212> TYPE: DNA
<213> ORGANISM: Chlamydia psittaci

<400> SEQUENCE: 121
gctcagccta aattagccac tgctgtttta gatttaacca cttggaaccc aacacttta 60 ggaaaggcca caactgtcga cggtaccaat acttactctg acttctta 108

<210> SEQ ID NO 122
<211> LENGTH: 135
<212> TYPE: DNA
<213> ORGANISM: Chlamydia psittaci

<400> SEQUENCE: 122
gctgctacag atactaagtc tgcaacactc aaatatcatg aatggcaagt tggtctagca 60
ctctcttaca gattgaacat gcttgttcct tacattggcg taaactggtc aagagcaact 120
tttgatgctg acact 135

<210> SEQ ID NO 123
<211> LENGTH: 1182
<212> TYPE: DNA
<213> ORGANISM: Chlamydia sp.

<400> SEQUENCE: 123
atgaaaaaac tcttgaaatc ggtattagta tttgccgctt tgagttctgc ttcctccttg 60
caagctctgc ctgtggggaa tcctgctgaa ccaagcctta tgatcgacgg aattctgtgg 120
gaaggtttcg gcggagatcc ttgcgatcct tgcgccactt ggtgtgacgc tatcagcatg 180
cgtgttggtt actacggaga ctttgttttc gaccgtgttt tgaaaactga tgtgaataaa 240
gaatttcaga tgggtgccaa gcctacaact gatacaggca atagtgcagc tccatccact 300
cttacagcaa gagagaatcc tgcttacggc cgacatatgc aggatgctga tgtgtttaca 360
aatgccgctt gcatggcatt gaatatttgg gatcgttttg atgtattctg tacattagga 420
gccaccagtg gatatcttaa aggaaactct gcttctttca atttagttgg attgtttgga 480
gataatgaaa atcaaaaaac ggtcaaagcg agtctgtac caaatatgag ctttgatcaa 540
tctgttgttg agttgtatac agatactact tttgcgtgga gcgtcggcgc tcgcgcagct 600
ttgtgggaat gtggatgtgc aactttagga gcttcattcc aatatgctca atctaaacct 660

| | |
|---|---|
| aaagtagaag aattaaacgt tctctgcaat gcagcagagt ttactattaa taaacctaaa | 720 |
| gggtatgtag gtaaggagtt tcctcttgat cttacagcag gaacagatgc tgcgacagga | 780 |
| actaaggatg cctctattga ttaccatgaa tggcaagcaa gtttagctct ctcttacaga | 840 |
| ctgaatatgt tcactcccta cattggagtt aaatggtctc gagcaagctt tgatgccgat | 900 |
| acgattcgta tagcccagcc aaaatcagct acagctattt ttgatactac cacgcttaac | 960 |
| ccaactattg ctggagctgg cgatgtgaaa actggcgcag agggtcagct cggagacaca | 1020 |
| atgcaaatcg tttccttgca attgaacaag atgaaatcta gaaaatcttg cggtattgca | 1080 |
| gtaggaacaa ctattgtgga tgcagacaaa tacgcagtta cagttgagac tcgcttgatc | 1140 |
| gatgagagag cagctcacgt aaatgcacaa ttccgcttct aa | 1182 |

<210> SEQ ID NO 124
<211> LENGTH: 1164
<212> TYPE: DNA
<213> ORGANISM: Chlamydia sp.

<400> SEQUENCE: 124

| | |
|---|---|
| atgaaaaaac tcttgaaatc ggtattagca tttgccgttt tgggttctgc ttcctccttg | 60 |
| catgctctgc ctgtggggaa tcctgctgaa ccaagcctta tgattgacgg gattctttgg | 120 |
| gaaggtttcg gtggagatcc ttgcgatcct tgcacaactt ggtgtgatgc catcagccta | 180 |
| cgtctcggct actatgggga cttcgttttt gatcgtgttt tgaaaacaga cgtgaacaaa | 240 |
| cagttcgaaa tgggagcagc tcctacagga gatgcagacc ttactacagc acctactcct | 300 |
| gcatcaagag agaatcccgc ttatggcaag catatgcaag atgcagaaat gttcactaat | 360 |
| gctgcgtaca tggctttaaa catttgggac cgtttcgatg tattttgtac attgggagca | 420 |
| actagcggat atcttaaagg taattctgcc gcctttaact tagttggtct gtttggaaga | 480 |
| gatgaaactg cagttgcagc tgacgacata cctaacgtca gcttgtctca agctgttgtc | 540 |
| gaactctaca gagacacagc tttcgcttgg agcgtcggtg ctagagcagc tttatgggag | 600 |
| tgcggatgtg caactttagg agcttccttc caatatgctc aatctaagcc aaaagtagag | 660 |
| gaattaaacg ttctctgtaa tgcggcagaa ttcactatta caagcctaa aggatacgtt | 720 |
| ggacaagagt ttcctcttaa cattaaagct ggaacagtta gcgctacaga tactaaagat | 780 |
| gcttccatcg attaccatga gtggcaagca agcttggctt tgtcttacag actgaatatg | 840 |
| ttcactcctt acattggagt taagtggtct agagcaagct ttgatgccga cactatccgc | 900 |
| attgcgcagc ctkagcttga gacctctatc ttaakaatga ccacttggaa cccaacgatc | 960 |
| tctggatctg gtatagacgt tgatacaaaa atcacggata cattacaaat tgtttccttg | 1020 |
| cagctcaaca agatgaaatc cagaaaatct tgcggtcttg caattggaac aacaattgta | 1080 |
| gatgctgata aatatgcagt tactgttgag acacgcttga tcgatgaaag agcagctcac | 1140 |
| gtaaatgctc agttccgttt ctaa | 1164 |

<210> SEQ ID NO 125
<211> LENGTH: 1170
<212> TYPE: DNA
<213> ORGANISM: Chlamydia sp.

<400> SEQUENCE: 125

| | |
|---|---|
| atgaaaaaac tcttaaagtc ggcgttatta tccgccgcat ttgctggttc tgttggctcc | 60 |
| ttacaagcct tgcctgtagg gaacccttct gatccaagct tattaattga tggtacaata | 120 |
| tgggaaggtg ctgcaggaga tccttgcgat ccttgcgcta cttggtgcga cgctattagc | 180 |

```
ttacgtgctg gattttacgg agactatgtt ttcgaccgta tcttaaaagt agatgcacct        240
aaaacatttt ctatgggagc caagcctact ggatccgctg ctgcaaacta tactactgcc        300
gtagatagac ctaacccggc ctacaataag catttacacg atgcagagtg gttcactaat        360
gcaggcttca ttgccttaaa catttgggat cgctttgatg ttttctgtac tttaggagct        420
tctaatggtt acattagagg aaactctaca gcgttcaatc tcgttggttt attcggagtt        480
aaaggtacta ctgtaaatgc aaatgaacta ccaaacgttt cttttaagtaa cggagttgtt        540 gaactttaca cagacacctc tttctcttgg agcgtaggcg ctcgtggagc cttatgggaa        600
tgcggttgtg caactttggg agctgaattc caatatgcac agtccaaacc taagttgaa         660 gaacttaatg tgatctgtaa cgtatcgcaa ttctctgtaa acaaacccaa gggctataaa        720
ggcgttgctt tccccttgcc aacagacgct ggcgtagcaa cagctactgg aacaaagtct        780
gcgaccatca attatcatga atggcaagta ggagcctctc tatcttacag actaaactct        840
ttagtgccat acattggagt acaatggtct cgagcaactt ttgatgctga taacatccgc        900
attgctcagc caaaactacc tacagctgtt ttaaacttaa ctgcatggaa cccttcttta        960
ctaggaaatg ccacagcatt gtctactact gattcgttct cagacttcat gcaaattgtt       1020
tcctgtcaga tcaacaagtt taaatctaga aaagcttgtg gagttactgt aggagctact       1080
ttagttgatg ctgataaatg gtcacttact gcagaagctc gtttaattaa cgagagagct       1140
gctcacgtat ctggtcagtt cagattctaa                                        1170

<210> SEQ ID NO 126
<211> LENGTH: 1179
<212> TYPE: DNA
<213> ORGANISM: Chlamydia sp.

<400> SEQUENCE: 126
atgaaaaaac tcttaaaatc ggcattatta tttgccgctg cgggttccgc tctctcctta         60
caagccttgc ctgtagggaa tccagctgaa ccaagtttat taatcgatgg cactatgtgg        120
gaaggtgctt caggagatcc ttgtgatcct tgtgctactt ggtgtgatgc tatcagcatc        180
cgtgcaggat tctacggaga ttatgttttc gatcgtatat taaaagttga tgttaataaa        240
accatcagcg gaatggctgc ggctccaaca gcagcttctg gaactgcaag caacaccact        300
gtcgctgccg acagatcaaa ttttgcctac ggcaaacatc ttcaagatgc cgaatggtgc        360
accaatgctg cttacttagc attaaatatt tgggatcgtt ttgatgtttt ctgcacgcta        420
ggagcgtcta atggttactt caaagcaagt tctgatgcat ttaaccttgt cggattgatt        480
ggtcttgcag gaactgattt cgccaatcag cgtccaaacg ttgaaatttc tcaaggcatt        540
gtagagctat acacagatac cgcatttttct tggagcgttg gtgctcgcgg agctttgtgg        600
gaatgtggtt gtgcaacttt gggagctgaa ttccaatatg ctcaatccaa tcctaaaatt        660
gaaatgctca atgtaacctc tagcccagca caattcatga tacacaagcc tagaggatac        720
aaagggactg cagcaaactt ccccttacct gtagcagctg gcacagcaac tgcaacagat        780
actaaatcag ctactgttaa gtaccatgaa tggcaagtag gattggctct ttcatacaga        840
ttgaacatgc ttgttccata cattgggta aattggtcaa gagctacttt cgatgctgac        900
actatccgca ttgctcaacc taaattggcc tcagcaatcc taaacttaac aacctggaac        960
ccaactcttt taggagtggc cacaacttta gacacctcca acaaatatgc tgacttcatg       1020
caaatcgttt ctatgcaaat caacaagatg aagtctagaa aagcttgtgg tattgctgtt       1080
```

```
ggagcaactt taatcgacgc tgataaatgg tccattactg gtgaagcacg cttaatcgac    1140
gaaagagctg ctcacattaa tgctcaattc agattctaa                            1179

<210> SEQ ID NO 127
<211> LENGTH: 1170
<212> TYPE: DNA
<213> ORGANISM: Chlamydia sp.

<400> SEQUENCE: 127
atgaaaaaac tcttgaaatc ggcattattg tttgccacta cgggttccgc tctctcctta      60
caagccttgc ctgtagggaa tccagctgaa ccaagtttat taattgatgg cactatgtgg     120
gaaggcgctt caggcgatcc ttgtgatcct tgctctactt ggtgtgatgc tatcagcatc     180
cgcgcagggt actacggaga ttatgttttc gatcgcatct aaaagttga tgttaataaa      240 actatcagca tggggacagc tccaactggt aatgcagctg ctgactttaa aaccgttgca     300
gacaggaata acatagccta cggcaaacat atgcaagatg cagaatggtc cacaaacgcg     360
gctttcttag cattaaacat tgggatcgt tttgatgtct tctgcacatt aggggcatct      420
aacggctatc tcaaagcaaa tgctgcagct ttcaatctag tcggcttact gggggtaaca     480
ggaacagatc ttcaaggcca atatccaaac gtagccatct ctcaaggcct tgtagagctt     540
tatactgaca caaccttctc ttggagcgtt ggtgcgcgtg gagctttatg ggaatgtggt     600
tgcgcaactt taggagcaga gttccaatat gcgcagtcta atcctaagat cgaaatgctt     660
aatgtaattt ctagcccaac acaatttgtg attcataagc ctagaggata taagggaca    720 gcggccaact tccctctgcc tttaaccgct ggaacagaga gcgctactga tactaaatca    780
gctacaatta agtatcatga atggcaaatt ggtttagctc tttcttatag attgaacatg     840
cttgttccat atattggagt aaactggtcc agagctacat tgatgctga ctctatccgc     900 attgctcagc ctaaattacc tacggccatt ttaaacctaa ctacatggaa ccctacttta     960
ttaggggagg ctactactat aaacactgga gcaaaatatg ctgaccagtt acaaattgct    1020
tcgcttcaaa tcaacaaaat gaagtctaga aaagcttgtg gtattgctgt tggtgcaacc    1080
ttaattgatg ctgacaaatg gtcgatcact ggtgaagctc gcttaatcaa cgaaagagct    1140
gctcacgtaa acgctcaatt cagattctaa                                    1170

<210> SEQ ID NO 128
<211> LENGTH: 1170
<212> TYPE: DNA
<213> ORGANISM: Chlamydia sp.

<400> SEQUENCE: 128
atgaaaaaac tcttgaaatc ggcattattg tttgccgcta cgggttccgc tctctcctta      60
caagccttgc ctgtagggaa cccagctgaa ccaagtttat taatcgatgg cactatgtgg     120
gaaggtgctt caggtgatcc ttgcgatcct tgctctactt ggtgtgatgc tatcagcatc     180
cgcgcaggat actacggaga ttatgttttc gatcgtgtat aaaagttga tgtgaataaa      240 actatcaccg gcatgggtgc agttcctaca ggaaccgcag cagctaatta caaaactcct     300
acggatagac ccaacatcgc ttacggcaaa cacttacaag cgccgaatg gttcaccaat      360 gcagctttcc tcgcattgaa tatctgggat cgctttgata ttttctgcac attaggcgct     420
tctaatgggt acttcaaagc tagttctgcg gcattcaacc tcgttggttt gattggtgtt     480
aaaggatcct cctagcagc tgatcagctt cccaatgtag gcatcactca aggaatcgtt     540 gaatttatata cagatacaac attctcttgg agtgtaggtg cacgcggagc tttatgggag    600
```

```
tgtggttgtg cgactttagg agcagagttc aatacgctc agtctaatcc taaaattgaa      660
atgttgaatg tagtctccag cccagcacaa tttgtggttc acaagcctag aggatacaag      720
ggaacagcat ttccttttacc tctaacagct ggtactgatc aggcaactga cactaagtcg     780
gctacaatta aataccacga atggcaagtt ggtttagcgc tctcttatcg attgaacatg      840
cttgttcctt acattagcgt aaactggtca cgagcaactt ttgatgctga cgctatccgc      900
atcgctcaac ctaaattagc tgctgctgtg ttaaacttga ccacatggaa cccaacccctt    960 ttaggagaag ctacagcttt agatactagc aacaaattcg ctgacttctt gcaaattgct     1020
tcgattcaga tcaacaaaat gaagtctaga aaagcttgtg gtgtagctgt tggtgcaacg     1080
ttaatcgacg ctgacaaatg gtcaatcact ggtgaagcac gcttaatcaa tgaaagagcc     1140
gctcacatga atgctcaatt cagattctaa                                      1170
```

<210> SEQ ID NO 129
<211> LENGTH: 1089
<212> TYPE: DNA
<213> ORGANISM: Chlamydia sp.

<400> SEQUENCE: 129

```
atgaaaaaac tcttgaaatc ggcattattg tttgccgcta cgggttccgc tctctcctta       60
caagccttgc ctgtagggaa cccagctgaa ccaagtttat taatcgatgg cactatgtgg      120
gaaggtgctt caggtgatcc ttgcgatcct tgctctactt ggtgtgatgc tatcagcatc      180
cgcgcaggat actacggaga ttatgttttc gatcgtgtat aaaagttgat cgtgaataaa      240
acttttaccg gcatgggtgc agttcctaca ggaaactcag cagctgattt taaaactcct      300
acagatagag cgaacatcgc ttatggcaag cacttgcaag acgccgaatg gtttaccaat      360
gcggcttttc tcgcattaaa tatttgggat cgctttgaca ttttctgcac attaggcgct      420
tctaatggct acttcaaagc tagttccgcg gcattcaatc tcgtcggttt gattggtatt      480
aaaggaaaca ccttaacaaa tgaccgactt cccaacgtag gcatcactca aggcgttgtt      540
gagttttaca cagatacaac attctcttgg agcgtaggtg cacgcggagc tttatgggag      600
tgcggttgtg caactttagg ggcagaattc aatacgctc aatctaatcc taaaattgaa       660
atgttgaatg taaccttcag cccagcacaa tttgtggttc acaaacctag aggctataaa      720
ggggcaacag cgaactttc tttacccgaa acaactggtt ctgatgctgc tacagatact       780
aaatctgcaa cactcaaata tcatgaatgg caagttggtc tagccctctc ttacagattg      840
aatatgcttg ttccatacat tggcgtaaac tggtcacgag caacttttga tgcggatact      900
atccgtatcg cgcaacctaa attggctgct gctgtgttaa acttgaccac atggaaccca     960
accctcttag gcaagctac aaatttagat actagcaaca aattcagcga cttcttacaa      1020
atcgcttcga ttcagatcaa caaaatgaag tctagaaaag cttgtggtgt agctgttggt    1080
gcaacgtta                                                            1089
```

<210> SEQ ID NO 130
<211> LENGTH: 1286
<212> TYPE: DNA
<213> ORGANISM: Chlamydia sp.

<400> SEQUENCE: 130

```
agaagagcaa attagaatag cgagcacaaa aagaaaagat actaagcata atctttagag       60
gtgagtatga aaaaactctt gaaatcggca ttattgtttg ccgctacggg ttccgctctc     120
```

```
tccttacaag ccttgcctgt agggaaccca gctgaaccaa gtttattaat cgatggcact        180
atgtgggaag gtgcttcagg agatccttgc gatccttgcg ctacttggtg tgacgccatt        240
agcatccgcg caggatacta cggagattat gttttcgatc gtgtattaaa agttgatgtg        300
aataaaactt ttagcggcat ggctgcaact cctacgcagg ctacaggtaa cgcaagtaat        360
actaatcagc cagaagcaaa tggcagaccg aacatcgctt acggaaggca tatgcaagat        420
gcagagtggt tttcaaatgc agccttccta gccttaaaca tttgggatcg cttcgacatt        480
ttctgcacct tagggcatc caatggatac ttcaaagcaa gttcggctgc attcaacttg         540
gttgggttaa tagggttttc agctgcaagc tcaatctcta ccgatcttcc aatgcaactt        600
cctaacgtag gcattaccca aggtgttgtg aatttttata cagacacatc attttcttgg        660
agcgtaggtg cacgtggagc tttatgggaa tgtggttgtg caactttagg agctgagttc        720
caatacgctc aatctaatcc taagatgaaa tgctcaacgt cacttcaagc ccagcacaat        780
ttgtgattca caaccaaga ggctataaag gagctagctc gaattttcct ttacctataa         840
cggctggaac aacagaagct acagacacca aatcagctac aattaaatac catgaatggc        900
aagtaggcct cgccctgtct tacagattga atatgcttgt tccatatatt ggcgtaaact        960
ggtcaagagc aacttttgat gctgatacta ccgcattgc tcaacctaaa ttaaaatcgg        1020
agattcttaa cattactaca tggaacccaa gccttatagg atcaaccact gctttgccca       1080
ataatagtgg taaggatgtt ctatctgatg tcttgcaaat tgcttcgatt cagatcaaca       1140
aaatgaagtc tagaaaagct tgtggtgtag ctgttggtgc aacgttaatc gacgctgaca       1200
aatggtcaat cactggtgaa gcacgcttaa tcaatgaaag agctgctcac atgaatgctc       1260
aattcagatt ctaaggattt agttta                                           1286
```

<210> SEQ ID NO 131
<211> LENGTH: 1445
<212> TYPE: DNA
<213> ORGANISM: Chlamydia sp.

<400> SEQUENCE: 131

```
atgaaaaaac tcttgaaatc ggcattattg tttgccgcta cgggttccgc tctctcctta         60
caagccttgc ctgtagggaa cccagctgaa ccaagtttat taatcgatgg cactatgtgg        120
gaaggtgctt caggagatcc ttgcgatcct tgcgctactt ggtgtgacgc cattagcatc        180
cgcgcaggat actacggaga ttatgttttc gatcgtgtat aaaagttga tgtgaataaa        240 acttttagcg gcatggctgc aactcctacg caggctacag gtaacgcaag taatactaat        300
cagccagaag caaatggcag accgaacatc gcttacggaa ggcatatgca agatgcagag        360
tggttttcaa atgcagcctt cctagcctta aacatttggg atcgcttcga cattttctgc        420
accttagggg catccaatgg atacttcaaa tcaagttcgg ctgcattcaa cttggttggg        480 ttaataggg tttcagctac caactcaacc tctaccgatc ttccaatgca acttcctaac         540
gtaggcatta cccaaggtgt tgtggaattt tatacagaca catcattttc ttggagcgta        600
ggtgcacgtg gagctttatg ggaatgtggt tgtgcaactt taggagctga gttccaatac        660
gctcaatcta atcctaagat tgaaatactc aacgtcactt caagcccagc acaatttgtg        720
attcacaaac caagaggcta taaggagct agctcgaatt ttcctttacc tataacggct        780
ggaacaacag aagctacaga caccaaatca gctacaatta ataccatga atggcaagta        840 ggcctcgccc tgtcttacag attgaatatg cttgttccat atattggcgt aaactggtca        900
agagcaactt tgatgctga tactatccgc attgctcaac taaattaaa atcggagatt        960
```

-continued

```
cttaacatta ctacatggaa cccaagcctt ctaggatcaa ccactgcttt gcccaataat    1020
agtggtaagg atgttctatc tgatgtcttg caaattgctt cgattcagat caacaaaatg    1080
aaatctagaa aatcttgtgg tgtagctgtt ggtgcaacgt taatcgacgc tgacaaatgg    1140
tcaatcactg gtgaagcacg cttaatcaat gaaagagctc tcacatgaa tgctcaattc     1200 agattctaag gatttagttt atactatcct aacttttgt cccgctatca gaacctggga     1260
gtctccgggt tctgatttt tttgctacca ccctttcag agtttcaaat ctcttttcta      1320
aaatccgttc gcatcagaat tcactgatta tctaaaattt tctagaagct agaaacctag    1380
agattacaat cttgcgtaaa aagcattatt aaattatctc tctattctta gcacgcgccc    1440
gtagt                                                                1445
```

<210> SEQ ID NO 132
<211> LENGTH: 1421
<212> TYPE: DNA
<213> ORGANISM: Chlamydia sp.

<400> SEQUENCE: 132

```
atgaaaaaac tcttgaaatc ggcattatta tttgccgcta cgggttccgc tctctcctta     60
caagccttgc ctgtagggaa cccagctgaa ccaagtttat taatcgatgg cactatgtgg    120
gaaggtgctt caggtgatcc ttgcgatcct tgctctactt ggtgtgatgc tatcagcatc    180
cgcgcaggat actacggaga ttatgttttc gatcgtgtat aaaagttga tgtgaataaa     240 actttcagcg gcattggcaa gaaacccaca ggatcctctc caaatgactt taaaaatgct    300
gaagatagac ccaacgtcgc ttatggcaga catttgcaag actccgaatg gtttacaaat    360
gcagcttctc tagcgttaaa tatctgggat cgttttgata tttctgcac attaggcgct    420 tctaatgggt acttcaaagc tagttctgcg gcattcaatc tcgttggttt gattggtgtt    480
aaaggaagct ccttaacaaa tgaccaactt cccaacgtag ccatcactca aggcgttgtt    540
gagttttaca cagatacaac gttctcttgg agcgtaggtg cacgtggagc tctatgggaa    600
tgtggttgcg caactttagg agctgaattc caatacgctc aatctaatcc taaaattgaa    660
atgttgaatg taatctccag cccagcacaa tttgtggttc acaagcctag aggatacaag    720
ggaacgtccg ccaactttcc tttacctgca aatgcaggca cagaggctgc tacggatact    780
aaatctgcaa cactcaaata tcatgaatgg caagttggtc tagcactctc ttacagattg    840
aacatgttag ttccttacat tggcgtaaac tggtcacgag caacttttga tgccgacact    900
atccgcatcg ctcaacctaa attggcctct gctgttatga acttgaccac atggaaccca    960
acccttttag gggaagccac aatgcttgat acttccaata aattcagtga cttcttacaa    1020
atcgcttcga ttcagatcaa caaaatgaag tctagaaaag cttgcggttt agctattggt    1080
gcaacgttaa tcgacgccga caaatggtca atcactggtg aagcacgctt aatcaatgaa    1140
agagctgctc acatgaatgc tcaattcaga ttctaaggat ttagtttata ctatcctaac    1200
tttttgtccc gctatcagaa cccaggagtc tctgggttct gatttttttt gctcacatcc    1260
ttttgtatag cttaatacct cttttttaaa atccattcgc acaagaattc actgattatc    1320
taaaattttc tagaagcttg aaacctagag attacaacct tgcgtaaaaa gcattattaa    1380
actaacatct ctattcttag cacgcgcccg tactcaatgg t                        1421
```

<210> SEQ ID NO 133
<211> LENGTH: 1430
<212> TYPE: DNA

<213> ORGANISM: Chlamydia sp.

<400> SEQUENCE: 133

```
aaactcttga atcggcatt attgtttgcc gctacgggtt ccgctctctc cttacaagcc      60
ttgcctgtag ggaacccagc tgaaccaagt ttattaatcg atggcactat gtgggaaggt     120
gcttcaggag atccttgcga tccttgcgct acttggtgtg acgccattag catccgcgca     180
ggatactacg gagattatgt tttcgatcgt gtattaaaag ttgatgtgaa taaaactttt     240
agcggcatgg ctaaatcacc tacagaggct acaggaacag caagtgctac tactactgct     300
gtagatagaa ccaatttagc ttatggcaaa catttgcaag atgccgaatg gtttaccaat     360
gcagctttcc tcgcattaaa tatctgggat cgctttgata ttttctgcac attaggcgct     420
tctaatgggt acttcaaagc tagttctgcg gcattcaacc tcgttggttt gattggtctt     480
aaaggaactg atttcaataa tcaacttcca acgtagcca tcacccaagg cgttgttgag      540
ttttacacag acacaacatt ctcttggagc gtgggtgcac gtggagctct atgggaatgt     600
ggttgtgcga ctttaggagc cgagttccaa tacgctcaat ctaatcctaa aattgaaatg     660
ctcaatgtaa cttcaagccc agcacaattt gtgattcaca aaccaagagg ctataaagga     720
actggctcga attttccttt acctatagac gcgggtacga aggctgctac agatactaag     780
tctgcaacac tcaaatatca tgaatggcaa gttggtctag cactctctta cagattgaac     840
atgcttgttc cttacattgg cgtaaactgg tcaagagcaa cttttgatgc tgacactatc     900
cgcattgctc agcctaaatt agccactgct gttttagatt taaccacttg gaacccaaca     960
cttttaggaa aggccacaac tgtcgacggt accaatactt actctgactt cttacaactt    1020
gcttcgattc aaatcaacaa aatgaagtct agaaaagctt gtggtgtagc tgttggtgca    1080
acgttaatcg acgctgacaa atggtcaatc actggtgacg cacgcttaat ccatgaagga    1140
gctgctcaca tgaatgctca attcagattc taaggattta gttgatactg tcctaacttt    1200
ttgtcccgct atcagaacct gggagtctcc gggttctgat ttttttttgct accacccttt    1260
tcagagtttc aaatctcttt tctaaaatcc attcgcatca gagttcagtg attatctaaa    1320
attttctaga agctagaaac ctagagatta caatcttgcg taaaaagcat tattaaatta    1380
acatctctat tcttagcacg cgcccgtagc tcaatggtag agctgtagcc             1430
```

<210> SEQ ID NO 134
<211> LENGTH: 1068
<212> TYPE: DNA
<213> ORGANISM: Chlamydia sp.

<400> SEQUENCE: 134

```
atgaaaaaac tcttgaaatc ggcattattg tttgccgcta cgggttccgc tctctcctta      60
caagccttgc ctgtagggaa cccagctgaa ccaagtttat aatcgatgg cactatgtgg     120
gaaggtgctt caggagatcc ttgcgatcct tgcgctactt ggtgtgacgc cattagcatc     180
cgcgcaggat actacggaga ttatgttttc gatcgtgtat taaagttga tgtgaataaa     240
acttttagcg gcatggctaa atcacctaca gaggctacag aacagcaag tgctactact     300
actgctgtag atagaaccaa tttagcttat ggcaaacatt tgcaagatgc cgaatggttt     360
accaatgcag ctttcctcgc attaaatatc tgggatcgct ttgatatttt ctgcacatta     420
ggcgcttcta atgggtactt caaagctagt tctgcggcat tcaacctcgt tggtttgatt     480
ggtcttaaag gaactgattt caataatcaa cttccaaacg tagccatcac ccaaggcgtt     540
gttgagtttt acacagacac aacattctct tggagcgtgg gtgcacgtgg agctctatgg     600
```

```
gaatgtggtt gtgcgacttt aggagccgag ttccaatacg ctcaatctaa tcctaaaatt    660
gaaatgctca atgtaacttc aagcccagca caatttgtga ttcacaaacc aagaggctat    720
aaaggaactg gctcgaattt tcctttacct atagacgcgg gtacagaggc tgctacagat    780
actaagtctg caacactcaa atatcatgaa tggcaagttg gtctagcact ctcttacaga    840
ttgaacatgc ttgttcctta cattggcgta aactggtcaa gagcaacttt tgatgctgac    900
actatccgca ttgctcagcc taaattagcc actgctgttt tagatttaac cacttggaac    960
ccaacacttt taggaaaggc cacaactgtc gacggtacca atacttactc tgacttctta   1020
caacttgctt cgattcaaat caacaaaatg aagtctagaa aagcttgt                1068

<210> SEQ ID NO 135
<211> LENGTH: 1393
<212> TYPE: DNA
<213> ORGANISM: Chlamydia sp.

<400> SEQUENCE: 135
caagccttgc ctgtagggaa cccagctgaa ccaagtttat taatcgatgg cactatgtgg     60
gaaggtgctt caggagatcc ttgcgatcct tgcgctactt ggtgtgacgc cattagcatc    120
cgcgcaggat actacggaga ttatgttttc gatcgtgtat aaaagttga tgtgaataaa     180 acttttagcg gcatggctgc aactcctacg caggctacag gtaacgcaag taatactaat    240
cagccagaag caaatggcag accgaacatc gcttacggaa ggcatatgca agatgcagag    300 tggtttttcaa atgcagcctt cctagcctta aacatttggg atcgcttcga cattttctgc    360
accttagggg catccaatgg atacttcaaa tcaagttcgg ctgcattcaa cttggttggg    420 ttaataggg tttcagctac cagctcaacc tctaccgagc ttccaatgca acttcctaac    480
gtaggcatta cccaaggtgt tgtggaattt tatacagaca catcatttc ttggagcgta    540 ggtgcacgtg gagctttatg ggaatgtggt tgtgcaactt taggagctga gttccaatac    600
gctcaatcta atcctaagat tgaagtgctc aacgtcactt caagcccagc acaatttgtg    660
attcacaaac caagaggcta taaaggagct agctcgaatt ttcctttacc tataacggct    720
ggaacaacag aagctacaga caccaaaatca gctacaatta ataccatga atggcaagta    780 ggcctcgccc tgtcttacag attgaatatg cttgttccat atattggcgt aaactggtca    840
agagcaactt tgatgctga tactatccgc attgctcaac ctaaattaaa atcggagatt    900
cttaacatta ctacatggaa cccaagcctt ctaggatcaa ccactacttt gcccaataat    960
ggtggtaagg atgttctatc tgatgtcttg caaattgctt cgattcagat caacaaaatg   1020
aagtctagaa aagcttgtgg tgtagctgtt ggtgcaacgt taatcgacgc tgacaaatgg   1080
tcaatcactg gtgaagcacg cttaatcaat gaaagagctg ctcacatgaa tgctcaattc   1140
agattctaag gatttagttt atactatcct aacttttgt cccgctatca gaacctggga    1200
gtctccgggt tctgattttt tttgctacca ccctttcag agtttcaaat ctcttttcta    1260
aaatccgttc gcatcagaat tcactgatta tctaaaattt tctagaagct agaaacctag    1320
agattacaat cttgcgtaaa aagcattatt aaattaacat ctctattctt agcacgcgcc   1380
cgtagctcaa tgg                                                       1393

<210> SEQ ID NO 136
<211> LENGTH: 1425
<212> TYPE: DNA
<213> ORGANISM: Chlamydia sp.
```

<400> SEQUENCE: 136

```
ctcttgaaat cggcattatt gtttgccgct acgggttccg ctctctcctt acaagccttg      60
cctgtaggga acccagctga accaagttta ttaatcgatg cactatgtg ggaaggtgct      120
tcaggagatc cttgcgatcc ttgcgctact tggtgtgacg ccattagcat ccgcgcagga     180
tactacggag attatgtttt cgatcgtgta ttaaaagttg atgtgaataa aactatcagc    240
ggtatgggtg cagctcctac aggaagcgca gcagccgatt acaaaactcc tacagataga    300
cccaacatcg cttatggcaa acacttgcaa gacgctgagt ggttcacgaa tgcagctttc    360
ctcgcattaa atatctggga tcgctttgat attttctgca cattaggtgc ttccaatggg    420
tacttcaaag ctagttctgc tgcattcaac ctcgttggtt tgattggtgt taaaggaacc    480
tccgtagcag ctgatcaact tccaaacgta ggcatcactc aaggtattgt tgagttttac    540
acagatacaa cattctcttg gagcgtaggt gcacgtggtg ctttatggga atgtggttgt    600
gcaactttag gagctgaatt ccagtatgct caatctaatc ctaaaattga aatgctgaat    660
gtaatctcca gcccaacaca atttgtagtt cacaagccta aggatacaa gggaacagga    720
tcgaactttc ctttacctct aacagctggt acagatggtg ctacagatac taaatctgca    780
acactcaaat atcatgaatg gcaagttggt ttagcgctct cttacagatt gaacatgctt    840
gttccttaca ttggcgtaaa ctggtcaaga gcaacttttg atgctgactc tatccgcatc    900
gctcaaccta aattagccgc tgctgttttg aacttgacca catggaaccc aactctttta    960
ggggaagcta cagctttaga tgctagcaac aaattctgcg acttcttaca aatcgcttcg    1020
attcagatca caaaatgaa atctagaaaa gcttgtggtg tagctgttgg tgcaacgtta    1080
atcgacgctg acaaatggtc aatcactggt gaagcacgct taatcaatga agagctgct    1140
cacatgaatg ctcaattcag attctaagga tttagtttat actatcctaa cttttgtgtcc    1200
cgctatcaga acctgggagt ctctgggttc tgatttttt tgctaccacc cttttgcaga    1260
gtttcaaatc tcttttctaa aatccgttcg cataagaatt cactgattat ctaaaattt    1320
ctagaagcta gaaacctaga gattacaatc ttgcgtaaaa agcattatta aattaacatc    1380
tctattctta gcacgcgccc gtagctcaat ggtagagctg tagcc                    1425
```

<210> SEQ ID NO 137
<211> LENGTH: 1089
<212> TYPE: DNA
<213> ORGANISM: Chlamydia sp.

<400> SEQUENCE: 137

```
ctcttgaaat cggcattatt gtttgccgct acgggttccg ctctctcctt acaagccttg      60
cctgtaggga acccagctga accaagttta ttaatcgatg cactatgtg ggaaggtgct      120
tcaggagatc cttgcgatcc ttgcgctact tggtgtgacg ccattagcat ccgcgcagga    180
tactacggag attatgtttt cgatcgtgta ttaaaagttg atgtgaataa aacttttagc    240
ggcatggctg caactcctac gcaggctaca ggtaacgcaa gtaatactaa tcagccagaa    300
gcaaatggca gaccgaacat cgcttacgga aggcatatgc aagatgcaga gtggttttca    360
aatgcagcct tcctagcctt aaacatttgg gatcgcttcg acttttctg cacccttaggg    420
gcatccaatg gatacttcaa atcaagttcg gctgcattca acttggttgg gttaataggg    480
ttttcagcta ccagctcaac ctctaccgag cttccaatgc aacttcctaa cgtaggcatt    540
acccaaggtg ttgtggaatt ttatacagac acatcatttt cttggagcgt aggtgcacgt    600
ggagctttat gggaatgtgg ttgtgcaact ttaggagctg agttccaata cgctcaatct    660
```

```
aatcctaaga ttgaagtgct caacgtcact tcaagcccag cacaatttgt gattcacaaa    720
ccaagaggct ataaaggagc tagctcgaat tttcctttac ctataacggc tggaacaaca    780
gaagctacag acaccaaatc agctacaatt aaataccatg aatggcaagt aggcctcgcc    840
ctgtcttaca gattgaatat gcttgttcca tatattggcg taaactggtc aagagcaact    900
tttgatgctg atactatccg cattgctcaa cctaaattaa atcggagat tcttaacatt     960 actacatgga acccaagcct tctaggatca accactgctt tgcccaataa tgctggtaag   1020
gatgttctat ctgatgtctt gcaaattgct tcgattcaga tcaacaaaat gaagtctaga   1080
aaagcttgt                                                           1089
```

<210> SEQ ID NO 138
<211> LENGTH: 1448
<212> TYPE: DNA
<213> ORGANISM: Chlamydia sp.

<400> SEQUENCE: 138

```
atgaaaaaac tcttgaaatc ggcattattg tttgccgcta cgggttccgc tctctcctta     60
caagccttgc ctgtagggaa cccagctgaa ccaagtttat taatcgatgg cactatgtgg    120
gaaggtgctt caggtgatcc ttgcgatcct tgctctactt ggtgtgatgc tatcagcatc    180
cgcgcaggat actacggaga ttatgttttc gatcgtgtat aaaagttga tgtgaataaa     240 acttttactg gaatggcagc aactcctaca gaggcttcag gtaacgcaac caatactggt    300
acgcccgaag caaacggcag agcgaatatc gcttacggaa ggcatatgca agatgcagag    360
tggttttcaa atgcagcttt tctagcctta aacatttggg atcgcttcga tattttctgc    420 acccttaggag catccaatgg atacttcaaa gcaagttctg ccgcattcaa cttggttggg   480
ttaatagggt tttcagcttc aagcgcagtt agtaccgatc ttccaaagca acttcctaac    540
gtagccatta cccaaggtgt tgtggaattt tatacagaca catcattttc ttggagcgta    600
ggtgcccgtg gagctttatg ggaatgtggt tgtgcaactt taggagctga gttccaatac    660
gctcaatcta atcctaagat tgaaatgctc aacgtaactt caagcccagc acaatttgtg    720
attcacaaac caagaggcta taaggaacc agctcgaatt ttcctttacc tataacggct    780
ggtactgatg atgcgacaga caccaaatca gctacaatta aataccatga atggcaagta    840
ggcctcgcac tgtcttacag attgaatatg cttgttccat atattggtgt aaactggtca    900
agagcaactt ttgatgctga tactatccgc attgctcaac taaattaaa atcagagatt    960 ctcaacatta ctacatggaa cccaagcctt ataggatcaa ccactgcttt gcccaataat   1020
agtggtaagg atgttctatc tgatgtcttg caaattgctt cgattcagat caacaaaatg   1080
aaatctagaa atcttgtgg tgtagctgtt ggtgcaacgt taatcgacgc tgataaatgg   1140
tccatcactg gtgaagcacg cttaatcaat gaaagagctg ctcacatgaa cgctcaattc   1200
agattctaag gatttagttt tatactatcc taacttttg tcccgctatc agaacctagg   1260
agcctctggg ttctgatttt ttttgccgca ttcttttttta gaagtttcaa atctcttttc   1320
taaaatccat ttgcacaagc attaacccac tatctaaaat tttctagaag cttaaaacct   1380
agagattaca accttgcgta aaaagcttta ttaaactaac atctctatct ttagcacgcg   1440
cccgtagt                                                           1448
```

<210> SEQ ID NO 139
<211> LENGTH: 1434
<212> TYPE: DNA

<213> ORGANISM: Chlamydia sp.

<400> SEQUENCE: 139

| | | | | | |
|---|---|---|---|---|---|
| aaatcggcat | tattgtttgc | cgctacgggt | tccgctctct | ccttacaagc | cttgcctgta | 60 |
| gggaacccag | ctgaaccaag | tttattaatc | gatggcacta | tgtgggaagg | tgcttcagga | 120 |
| gatccttgcg | atccttgcgc | tacttggtgt | gacgccatta | gcatccgcgc | aggatactac | 180 |
| ggagattatg | ttttcgatcg | tgtattaaaa | gttgatgtga | ataaaacttt | tagcggcatg | 240 |
| gctgcaattc | ctacggagtc | ttcaggaact | gtttcttcgg | ctaaacaagc | tgtagataga | 300 |
| gtcaatcttg | cctatgggaa | acatttacaa | gatgccgagt | ggtttacaaa | ttctgctttt | 360 |
| ctagcattaa | acatttggga | tcgctttgat | attttctgca | cattaggtgc | ttctaatggc | 420 |
| tacttcaagg | gaagttccgc | tgctttcaat | cttgttggct | tgttcggaat | tgctggaaat | 480 |
| agcgaaagta | atgctcttaa | tgaccaactt | ccaaacgtag | ctatcacaca | aggaatcgtt | 540 |
| gagttttaca | cagataccac | attctcttgg | agcgtgggtg | cacgcggagc | tttatgggag | 600 |
| tgtggctgcg | caactttagg | agcagaattc | caatacgcac | aatctaatcc | taaaattgaa | 660 |
| atgcttaatg | taacctctag | cccagcacaa | tttgtaattc | acaagcctag | gggatataaa | 720 |
| ggaacaacct | ctaattttcc | tttacctcta | acagctggca | cagacactgc | tacagatact | 780 |
| aagtcagcta | caattaaata | tcatgaatgg | caagttggtc | tagcgctctc | ttacagattg | 840 |
| aacatgctag | ttccttacat | tggcgtaaac | tggtcaagag | caacttttga | tgccgatact | 900 |
| atccgtatag | ctcagcctaa | attggctact | gctgttttag | acgcaaaaac | atggaaccca | 960 |
| accattactg | gggcatctgg | ttcagttgac | aacacaaaca | agtggtctga | caacttacaa | 1020 |
| attgcttcga | ttcagatcaa | caaaatgaag | tctagaaaag | cttgtggtgt | agctgttggt | 1080 |
| gcaacgttaa | tcgacgctga | caaatggtca | atcactggtg | aagcacgctt | aatcaatgaa | 1140 |
| agagctgctc | acatgaatgc | tcaattcaga | ttctaaggat | ttagtttata | ctatcctaac | 1200 |
| ttttgtccc | gctatcagaa | cctgggagtc | tctgggttct | gattttttt | gctaccaccc | 1260 |
| ttttgcagag | tttcaaatct | ctttttctaaa | atccgttcgc | ataagaattc | actgattatc | 1320 |
| taaaattttc | tagaagctag | aaacctagag | attacaatct | tgcgtaaaaa | gcattattaa | 1380 |
| attaacatct | ctattcttag | cacgcgcccg | tagctcaatg | gtagagctgt | agcc | 1434 |

<210> SEQ ID NO 140
<211> LENGTH: 1120
<212> TYPE: DNA
<213> ORGANISM: Chlamydia sp.

<400> SEQUENCE: 140

| | | | | | |
|---|---|---|---|---|---|
| atgaaaaaac | tcttgaaatc | ggcattattg | tttgccgcta | cgggttccgc | tctctcctta | 60 |
| caagccttgc | ctgtagggaa | cccagctgaa | ccaagtttat | taatcgatgg | cactatgtgg | 120 |
| gaaggtgctt | caggagatcc | ttgcgatcct | tgcgctactt | ggtgtgacgc | cattagcatc | 180 |
| cgcgcaggat | actacggaga | ttatgttttc | gatcgtgtat | taaaagttga | tgtgaataaa | 240 |
| acttttagcg | gcatggctgc | aactcctaca | ggctcaggac | gcaatatact | aatactcctg | 300 |
| agatagacaa | catcgcttac | ggcaaacatt | gcaagatgcg | agtggtttac | aaatgcagct | 360 |
| ttcctagcat | taaacatttg | ggatcgcttt | gatattttct | gcacattagg | gctctaatgg | 420 |
| tacttcaaag | caagttctgc | gcattcaacc | tgttggttga | ttggttaaag | gaaccttaac | 480 |
| aacaacttcc | aacgtaggca | tactcaaggg | ttgttgagtt | ttacacagac | acaacattct | 540 |
| cttggagcgt | aggtgcacgt | ggagctttat | gggaatgtgg | ttgtgcaact | ttaggagctg | 600 |

```
agttccaata cgctcaatct aatcctaaaa ttgaaatgct aatgtaacct cagcccagca      660
caatttgtga ttcacaaacc tagaggctat aaaggaacgc tcgaatttcc tttacctata      720
acgctggaca gagtgctaca gatactaaat cgctacaatt aaataccatg aatggcaagt      780
aggtctagcc ttcttacaga ttgaacatgc ttgttccata cattggcgta aactggtcaa      840
gagcaacttt tgatgctgat actatccgca ttgctcaacc taaattagcc gctattttaa      900
actacacatg gaacccaacc cttttaggaa gccaccttta tatgaaattc tctgactctt      960
gcaaattgct tcgattcaga tcaacaaaat gaagtctaga aaagcttgtg gtgtagctgt     1020
tggtgcaacg ttaatcgacg ctgacaaatg gtcaatcact ggtgaagcac gcttaatcaa     1080
tgaaagagct gctcacatga atgctcaatt cagattctaa                            1120
```

<210> SEQ ID NO 141
<211> LENGTH: 393
<212> TYPE: PRT
<213> ORGANISM: Chlamydia sp.

<400> SEQUENCE: 141

```
Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Asp Pro Cys
        35                  40                  45

Asp Pro Cys Ala Thr Trp Cys Asp Ala Ile Ser Met Arg Val Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Lys Pro Thr Thr Asp Thr Gly Asn Ser Ala
                85                  90                  95

Ala Pro Ser Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Thr Ser Gly
    130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
                165                 170                 175

Ser Phe Asp Gln Ser Val Val Glu Leu Tyr Thr Asp Thr Thr Phe Ala
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
```

```
                    275                 280                 285
Gly Val Lys Trp Ser Arg Ala Ser Phe Asp Ala Asp Thr Ile Arg Ile
            290                 295                 300
Ala Gln Pro Lys Ser Ala Thr Ala Ile Phe Asp Thr Thr Thr Leu Asn
305                 310                 315                 320
Pro Thr Ile Ala Gly Ala Gly Asp Val Lys Thr Gly Ala Glu Gly Gln
                325                 330                 335
Leu Gly Asp Thr Met Gln Ile Val Ser Leu Gln Leu Asn Lys Met Lys
            340                 345                 350
Ser Arg Lys Ser Cys Gly Ile Ala Val Gly Thr Thr Ile Val Asp Ala
            355                 360                 365
Asp Lys Tyr Ala Val Thr Val Glu Thr Arg Leu Ile Asp Glu Arg Ala
            370                 375                 380
Ala His Val Asn Ala Gln Phe Arg Phe
385                 390

<210> SEQ ID NO 142
<211> LENGTH: 387
<212> TYPE: PRT
<213> ORGANISM: Chlamydia sp.
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid

<400> SEQUENCE: 142

Met Lys Lys Leu Leu Lys Ser Val Leu Ala Phe Ala Val Leu Gly Ser
1               5                   10                  15
Ala Ser Ser Leu His Ala Leu Pro Val Gly Asn Pro Ala Glu Pro Ser
                20                  25                  30
Leu Met Ile Asp Gly Ile Leu Trp Glu Gly Phe Gly Gly Asp Pro Cys
            35                  40                  45
Asp Pro Cys Thr Thr Trp Cys Asp Ala Ile Ser Leu Arg Leu Gly Tyr
        50                  55                  60
Tyr Gly Asp Phe Val Phe Asp Arg Val Leu Lys Thr Asp Val Asn Lys
65                  70                  75                  80
Gln Phe Glu Met Gly Ala Ala Pro Thr Gly Asp Ala Asp Leu Thr Thr
                85                  90                  95
Ala Pro Thr Pro Ala Ser Arg Glu Asn Pro Ala Tyr Gly Lys His Met
            100                 105                 110
Gln Asp Ala Glu Met Phe Thr Asn Ala Ala Tyr Met Ala Leu Asn Ile
            115                 120                 125
Trp Asp Arg Phe Asp Val Phe Cys Thr Leu Gly Ala Thr Ser Gly Tyr
        130                 135                 140
Leu Lys Gly Asn Ser Ala Ala Phe Asn Leu Val Gly Leu Phe Gly Arg
145                 150                 155                 160
Asp Glu Thr Ala Val Ala Ala Asp Asp Ile Pro Asn Val Ser Leu Ser
                165                 170                 175
Gln Ala Val Val Glu Leu Tyr Thr Asp Thr Ala Phe Ala Trp Ser Val
            180                 185                 190
Gly Ala Arg Ala Ala Leu Trp Glu Cys Gly Cys Ala Thr Leu Gly Ala
            195                 200                 205
Ser Phe Gln Tyr Ala Gln Ser Lys Pro Lys Val Glu Glu Leu Asn Val
```

```
      210                 215                 220
Leu Cys Asn Ala Ala Glu Phe Thr Ile Asn Lys Pro Lys Gly Tyr Val
225                 230                 235                 240

Gly Gln Glu Phe Pro Leu Asn Ile Lys Ala Gly Thr Val Ser Ala Thr
                245                 250                 255

Asp Thr Lys Asp Ala Ser Ile Asp Tyr His Glu Trp Gln Ala Ser Leu
                260                 265                 270

Ala Leu Ser Tyr Arg Leu Asn Met Phe Thr Pro Tyr Ile Gly Val Lys
            275                 280                 285

Trp Ser Arg Ala Ser Phe Asp Ala Asp Thr Ile Arg Ile Ala Gln Pro
        290                 295                 300

Xaa Leu Glu Thr Ser Ile Leu Xaa Met Thr Thr Trp Asn Pro Thr Ile
305                 310                 315                 320

Ser Gly Ser Gly Ile Asp Val Asp Thr Lys Ile Thr Asp Thr Leu Gln
                325                 330                 335

Ile Val Ser Leu Gln Leu Asn Lys Met Lys Ser Arg Lys Ser Cys Gly
            340                 345                 350

Leu Ala Ile Gly Thr Thr Ile Val Asp Ala Asp Lys Tyr Ala Val Thr
        355                 360                 365

Val Glu Thr Arg Leu Ile Asp Glu Arg Ala Ala His Val Asn Ala Gln
    370                 375                 380

Phe Arg Phe
385

<210> SEQ ID NO 143
<211> LENGTH: 389
<212> TYPE: PRT
<213> ORGANISM: Chlamydia sp.

<400> SEQUENCE: 143

Met Lys Lys Leu Leu Lys Ser Ala Leu Leu Ser Ala Ala Phe Ala Gly
1               5                   10                  15

Ser Val Gly Ser Leu Gln Ala Leu Pro Val Gly Asn Pro Ser Asp Pro
            20                  25                  30

Ser Leu Leu Ile Asp Gly Thr Ile Trp Glu Gly Ala Ala Gly Asp Pro
        35                  40                  45

Cys Asp Pro Cys Ala Thr Trp Cys Asp Ala Ile Ser Leu Arg Ala Gly
    50                  55                  60

Phe Tyr Gly Asp Tyr Val Phe Asp Arg Ile Leu Lys Val Asp Ala Pro
65                  70                  75                  80

Lys Thr Phe Ser Met Gly Ala Lys Pro Thr Gly Ser Ala Ala Ala Asn
                85                  90                  95

Tyr Thr Thr Ala Val Asp Arg Pro Asn Pro Ala Tyr Asn Lys His Leu
            100                 105                 110

His Asp Ala Glu Trp Phe Thr Asn Ala Gly Phe Ile Ala Leu Asn Ile
        115                 120                 125

Trp Asp Arg Phe Asp Val Phe Cys Thr Leu Gly Ala Ser Asn Gly Tyr
    130                 135                 140

Ile Arg Gly Asn Ser Thr Ala Phe Asn Leu Val Gly Leu Phe Gly Val
145                 150                 155                 160

Lys Gly Thr Thr Val Asn Ala Asn Glu Leu Pro Asn Val Ser Leu Ser
                165                 170                 175

Asn Gly Val Val Glu Leu Tyr Thr Asp Thr Ser Phe Ser Trp Ser Val
            180                 185                 190
```

```
Gly Ala Arg Gly Ala Leu Trp Glu Cys Gly Cys Ala Thr Leu Gly Ala
            195                 200                 205

Glu Phe Gln Tyr Ala Gln Ser Lys Pro Lys Val Glu Glu Leu Asn Val
        210                 215                 220

Ile Cys Asn Val Ser Gln Phe Ser Val Asn Lys Pro Lys Gly Tyr Lys
225                 230                 235                 240

Gly Val Ala Phe Pro Leu Pro Thr Asp Ala Gly Val Ala Thr Ala Thr
                245                 250                 255

Gly Thr Lys Ser Ala Thr Ile Asn Tyr His Glu Trp Gln Val Gly Ala
            260                 265                 270

Ser Leu Ser Tyr Arg Leu Asn Ser Leu Val Pro Tyr Ile Gly Val Gln
        275                 280                 285

Trp Ser Arg Ala Thr Phe Asp Ala Asp Asn Ile Arg Ile Ala Gln Pro
    290                 295                 300

Lys Leu Pro Thr Ala Val Leu Asn Leu Thr Ala Trp Asn Pro Ser Leu
305                 310                 315                 320

Leu Gly Asn Ala Thr Ala Leu Ser Thr Thr Asp Ser Phe Ser Asp Phe
                325                 330                 335

Met Gln Ile Val Ser Cys Gln Ile Asn Lys Phe Lys Ser Arg Lys Ala
            340                 345                 350

Cys Gly Val Thr Val Gly Ala Thr Leu Val Asp Ala Asp Lys Trp Ser
        355                 360                 365

Leu Thr Ala Glu Ala Arg Leu Ile Asn Glu Arg Ala Ala His Val Ser
    370                 375                 380

Gly Gln Phe Arg Phe
385

<210> SEQ ID NO 144
<211> LENGTH: 392
<212> TYPE: PRT
<213> ORGANISM: Chlamydia sp.

<400> SEQUENCE: 144

Met Lys Lys Leu Leu Lys Ser Ala Leu Leu Phe Ala Ala Ala Gly Ser
1               5                   10                  15

Ala Leu Ser Leu Gln Ala Leu Pro Val Gly Asn Pro Ala Glu Pro Ser
            20                  25                  30

Leu Leu Ile Asp Gly Thr Met Trp Glu Gly Ala Ser Gly Asp Pro Cys
        35                  40                  45

Asp Pro Cys Ala Thr Trp Cys Asp Ala Ile Ser Ile Arg Ala Gly Phe
    50                  55                  60

Tyr Gly Asp Tyr Val Phe Asp Arg Ile Leu Lys Val Asp Val Asn Lys
65                  70                  75                  80

Thr Ile Ser Gly Met Ala Ala Pro Thr Ala Ser Gly Thr Ala
            85                  90                  95

Ser Asn Thr Thr Val Ala Ala Asp Arg Ser Asn Phe Ala Tyr Gly Lys
            100                 105                 110

His Leu Gln Asp Ala Glu Trp Cys Thr Asn Ala Ala Tyr Leu Ala Leu
        115                 120                 125

Asn Ile Trp Asp Arg Phe Asp Val Phe Cys Thr Leu Gly Ala Ser Asn
    130                 135                 140

Gly Tyr Phe Lys Ala Ser Ser Asp Ala Phe Asn Leu Val Gly Leu Ile
145                 150                 155                 160

Gly Leu Ala Gly Thr Asp Phe Ala Asn Gln Arg Pro Asn Val Glu Ile
                165                 170                 175
```

```
Ser Gln Gly Ile Val Glu Leu Tyr Thr Asp Thr Ala Phe Ser Trp Ser
            180                 185                 190

Val Gly Ala Arg Gly Ala Leu Trp Glu Cys Gly Cys Ala Thr Leu Gly
        195                 200                 205

Ala Glu Phe Gln Tyr Ala Gln Ser Asn Pro Lys Ile Glu Met Leu Asn
210                 215                 220

Val Thr Ser Ser Pro Ala Gln Phe Met Ile His Lys Pro Arg Gly Tyr
225                 230                 235                 240

Lys Gly Thr Ala Ala Asn Phe Pro Leu Pro Val Ala Ala Gly Thr Ala
                245                 250                 255

Thr Ala Thr Asp Thr Lys Ser Ala Thr Val Lys Tyr His Glu Trp Gln
                260                 265                 270

Val Gly Leu Ala Leu Ser Tyr Arg Leu Asn Met Leu Val Pro Tyr Ile
            275                 280                 285

Gly Val Asn Trp Ser Arg Ala Thr Phe Asp Ala Asp Thr Ile Arg Ile
        290                 295                 300

Ala Gln Pro Lys Leu Ala Ser Ala Ile Leu Asn Leu Thr Thr Trp Asn
305                 310                 315                 320

Pro Thr Leu Leu Gly Val Ala Thr Thr Leu Asp Thr Ser Asn Lys Tyr
                325                 330                 335

Ala Asp Phe Met Gln Ile Val Ser Met Gln Ile Asn Lys Met Lys Ser
                340                 345                 350

Arg Lys Ala Cys Gly Ile Ala Val Gly Ala Thr Leu Ile Asp Ala Asp
            355                 360                 365

Lys Trp Ser Ile Thr Gly Glu Ala Arg Leu Ile Asp Glu Arg Ala Ala
        370                 375                 380

His Ile Asn Ala Gln Phe Arg Phe
385                 390

<210> SEQ ID NO 145
<211> LENGTH: 389
<212> TYPE: PRT
<213> ORGANISM: Chlamydia sp.

<400> SEQUENCE: 145

Met Lys Lys Leu Leu Lys Ser Ala Leu Leu Phe Ala Thr Thr Gly Ser
1               5                   10                  15

Ala Leu Ser Leu Gln Ala Leu Pro Val Gly Asn Pro Ala Glu Pro Ser
                20                  25                  30

Leu Leu Ile Asp Gly Thr Met Trp Glu Gly Ala Ser Gly Asp Pro Cys
            35                  40                  45

Asp Pro Cys Ser Thr Trp Cys Asp Ala Ile Ser Ile Arg Ala Gly Tyr
        50                  55                  60

Tyr Gly Asp Tyr Val Phe Asp Arg Ile Leu Lys Val Asp Val Asn Lys
65                  70                  75                  80

Thr Ile Ser Met Gly Thr Ala Pro Thr Gly Asn Ala Ala Ala Asp Phe
                85                  90                  95

Lys Thr Val Ala Asp Arg Asn Asn Ile Ala Tyr Gly Lys His Met Gln
                100                 105                 110

Asp Ala Glu Trp Ser Thr Asn Ala Ala Phe Leu Ala Leu Asn Ile Trp
            115                 120                 125

Asp Arg Phe Asp Val Phe Cys Thr Leu Gly Ala Ser Asn Gly Tyr Leu
        130                 135                 140

Lys Ala Asn Ala Ala Ala Phe Asn Leu Val Gly Leu Leu Gly Val Thr
```

```
            145                 150                 155                 160
        Gly Thr Asp Leu Gln Gly Gln Tyr Pro Asn Val Ala Ile Ser Gln Gly
                        165                 170                 175

Leu Val Glu Leu Tyr Thr Asp Thr Thr Phe Ser Trp Ser Val Gly Ala
                        180                 185                 190

Arg Gly Ala Leu Trp Glu Cys Gly Cys Ala Thr Leu Gly Ala Glu Phe
                        195                 200                 205

Gln Tyr Ala Gln Ser Asn Pro Lys Ile Glu Met Leu Asn Val Thr Ser
                        210                 215                 220

Ser Pro Ala Gln Phe Met Ile His Lys Pro Arg Gly Tyr Lys Gly Thr
        225                 230                 235                 240

Ala Ala Asn Phe Pro Leu Pro Val Ala Gly Thr Ala Thr Ala Thr
                        245                 250                 255

Asp Thr Lys Ser Ala Thr Val Lys Tyr His Glu Trp Gln Ile Gly Leu
                        260                 265                 270

Ala Leu Ser Tyr Arg Leu Asn Met Leu Val Pro Tyr Ile Gly Val Asn
                        275                 280                 285

Trp Ser Arg Ala Thr Phe Asp Ala Asp Ser Ile Arg Ile Ala Gln Pro
                        290                 295                 300

Lys Leu Pro Thr Ala Ile Leu Asn Leu Thr Thr Trp Asn Pro Thr Leu
        305                 310                 315                 320

Leu Gly Glu Ala Thr Thr Ile Asn Thr Gly Ala Lys Tyr Ala Asp Gln
                        325                 330                 335

Leu Gln Ile Ala Ser Leu Gln Ile Asn Lys Met Lys Ser Arg Lys Ala
                        340                 345                 350

Cys Gly Ile Ala Val Gly Ala Thr Leu Ile Asp Ala Asp Lys Trp Ser
                        355                 360                 365

Ile Thr Gly Glu Ala Arg Leu Ile Asn Glu Arg Ala Ala His Val Asn
                        370                 375                 380

Ala Gln Phe Arg Phe
        385

<210> SEQ ID NO 146
<211> LENGTH: 389
<212> TYPE: PRT
<213> ORGANISM: Chlamydia sp.

<400> SEQUENCE: 146

Met Lys Lys Leu Leu Lys Ser Ala Leu Leu Phe Ala Ala Thr Gly Ser
        1               5                   10                  15

Ala Leu Ser Leu Gln Ala Leu Pro Val Gly Asn Pro Ala Glu Pro Ser
                        20                  25                  30

Leu Leu Ile Asp Gly Thr Met Trp Glu Gly Ala Ser Gly Asp Pro Cys
                        35                  40                  45

Asp Pro Cys Ser Thr Trp Cys Asp Ala Ile Ser Ile Arg Ala Gly Tyr
                        50                  55                  60

Tyr Gly Asp Tyr Val Phe Asp Arg Val Leu Lys Val Asp Val Asn Lys
        65                  70                  75                  80

Thr Ile Thr Gly Met Gly Ala Val Pro Thr Gly Thr Ala Ala Asn
                        85                  90                  95

Tyr Lys Thr Pro Thr Asp Arg Pro Asn Ile Ala Tyr Gly Lys His Leu
                        100                 105                 110

Gln Asp Ala Glu Trp Phe Thr Asn Ala Ala Phe Leu Ala Leu Asn Ile
                        115                 120                 125
```

```
Trp Asp Arg Phe Asp Ile Phe Cys Thr Leu Gly Ala Ser Asn Gly Tyr
130                 135                 140

Phe Lys Ala Ser Ser Ala Ala Phe Asn Leu Val Gly Leu Ile Gly Val
145                 150                 155                 160

Lys Gly Ser Ser Ile Ala Ala Asp Gln Leu Pro Asn Val Gly Ile Thr
                165                 170                 175

Gln Gly Ile Val Glu Phe Tyr Thr Asp Thr Thr Phe Ser Trp Ser Val
                180                 185                 190

Gly Ala Arg Gly Ala Leu Trp Glu Cys Gly Cys Ala Thr Leu Gly Ala
                195                 200                 205

Glu Phe Gln Tyr Ala Gln Ser Asn Pro Lys Ile Glu Met Leu Asn Val
210                 215                 220

Val Ser Ser Pro Ala Gln Phe Val Val His Lys Pro Arg Gly Tyr Lys
225                 230                 235                 240

Gly Thr Ala Phe Pro Leu Pro Leu Thr Ala Gly Thr Asp Gln Ala Thr
                245                 250                 255

Asp Thr Lys Ser Ala Thr Ile Lys Tyr His Glu Trp Gln Val Gly Leu
                260                 265                 270

Ala Leu Ser Tyr Arg Leu Asn Met Leu Val Pro Tyr Ile Ser Val Asn
            275                 280                 285

Trp Ser Arg Ala Thr Phe Asp Ala Asp Ala Ile Arg Ile Ala Gln Pro
290                 295                 300

Lys Leu Ala Ala Ala Val Leu Asn Leu Thr Thr Trp Asn Pro Thr Leu
305                 310                 315                 320

Leu Gly Glu Ala Thr Ala Leu Asp Thr Ser Asn Lys Phe Ala Asp Phe
                325                 330                 335

Leu Gln Ile Ala Ser Ile Gln Ile Asn Lys Met Lys Ser Arg Lys Ala
                340                 345                 350

Cys Gly Val Ala Val Gly Ala Thr Leu Ile Asp Ala Asp Lys Trp Ser
            355                 360                 365

Ile Thr Gly Glu Ala Arg Leu Ile Asn Glu Arg Ala Ala His Met Asn
        370                 375                 380

Ala Gln Phe Arg Phe
385

<210> SEQ ID NO 147
<211> LENGTH: 363
<212> TYPE: PRT
<213> ORGANISM: Chlamydia sp.

<400> SEQUENCE: 147

Met Lys Lys Leu Leu Lys Ser Ala Leu Leu Phe Ala Ala Thr Gly Ser
1               5                   10                  15

Ala Leu Ser Leu Gln Ala Leu Pro Val Gly Asn Pro Ala Glu Pro Ser
                20                  25                  30

Leu Leu Ile Asp Gly Thr Met Trp Glu Gly Ala Ser Gly Asp Pro Cys
            35                  40                  45

Asp Pro Cys Ser Thr Trp Cys Asp Ala Ile Ser Ile Arg Ala Gly Tyr
        50                  55                  60

Tyr Gly Asp Tyr Val Phe Asp Arg Val Leu Lys Val Asp Val Asn Lys
65                  70                  75                  80

Thr Phe Thr Gly Met Gly Ala Val Pro Thr Gly Asn Ser Ala Ala Asp
                85                  90                  95

Phe Lys Thr Pro Thr Asp Arg Ala Asn Ile Ala Tyr Gly Lys His Leu
                100                 105                 110
```

```
Gln Asp Ala Glu Trp Phe Thr Asn Ala Ala Phe Leu Ala Leu Asn Ile
        115                 120                 125
Trp Asp Arg Phe Asp Ile Phe Cys Thr Leu Gly Ala Ser Asn Gly Tyr
    130                 135                 140
Phe Lys Ala Ser Ser Ala Ala Phe Asn Leu Val Gly Leu Ile Gly Ile
145                 150                 155                 160
Lys Gly Asn Thr Leu Thr Asn Asp Arg Leu Pro Asn Val Gly Ile Thr
                165                 170                 175
Gln Gly Val Val Glu Phe Tyr Thr Asp Thr Thr Phe Ser Trp Ser Val
            180                 185                 190
Gly Ala Arg Gly Ala Leu Trp Glu Cys Gly Cys Ala Thr Leu Gly Ala
        195                 200                 205
Glu Phe Gln Tyr Ala Gln Ser Asn Pro Lys Ile Glu Met Leu Asn Val
    210                 215                 220
Thr Phe Ser Pro Ala Gln Phe Val Val His Lys Pro Arg Gly Tyr Lys
225                 230                 235                 240
Gly Ala Thr Ala Asn Phe Ser Leu Pro Glu Thr Thr Gly Ser Asp Ala
                245                 250                 255
Ala Thr Asp Thr Lys Ser Ala Thr Leu Lys Tyr His Glu Trp Gln Val
            260                 265                 270
Gly Leu Ala Leu Ser Tyr Arg Leu Asn Met Leu Val Pro Tyr Ile Gly
        275                 280                 285
Val Asn Trp Ser Arg Ala Thr Phe Asp Ala Asp Thr Ile Arg Ile Ala
    290                 295                 300
Gln Pro Lys Leu Ala Ala Val Leu Asn Leu Thr Thr Trp Asn Pro
305                 310                 315                 320
Thr Leu Leu Gly Gln Ala Thr Asn Leu Asp Thr Ser Asn Lys Phe Ser
                325                 330                 335
Asp Phe Leu Gln Ile Ala Ser Ile Gln Ile Asn Lys Met Lys Ser Arg
            340                 345                 350
Lys Ala Cys Gly Val Ala Val Gly Ala Thr Leu
        355                 360

<210> SEQ ID NO 148
<211> LENGTH: 425
<212> TYPE: PRT
<213> ORGANISM: Chlamydia sp.

<400> SEQUENCE: 148

Arg Arg Ala Asn Asn Ser Glu His Lys Lys Arg Tyr Ala Ser Leu
1               5                   10                  15
Glu Val Ser Met Lys Lys Leu Leu Lys Ser Ala Leu Leu Phe Ala Ala
            20                  25                  30
Thr Gly Ser Ala Leu Ser Leu Gln Ala Leu Pro Val Gly Asn Pro Ala
        35                  40                  45
Glu Pro Ser Leu Leu Ile Asp Gly Thr Met Trp Glu Gly Ala Ser Gly
    50                  55                  60
Asp Pro Cys Asp Pro Cys Ala Thr Trp Cys Asp Ala Ile Ser Ile Arg
65                  70                  75                  80
Ala Gly Tyr Tyr Gly Asp Tyr Val Phe Asp Arg Val Leu Lys Val Asp
                85                  90                  95
Val Asn Lys Thr Phe Ser Gly Met Ala Ala Thr Pro Thr Gln Ala Thr
            100                 105                 110
Gly Asn Ala Ser Asn Thr Asn Gln Pro Glu Ala Asn Gly Arg Pro Asn
```

```
            115                 120                 125
Ile Ala Tyr Gly Arg His Met Gln Asp Ala Glu Trp Phe Ser Asn Ala
130                 135                 140

Ala Phe Leu Ala Leu Asn Ile Trp Asp Arg Phe Asp Ile Phe Cys Thr
145                 150                 155                 160

Leu Gly Ala Ser Asn Gly Tyr Phe Lys Ala Ser Ser Ala Ala Phe Asn
                165                 170                 175

Leu Val Gly Leu Ile Gly Phe Ser Ala Ala Ser Ser Ile Ser Thr Asp
            180                 185                 190

Leu Pro Met Gln Leu Pro Asn Val Gly Ile Thr Gln Gly Val Val Glu
        195                 200                 205

Phe Tyr Thr Asp Thr Ser Phe Ser Trp Ser Val Gly Ala Arg Gly Ala
    210                 215                 220

Leu Trp Glu Cys Gly Cys Ala Thr Leu Gly Ala Glu Phe Gln Tyr Ala
225                 230                 235                 240

Gln Ser Asn Pro Lys Ile Glu Met Leu Asn Val Thr Ser Ser Pro Ala
                245                 250                 255

Gln Phe Val Ile His Lys Pro Arg Gly Tyr Lys Gly Ala Ser Ser Asn
            260                 265                 270

Phe Pro Leu Pro Ile Thr Ala Gly Thr Thr Glu Ala Thr Asp Thr Lys
        275                 280                 285

Ser Ala Thr Ile Lys Tyr His Glu Trp Gln Val Gly Leu Ala Leu Ser
    290                 295                 300

Tyr Arg Leu Asn Met Leu Val Pro Tyr Ile Gly Val Asn Trp Ser Arg
305                 310                 315                 320

Ala Thr Phe Asp Ala Asp Thr Ile Arg Ile Ala Gln Pro Lys Leu Lys
                325                 330                 335

Ser Glu Ile Leu Asn Ile Thr Thr Trp Asn Pro Ser Leu Ile Gly Ser
            340                 345                 350

Thr Thr Ala Leu Pro Asn Asn Ser Gly Lys Asp Val Leu Ser Asp Val
        355                 360                 365

Leu Gln Ile Ala Ser Ile Gln Ile Asn Lys Met Lys Ser Arg Lys Ala
    370                 375                 380

Cys Gly Val Ala Val Gly Ala Thr Leu Ile Asp Ala Asp Lys Trp Ser
385                 390                 395                 400

Ile Thr Gly Glu Ala Arg Leu Ile Asn Glu Arg Ala Ala His Met Asn
                405                 410                 415

Ala Gln Phe Arg Phe Gly Phe Ser Leu
            420                 425

<210> SEQ ID NO 149
<211> LENGTH: 475
<212> TYPE: PRT
<213> ORGANISM: Chlamydia sp.

<400> SEQUENCE: 149

Met Lys Lys Leu Leu Lys Ser Ala Leu Leu Phe Ala Ala Thr Gly Ser
1               5                   10                  15

Ala Leu Ser Leu Gln Ala Leu Pro Val Gly Asn Pro Ala Glu Pro Ser
            20                  25                  30

Leu Leu Ile Asp Gly Thr Met Trp Glu Gly Ala Ser Gly Asp Pro Cys
        35                  40                  45

Asp Pro Cys Ala Thr Trp Cys Asp Ala Ile Ser Ile Arg Ala Gly Tyr
    50                  55                  60
```

```
Tyr Gly Asp Tyr Val Phe Asp Arg Val Leu Lys Val Asp Val Asn Lys
 65                  70                  75                  80

Thr Phe Ser Gly Met Ala Ala Thr Pro Thr Gln Ala Thr Gly Asn Ala
                 85                  90                  95

Ser Asn Thr Asn Gln Pro Glu Ala Asn Gly Arg Pro Asn Ile Ala Tyr
            100                 105                 110

Gly Arg His Met Gln Asp Ala Glu Trp Phe Ser Asn Ala Ala Phe Leu
        115                 120                 125

Ala Leu Asn Ile Trp Asp Arg Phe Asp Ile Phe Cys Thr Leu Gly Ala
    130                 135                 140

Ser Asn Gly Tyr Phe Lys Ser Ser Ala Ala Phe Asn Leu Val Gly
145                 150                 155                 160

Leu Ile Gly Phe Ser Ala Thr Asn Ser Thr Ser Thr Asp Leu Pro Met
            165                 170                 175

Gln Leu Pro Asn Val Gly Ile Thr Gln Gly Val Val Glu Phe Tyr Thr
            180                 185                 190

Asp Thr Ser Phe Ser Trp Ser Val Gly Ala Arg Gly Ala Leu Trp Glu
        195                 200                 205

Cys Gly Cys Ala Thr Leu Gly Ala Glu Phe Gln Tyr Ala Gln Ser Asn
    210                 215                 220

Pro Lys Ile Glu Ile Leu Asn Val Thr Ser Ser Pro Ala Gln Phe Val
225                 230                 235                 240

Ile His Lys Pro Arg Gly Tyr Lys Gly Ala Ser Ser Asn Phe Pro Leu
            245                 250                 255

Pro Ile Thr Ala Gly Thr Thr Glu Ala Thr Asp Thr Lys Ser Ala Thr
            260                 265                 270

Ile Lys Tyr His Glu Trp Gln Val Gly Leu Ala Leu Ser Tyr Arg Leu
        275                 280                 285

Asn Met Leu Val Pro Tyr Ile Gly Val Asn Trp Ser Arg Ala Thr Phe
    290                 295                 300

Asp Ala Asp Thr Ile Arg Ile Ala Gln Pro Lys Leu Lys Ser Glu Ile
305                 310                 315                 320

Leu Asn Ile Thr Thr Trp Asn Pro Ser Leu Leu Gly Ser Thr Thr Ala
            325                 330                 335

Leu Pro Asn Asn Ser Gly Lys Asp Val Leu Ser Asp Val Leu Gln Ile
            340                 345                 350

Ala Ser Ile Gln Ile Asn Lys Met Lys Ser Arg Lys Ser Cys Gly Val
        355                 360                 365

Ala Val Gly Ala Thr Leu Ile Asp Ala Asp Lys Trp Ser Ile Thr Gly
    370                 375                 380

Glu Ala Arg Leu Ile Asn Glu Arg Ala Ala His Met Asn Ala Gln Phe
385                 390                 395                 400

Arg Phe Gly Phe Ser Leu Tyr Tyr Pro Asn Phe Leu Ser Arg Tyr Gln
            405                 410                 415

Asn Leu Gly Val Ser Gly Phe Phe Phe Leu Leu Pro Pro Phe Ser Glu
            420                 425                 430

Phe Gln Ile Ser Phe Leu Lys Ser Val Arg Ile Arg Ile His Leu Ser
        435                 440                 445

Lys Ile Phe Lys Leu Glu Thr Arg Leu Gln Ser Cys Val Lys Ser Ile
    450                 455                 460

Ile Lys Leu Ser Leu Tyr Ser His Ala Pro Val
465                 470                 475
```

```
<210> SEQ ID NO 150
<211> LENGTH: 467
<212> TYPE: PRT
<213> ORGANISM: Chlamydia sp.

<400> SEQUENCE: 150

Met Lys Lys Leu Leu Lys Ser Ala Leu Leu Phe Ala Ala Thr Gly Ser
1               5                   10                  15

Ala Leu Ser Leu Gln Ala Leu Pro Val Gly Asn Pro Ala Glu Pro Ser
            20                  25                  30

Leu Leu Ile Asp Gly Thr Met Trp Glu Gly Ala Ser Gly Asp Pro Cys
        35                  40                  45

Asp Pro Cys Ser Thr Trp Cys Asp Ala Ile Ser Ile Arg Ala Gly Tyr
    50                  55                  60

Tyr Gly Asp Tyr Val Phe Asp Arg Val Leu Lys Val Asp Val Asn Lys
65                  70                  75                  80

Thr Phe Ser Gly Ile Gly Lys Lys Pro Thr Gly Ser Ser Pro Asn Asp
                85                  90                  95

Phe Lys Asn Ala Glu Asp Arg Pro Asn Val Ala Tyr Gly Arg His Leu
            100                 105                 110

Gln Asp Ser Glu Trp Phe Thr Asn Ala Ala Phe Leu Ala Leu Asn Ile
        115                 120                 125

Trp Asp Arg Phe Asp Ile Phe Cys Thr Leu Gly Ala Ser Asn Gly Tyr
    130                 135                 140

Phe Lys Ala Ser Ser Ala Ala Phe Asn Leu Val Gly Leu Ile Gly Val
145                 150                 155                 160

Lys Gly Ser Ser Leu Thr Asn Asp Gln Leu Pro Asn Val Ala Ile Thr
                165                 170                 175

Gln Gly Val Val Glu Phe Tyr Thr Asp Thr Thr Phe Ser Trp Ser Val
            180                 185                 190

Gly Ala Arg Gly Ala Leu Trp Glu Cys Gly Cys Ala Thr Leu Gly Ala
        195                 200                 205

Glu Phe Gln Tyr Ala Gln Ser Asn Pro Lys Ile Glu Met Leu Asn Val
    210                 215                 220

Ile Ser Ser Pro Ala Gln Phe Val Val His Lys Pro Arg Gly Tyr Lys
225                 230                 235                 240

Gly Thr Ser Ala Asn Phe Pro Leu Pro Ala Asn Ala Gly Thr Glu Ala
                245                 250                 255

Ala Thr Asp Thr Lys Ser Ala Thr Leu Lys Tyr His Glu Trp Gln Val
            260                 265                 270

Gly Leu Ala Leu Ser Tyr Arg Leu Asn Met Leu Val Pro Tyr Ile Gly
        275                 280                 285

Val Asn Trp Ser Arg Ala Thr Phe Asp Ala Asp Thr Ile Arg Ile Ala
    290                 295                 300

Gln Pro Lys Leu Ala Ser Ala Val Met Asn Leu Thr Thr Trp Asn Pro
305                 310                 315                 320

Thr Leu Leu Gly Glu Ala Thr Met Leu Asp Thr Ser Asn Lys Phe Ser
                325                 330                 335

Asp Phe Leu Gln Ile Ala Ser Ile Gln Ile Asn Lys Met Lys Ser Arg
            340                 345                 350

Lys Ala Cys Gly Leu Ala Ile Gly Ala Thr Leu Ile Asp Ala Asp Lys
        355                 360                 365

Trp Ser Ile Thr Gly Glu Ala Arg Leu Ile Asn Glu Arg Ala Ala His
    370                 375                 380
```

```
Met Asn Ala Gln Phe Arg Phe Gly Phe Ser Leu Tyr Tyr Pro Asn Phe
385                 390                 395                 400

Leu Ser Arg Tyr Gln Asn Pro Gly Val Ser Gly Phe Phe Leu Leu
            405                 410                 415

Thr Ser Phe Cys Ile Ala Tyr Leu Phe Phe Lys Ile His Ser His Lys
            420                 425                 430

Asn Ser Leu Ile Ile Asn Phe Leu Glu Ala Asn Leu Glu Ile Thr Thr
            435                 440                 445

Leu Arg Lys Lys His Tyr Thr Asn Ile Ser Ile Leu Ser Thr Arg Pro
450                 455                 460

Tyr Ser Met
465

<210> SEQ ID NO 151
<211> LENGTH: 390
<212> TYPE: PRT
<213> ORGANISM: Chlamydia sp.

<400> SEQUENCE: 151

Lys Leu Leu Lys Ser Ala Leu Leu Phe Ala Ala Thr Gly Ser Ala Leu
1               5                   10                  15

Ser Leu Gln Ala Leu Pro Val Gly Asn Pro Ala Glu Pro Ser Leu Leu
            20                  25                  30

Ile Asp Gly Thr Met Trp Glu Gly Ala Ser Gly Asp Pro Cys Asp Pro
        35                  40                  45

Cys Ala Thr Trp Cys Asp Ala Ile Ser Ile Arg Ala Gly Tyr Tyr Gly
    50                  55                  60

Asp Tyr Val Phe Asp Arg Val Leu Lys Val Asp Val Asn Lys Thr Phe
65                  70                  75                  80

Ser Gly Met Ala Lys Ser Pro Thr Glu Ala Thr Gly Thr Ala Ser Ala
                85                  90                  95

Thr Thr Thr Ala Val Asp Arg Thr Asn Leu Ala Tyr Gly Lys His Leu
            100                 105                 110

Gln Asp Ala Glu Trp Phe Thr Asn Ala Ala Phe Leu Ala Leu Asn Ile
        115                 120                 125

Trp Asp Arg Phe Asp Ile Phe Cys Thr Leu Gly Ala Ser Asn Gly Tyr
130                 135                 140

Phe Lys Ala Ser Ser Ala Ala Phe Asn Leu Val Gly Leu Ile Gly Leu
145                 150                 155                 160

Lys Gly Thr Asp Phe Asn Asn Gln Leu Pro Asn Val Ala Ile Thr Gln
                165                 170                 175

Gly Val Val Glu Phe Tyr Thr Asp Thr Thr Phe Ser Trp Ser Val Gly
            180                 185                 190

Ala Arg Gly Ala Leu Trp Glu Cys Gly Cys Ala Thr Leu Gly Ala Glu
        195                 200                 205

Phe Gln Tyr Ala Gln Ser Asn Pro Lys Ile Glu Met Leu Asn Val Thr
    210                 215                 220

Ser Ser Pro Ala Gln Phe Val Ile His Lys Pro Arg Gly Tyr Lys Gly
225                 230                 235                 240

Thr Gly Ser Asn Phe Pro Leu Pro Ile Asp Ala Gly Thr Glu Ala Ala
                245                 250                 255

Thr Asp Thr Lys Ser Ala Thr Leu Lys Tyr His Glu Trp Gln Val Gly
            260                 265                 270

Leu Ala Leu Ser Tyr Arg Leu Asn Met Leu Val Pro Tyr Ile Gly Val
        275                 280                 285
```

```
Asn Trp Ser Arg Ala Thr Phe Asp Ala Asp Thr Ile Arg Ile Ala Gln
        290                 295                 300

Pro Lys Leu Ala Thr Ala Val Leu Asp Leu Thr Thr Trp Asn Pro Thr
305                 310                 315                 320

Leu Leu Gly Lys Ala Thr Thr Val Asp Gly Thr Asn Thr Tyr Ser Asp
                325                 330                 335

Phe Leu Gln Leu Ala Ser Ile Gln Ile Asn Lys Met Lys Ser Arg Lys
                340                 345                 350

Ala Cys Gly Val Ala Val Gly Ala Thr Leu Ile Asp Ala Asp Lys Trp
                355                 360                 365

Ser Ile Thr Gly Asp Ala Arg Leu Ile His Glu Arg Ala Ala His Met
370                 375                 380

Asn Ala Gln Phe Arg Phe
385                 390

<210> SEQ ID NO 152
<211> LENGTH: 356
<212> TYPE: PRT
<213> ORGANISM: Chlamydia sp.

<400> SEQUENCE: 152

Met Lys Lys Leu Leu Lys Ser Ala Leu Leu Phe Ala Ala Thr Gly Ser
1               5                   10                  15

Ala Leu Ser Leu Gln Ala Leu Pro Val Gly Asn Pro Ala Glu Pro Ser
                20                  25                  30

Leu Leu Ile Asp Gly Thr Met Trp Glu Gly Ala Ser Gly Asp Pro Cys
            35                  40                  45

Asp Pro Cys Ala Thr Trp Cys Asp Ala Ile Ser Ile Arg Ala Gly Tyr
        50                  55                  60

Tyr Gly Asp Tyr Val Phe Asp Arg Val Leu Lys Val Asp Val Asn Lys
65                  70                  75                  80

Thr Phe Ser Gly Met Ala Lys Ser Pro Thr Glu Ala Thr Gly Thr Ala
                85                  90                  95

Ser Ala Thr Thr Thr Ala Val Asp Arg Thr Asn Leu Ala Tyr Gly Lys
                100                 105                 110

His Leu Gln Asp Ala Glu Trp Phe Thr Asn Ala Ala Phe Leu Ala Leu
            115                 120                 125

Asn Ile Trp Asp Arg Phe Asp Ile Phe Cys Thr Leu Gly Ala Ser Asn
130                 135                 140

Gly Tyr Phe Lys Ala Ser Ser Ala Ala Phe Asn Leu Val Gly Leu Ile
145                 150                 155                 160

Gly Leu Lys Gly Thr Asp Phe Asn Asn Gln Leu Pro Asn Val Ala Ile
                165                 170                 175

Thr Gln Gly Val Val Glu Phe Tyr Thr Asp Thr Thr Phe Ser Trp Ser
            180                 185                 190

Val Gly Ala Arg Gly Ala Leu Trp Glu Cys Gly Cys Ala Thr Leu Gly
        195                 200                 205

Ala Glu Phe Gln Tyr Ala Gln Ser Asn Pro Lys Ile Glu Met Leu Asn
210                 215                 220

Val Thr Ser Ser Pro Ala Gln Phe Val Ile His Lys Pro Arg Gly Tyr
225                 230                 235                 240

Lys Gly Thr Gly Ser Asn Phe Pro Leu Pro Ile Asp Ala Gly Thr Glu
                245                 250                 255

Ala Ala Thr Asp Thr Lys Ser Ala Thr Leu Lys Tyr His Glu Trp Gln
```

```
            260                 265                 270
Val Gly Leu Ala Leu Ser Tyr Arg Leu Asn Met Leu Val Pro Tyr Ile
            275                 280                 285

Gly Val Asn Trp Ser Arg Ala Thr Phe Asp Ala Asp Thr Ile Arg Ile
            290                 295                 300

Ala Gln Pro Lys Leu Ala Thr Ala Val Leu Asp Leu Thr Thr Trp Asn
305                 310                 315                 320

Pro Thr Leu Leu Gly Lys Ala Thr Thr Val Asp Gly Thr Asn Thr Tyr
                325                 330                 335

Ser Asp Phe Leu Gln Leu Ala Ser Ile Gln Ile Asn Lys Met Lys Ser
            340                 345                 350

Arg Lys Ala Cys
            355

<210> SEQ ID NO 153
<211> LENGTH: 382
<212> TYPE: PRT
<213> ORGANISM: Chlamydia sp.

<400> SEQUENCE: 153

Gln Ala Leu Pro Val Gly Asn Pro Ala Glu Pro Ser Leu Leu Ile Asp
1               5                   10                  15

Gly Thr Met Trp Glu Gly Ala Ser Gly Asp Pro Cys Asp Pro Cys Ala
            20                  25                  30

Thr Trp Cys Asp Ala Ile Ser Ile Arg Ala Gly Tyr Tyr Gly Asp Tyr
            35                  40                  45

Val Phe Asp Arg Val Leu Lys Val Asp Val Asn Lys Thr Phe Ser Gly
        50                  55                  60

Met Ala Ala Thr Pro Thr Gln Ala Thr Gly Asn Ala Ser Asn Thr Asn
65                  70                  75                  80

Gln Pro Glu Ala Asn Gly Arg Pro Asn Ile Ala Tyr Gly Arg His Met
            85                  90                  95

Gln Asp Ala Glu Trp Phe Ser Asn Ala Ala Phe Leu Ala Leu Asn Ile
            100                 105                 110

Trp Asp Arg Phe Asp Ile Phe Cys Thr Leu Gly Ala Ser Asn Gly Tyr
        115                 120                 125

Phe Lys Ser Ser Ser Ala Ala Phe Asn Leu Val Gly Leu Ile Gly Phe
    130                 135                 140

Ser Ala Thr Ser Ser Thr Ser Thr Glu Leu Pro Met Gln Leu Pro Asn
145                 150                 155                 160

Val Gly Ile Thr Gln Gly Val Val Glu Phe Tyr Thr Asp Thr Ser Phe
            165                 170                 175

Ser Trp Ser Val Gly Ala Arg Gly Ala Leu Trp Glu Cys Gly Cys Ala
            180                 185                 190

Thr Leu Gly Ala Glu Phe Gln Tyr Ala Gln Ser Asn Pro Lys Ile Glu
        195                 200                 205

Val Leu Asn Val Thr Ser Ser Pro Ala Gln Phe Val Ile His Lys Pro
    210                 215                 220

Arg Gly Tyr Lys Gly Ala Ser Ser Asn Phe Pro Leu Pro Ile Thr Ala
225                 230                 235                 240

Gly Thr Thr Glu Ala Thr Asp Thr Lys Ser Ala Thr Ile Lys Tyr His
            245                 250                 255

Glu Trp Gln Val Gly Leu Ala Leu Ser Tyr Arg Leu Asn Met Leu Val
            260                 265                 270
```

```
Pro Tyr Ile Gly Val Asn Trp Ser Arg Ala Thr Phe Asp Ala Asp Thr
            275                 280                 285

Ile Arg Ile Ala Gln Pro Lys Leu Lys Ser Glu Ile Leu Asn Ile Thr
        290                 295                 300

Thr Trp Asn Pro Ser Leu Leu Gly Ser Thr Thr Leu Pro Asn Asn
305                 310                 315                 320

Gly Gly Lys Asp Val Leu Ser Asp Val Leu Gln Ile Ala Ser Ile Gln
                325                 330                 335

Ile Asn Lys Met Lys Ser Arg Lys Ala Cys Gly Val Ala Val Gly Ala
                340                 345                 350

Thr Leu Ile Asp Ala Asp Lys Trp Ser Ile Thr Gly Glu Ala Arg Leu
            355                 360                 365

Ile Asn Glu Arg Ala Ala His Met Asn Ala Gln Phe Arg Phe
        370                 375                 380

<210> SEQ ID NO 154
<211> LENGTH: 388
<212> TYPE: PRT
<213> ORGANISM: Chlamydia sp.

<400> SEQUENCE: 154

Leu Leu Lys Ser Ala Leu Leu Phe Ala Ala Thr Gly Ser Ala Leu Ser
1               5                   10                  15

Leu Gln Ala Leu Pro Val Gly Asn Pro Ala Glu Pro Ser Leu Leu Ile
            20                  25                  30

Asp Gly Thr Met Trp Glu Gly Ala Ser Gly Asp Pro Cys Asp Pro Cys
        35                  40                  45

Ala Thr Trp Cys Asp Ala Ile Ser Ile Arg Ala Gly Tyr Tyr Gly Asp
    50                  55                  60

Tyr Val Phe Asp Arg Val Leu Lys Val Asp Val Asn Lys Thr Ile Ser
65                  70                  75                  80

Gly Met Gly Ala Ala Pro Thr Gly Ser Ala Ala Asp Tyr Lys Thr
                85                  90                  95

Pro Thr Asp Arg Pro Asn Ile Ala Tyr Gly Lys His Leu Gln Asp Ala
            100                 105                 110

Glu Trp Phe Thr Asn Ala Ala Phe Leu Ala Leu Asn Ile Trp Asp Arg
        115                 120                 125

Phe Asp Ile Phe Cys Thr Leu Gly Ala Ser Asn Gly Tyr Phe Lys Ala
    130                 135                 140

Ser Ser Ala Ala Phe Asn Leu Val Gly Leu Ile Gly Val Lys Gly Thr
145                 150                 155                 160

Ser Val Ala Ala Asp Gln Leu Pro Asn Val Gly Ile Thr Gln Gly Ile
                165                 170                 175

Val Glu Phe Tyr Thr Asp Thr Thr Phe Ser Trp Ser Val Gly Ala Arg
            180                 185                 190

Gly Ala Leu Trp Glu Cys Gly Cys Ala Thr Leu Gly Ala Glu Phe Gln
        195                 200                 205

Tyr Ala Gln Ser Asn Pro Lys Ile Glu Met Leu Asn Val Ile Ser Ser
    210                 215                 220

Pro Thr Gln Phe Val Val His Lys Pro Arg Gly Tyr Lys Gly Thr Gly
225                 230                 235                 240

Ser Asn Phe Pro Leu Pro Leu Thr Ala Gly Thr Asp Gly Ala Thr Asp
                245                 250                 255

Thr Lys Ser Ala Thr Leu Lys Tyr His Glu Lys Phe Cys Asp Phe Leu
            260                 265                 270
```

```
Gln Ile Trp Gln Val Gly Leu Ala Leu Ser Tyr Arg Leu Asn Met Leu
            275                 280                 285

Val Pro Tyr Ile Gly Val Asn Trp Ser Arg Ala Thr Phe Asp Ala Asp
        290                 295                 300

Ser Ile Arg Ile Ala Gln Pro Lys Leu Ala Ala Val Leu Asn Leu
305                 310                 315                 320

Thr Thr Trp Asn Pro Thr Leu Leu Gly Glu Thr Ala Leu Asp Ala
                325                 330                 335

Ser Asn Ala Ser Ile Gln Ile Asn Lys Met Lys Ser Arg Lys Ala Cys
                340                 345                 350

Gly Val Ala Val Gly Ala Thr Leu Ile Asp Ala Asp Lys Trp Ser Ile
                355                 360                 365

Thr Gly Glu Ala Arg Leu Ile Asn Glu Arg Ala Ala His Met Asn Ala
370                 375                 380

Gln Phe Arg Phe
385

<210> SEQ ID NO 155
<211> LENGTH: 366
<212> TYPE: PRT
<213> ORGANISM: Chlamydia sp.

<400> SEQUENCE: 155

Met Lys Lys Leu Leu Lys Ser Ala Leu Leu Phe Ala Ala Thr Gly Ser
1               5                   10                  15

Ala Leu Ser Leu Gln Ala Leu Pro Val Gly Asn Pro Ala Glu Pro Ser
            20                  25                  30

Leu Leu Ile Asp Gly Thr Met Trp Glu Gly Ala Ser Gly Asp Pro Cys
        35                  40                  45

Asp Pro Cys Ala Thr Trp Cys Asp Ala Ile Ser Ile Arg Ala Gly Tyr
    50                  55                  60

Tyr Gly Asp Tyr Val Phe Asp Arg Val Leu Lys Val Asp Val Asn Lys
65                  70                  75                  80

Thr Phe Ser Gly Met Ala Ala Thr Pro Thr Gln Ala Thr Gly Asn Ala
                85                  90                  95

Ser Asn Thr Asn Gln Pro Glu Ala Asn Gly Arg Pro Asn Ile Ala Tyr
            100                 105                 110

Gly Arg His Met Gln Asp Ala Glu Trp Phe Ser Asn Ala Ala Phe Leu
        115                 120                 125

Ala Leu Asn Ile Trp Asp Arg Phe Asp Ile Phe Cys Thr Leu Gly Ala
    130                 135                 140

Ser Asn Gly Tyr Phe Lys Ser Ser Ser Ala Ala Phe Asn Leu Val Gly
145                 150                 155                 160

Leu Ile Gly Phe Ser Ala Thr Ser Ser Thr Ser Thr Glu Leu Pro Met
                165                 170                 175

Gln Leu Pro Asn Val Gly Ile Thr Gln Gly Val Val Glu Phe Tyr Thr
            180                 185                 190

Asp Thr Ser Phe Ser Trp Ser Val Gly Ala Arg Gly Ala Leu Trp Glu
        195                 200                 205

Cys Gly Cys Ala Thr Leu Gly Ala Glu Phe Gln Tyr Ala Gln Ser Asn
    210                 215                 220

Pro Lys Ile Glu Val Leu Asn Val Thr Ser Pro Ala Gln Phe Val
225                 230                 235                 240

Ile His Lys Pro Arg Gly Tyr Lys Gly Ala Ser Ser Asn Phe Pro Leu
```

```
                        245                 250                 255
Pro Ile Thr Ala Gly Thr Thr Glu Ala Thr Asp Thr Lys Ser Ala Thr
                260                 265                 270

Ile Lys Tyr His Glu Trp Gln Val Gly Leu Ala Leu Ser Tyr Arg Leu
            275                 280                 285

Asn Met Leu Val Pro Tyr Ile Gly Val Asn Trp Ser Arg Ala Thr Phe
        290                 295                 300

Asp Ala Asp Thr Ile Arg Ile Ala Gln Pro Lys Leu Lys Ser Glu Ile
305                 310                 315                 320

Leu Asn Ile Thr Thr Trp Asn Pro Ser Leu Leu Gly Ser Thr Thr Ala
                325                 330                 335

Leu Pro Asn Asn Ala Gly Lys Asp Val Leu Ser Asp Val Leu Gln Ile
            340                 345                 350

Ala Ser Ile Gln Ile Asn Lys Met Lys Ser Arg Lys Ala Cys
        355                 360                 365

<210> SEQ ID NO 156
<211> LENGTH: 402
<212> TYPE: PRT
<213> ORGANISM: Chlamydia sp.

<400> SEQUENCE: 156

Met Lys Lys Leu Leu Lys Ser Ala Leu Leu Phe Ala Ala Thr Gly Ser
1               5                   10                  15

Ala Leu Ser Leu Gln Ala Leu Pro Val Gly Asn Pro Ala Glu Pro Ser
            20                  25                  30

Leu Leu Ile Asp Gly Thr Met Trp Glu Gly Ala Ser Gly Asp Pro Cys
        35                  40                  45

Asp Pro Cys Ser Thr Trp Cys Asp Ala Ile Ser Ile Arg Ala Gly Tyr
    50                  55                  60

Tyr Gly Asp Tyr Val Phe Asp Arg Val Leu Lys Val Asp Val Asn Lys
65                  70                  75                  80

Thr Phe Thr Gly Met Ala Ala Thr Pro Thr Glu Ala Ser Gly Asn Ala
                85                  90                  95

Thr Asn Thr Gly Thr Pro Glu Ala Asn Gly Arg Ala Asn Ile Ala Tyr
            100                 105                 110

Gly Arg His Met Gln Asp Ala Glu Trp Phe Ser Asn Ala Ala Phe Leu
        115                 120                 125

Ala Leu Asn Ile Trp Asp Arg Phe Asp Ile Phe Cys Thr Leu Gly Ala
    130                 135                 140

Ser Asn Gly Tyr Phe Lys Ala Ser Ser Ala Ala Phe Asn Leu Val Gly
145                 150                 155                 160

Leu Ile Gly Phe Ser Ala Ser Ser Ala Val Ser Thr Asp Leu Pro Lys
                165                 170                 175

Gln Leu Pro Asn Val Ala Ile Thr Gln Gly Val Val Glu Phe Tyr Thr
            180                 185                 190

Asp Thr Ser Phe Ser Trp Ser Val Gly Ala Arg Gly Ala Leu Trp Glu
        195                 200                 205

Cys Gly Cys Ala Thr Leu Gly Ala Glu Phe Gln Tyr Ala Gln Ser Asn
    210                 215                 220

Arg Lys Ile Glu Met Leu Asn Val Thr Ser Ser Pro Ala Gln Phe Val
225                 230                 235                 240

Ile His Lys Pro Arg Gly Tyr Lys Gly Thr Ser Ser Asn Phe Pro Leu
                245                 250                 255
```

```
Pro Ile Thr Ala Gly Thr Asp Asp Ala Thr Asp Thr Lys Ser Ala Thr
            260                 265                 270

Ile Lys Tyr His Glu Trp Gln Val Gly Leu Ala Leu Ser Tyr Arg Leu
        275                 280                 285

Asn Met Leu Val Pro Tyr Ile Gly Val Asn Trp Ser Arg Ala Thr Phe
    290                 295                 300

Asp Ala Asp Thr Ile Arg Ile Ala Gln Pro Lys Leu Lys Ser Glu Ile
305                 310                 315                 320

Leu Asn Ile Thr Thr Trp Asn Pro Ser Leu Ile Gly Ser Thr Thr Ala
                325                 330                 335

Leu Pro Asn Asn Ser Gly Lys Asp Val Leu Ser Asp Val Leu Gln Ile
                340                 345                 350

Ala Ser Ile Gln Ile Asn Lys Met Lys Ser Arg Lys Ser Cys Gly Val
            355                 360                 365

Ala Val Gly Ala Thr Leu Ile Asp Ala Asp Lys Trp Ser Ile Thr Gly
        370                 375                 380

Glu Ala Arg Leu Ile Asn Glu Arg Ala Ala His Met Asn Ala Gln Phe
385                 390                 395                 400

Arg Phe

<210> SEQ ID NO 157
<211> LENGTH: 391
<212> TYPE: PRT
<213> ORGANISM: Chlamydia sp.

<400> SEQUENCE: 157

Lys Ser Ala Leu Leu Phe Ala Ala Thr Gly Ser Ala Leu Ser Leu Gln
1               5                   10                  15

Ala Leu Pro Val Gly Asn Pro Ala Glu Pro Ser Leu Leu Ile Asp Gly
            20                  25                  30

Thr Met Trp Glu Gly Ala Ser Gly Asp Pro Cys Asp Pro Cys Ala Thr
        35                  40                  45

Trp Cys Asp Ala Ile Ser Ile Arg Ala Gly Tyr Tyr Gly Asp Tyr Val
    50                  55                  60

Phe Asp Arg Val Leu Lys Val Asp Val Asn Lys Thr Phe Ser Gly Met
65                  70                  75                  80

Ala Ala Ile Pro Thr Glu Ser Ser Gly Thr Val Ser Ser Ala Lys Gln
                85                  90                  95

Ala Val Asp Arg Val Asn Leu Ala Tyr Gly Lys His Leu Gln Asp Ala
            100                 105                 110

Glu Trp Phe Thr Asn Ser Ala Phe Leu Ala Leu Asn Ile Trp Asp Arg
        115                 120                 125

Phe Asp Ile Phe Cys Thr Leu Gly Ala Ser Asn Gly Tyr Phe Lys Gly
    130                 135                 140

Ser Ser Ala Ala Phe Asn Leu Val Gly Leu Phe Gly Ile Ala Gly Asn
145                 150                 155                 160

Ser Glu Ser Asn Ala Leu Asn Asp Gln Leu Pro Asn Val Ala Ile Thr
                165                 170                 175

Gln Gly Ile Val Glu Phe Tyr Thr Asp Thr Thr Phe Ser Trp Ser Val
            180                 185                 190

Gly Ala Arg Gly Ala Leu Trp Glu Cys Gly Cys Ala Thr Leu Gly Ala
        195                 200                 205

Glu Phe Gln Tyr Ala Gln Ser Asn Pro Lys Ile Glu Met Leu Asn Val
    210                 215                 220
```

-continued

```
Thr Ser Ser Pro Ala Gln Phe Val Ile His Lys Pro Arg Gly Tyr Lys
225                 230                 235                 240

Gly Thr Thr Ser Asn Phe Pro Leu Pro Leu Thr Ala Gly Thr Asp Thr
                245                 250                 255

Ala Thr Asp Thr Lys Ser Ala Thr Ile Lys Tyr His Glu Trp Gln Val
            260                 265                 270

Gly Leu Ala Leu Ser Tyr Arg Leu Asn Met Leu Val Pro Tyr Ile Gly
        275                 280                 285

Val Asn Trp Ser Arg Ala Thr Phe Asp Ala Asp Thr Ile Arg Ile Ala
    290                 295                 300

Gln Pro Lys Leu Ala Thr Ala Val Leu Asp Ala Lys Thr Trp Asn Pro
305                 310                 315                 320

Thr Ile Thr Gly Ala Ser Gly Ser Val Asp Asn Thr Asn Lys Trp Ser
                325                 330                 335

Asp Asn Leu Gln Ile Ala Ser Ile Gln Ile Asn Lys Met Lys Ser Arg
            340                 345                 350

Lys Ala Cys Gly Val Ala Val Gly Ala Thr Leu Ile Asp Ala Asp Lys
        355                 360                 365

Trp Ser Ile Thr Gly Glu Ala Arg Leu Ile Asn Glu Arg Ala Ala His
    370                 375                 380

Met Asn Ala Gln Phe Arg Phe
385                 390

<210> SEQ ID NO 158
<211> LENGTH: 376
<212> TYPE: PRT
<213> ORGANISM: Chlamydia sp.

<400> SEQUENCE: 158

Met Lys Lys Leu Leu Lys Ser Ala Leu Leu Phe Ala Ala Thr Gly Ser
1               5                   10                  15

Ala Leu Ser Leu Gln Ala Leu Pro Val Gly Asn Pro Ala Glu Pro Ser
            20                  25                  30

Leu Leu Ile Asp Gly Thr Met Trp Glu Gly Ala Ser Gly Asp Pro Cys
        35                  40                  45

Asp Pro Cys Ala Thr Trp Cys Asp Ala Ile Ser Ile Arg Ala Gly Tyr
    50                  55                  60

Tyr Gly Asp Tyr Val Phe Asp Arg Val Leu Lys Val Asp Val Asn Lys
65                  70                  75                  80

Thr Phe Ser Gly Met Ala Ala Pro Thr Ala Thr Gly Ala Ser Ala Thr
                85                  90                  95

Ala Asp Arg Asn Ile Ala Tyr Gly Lys His Leu Gln Asp Ala Glu Trp
            100                 105                 110

Phe Thr Asn Ala Ala Phe Leu Ala Leu Asn Ile Trp Asp Arg Phe Asp
        115                 120                 125

Ile Phe Cys Thr Leu Gly Ala Ser Asn Gly Tyr Phe Lys Ala Ser Ser
    130                 135                 140

Ala Ala Phe Asn Leu Val Gly Leu Ile Gly Val Gly Thr Asp Gln Leu
145                 150                 155                 160

Pro Asn Val Ala Ile Thr Gln Gly Val Val Glu Phe Tyr Thr Asp Thr
                165                 170                 175

Thr Phe Ser Trp Ser Val Gly Ala Arg Gly Ala Leu Trp Glu Cys Gly
            180                 185                 190

Cys Ala Thr Leu Gly Ala Glu Phe Gln Tyr Ala Gln Ser Asn Pro Lys
        195                 200                 205
```

-continued

```
Ile Glu Met Leu Asn Val Thr Ser Ser Pro Ala Gln Phe Val Ile His
    210                 215                 220
Lys Pro Arg Gly Tyr Lys Gly Thr Ser Ser Asn Phe Pro Leu Pro Ile
225                 230                 235                 240
Thr Ala Gly Thr Asp Ala Thr Asp Thr Lys Ser Ala Thr Ile Lys Tyr
                245                 250                 255
His Glu Trp Gln Val Gly Leu Ala Leu Ser Tyr Arg Leu Asn Met Leu
            260                 265                 270
Val Pro Tyr Ile Gly Val Asn Trp Ser Arg Ala Thr Phe Asp Ala Asp
        275                 280                 285
Thr Ile Arg Ile Ala Gln Pro Lys Leu Ala Thr Ala Ile Leu Asn Leu
    290                 295                 300
Thr Thr Trp Asn Pro Thr Leu Leu Gly Ala Thr Leu Asp Thr Asn Phe
305                 310                 315                 320
Ser Asp Phe Leu Gln Ile Ala Ser Ile Gln Ile Asn Lys Met Lys Ser
                325                 330                 335
Arg Lys Ala Cys Gly Val Ala Val Gly Ala Thr Leu Ile Asp Ala Asp
            340                 345                 350
Lys Trp Ser Ile Thr Gly Glu Ala Arg Leu Ile Asn Glu Arg Ala Ala
        355                 360                 365
His Met Asn Ala Gln Phe Arg Phe
    370                 375
```